US009084770B2

(12) United States Patent
Tachas et al.

(10) Patent No.: US 9,084,770 B2
(45) Date of Patent: Jul. 21, 2015

(54) MODULATION OF INSULIN LIKE GROWTH FACTOR I RECEPTOR EXPRESSION IN CANCER

(75) Inventors: George Tachas, Kew (AU); Lynne Maree Atley, Williamstown (AU); Christopher J. Wraight, Blackburn (AU)

(73) Assignee: Antisense Therapeutics, Ltd., Toorak (AU)

( * ) Notice: Subject to any disclaimer, the term of this patent is extended or adjusted under 35 U.S.C. 154(b) by 629 days.

(21) Appl. No.: 12/578,471

(22) Filed: Oct. 13, 2009

(65) Prior Publication Data

US 2010/0093832 A1 Apr. 15, 2010

Related U.S. Application Data

(60) Provisional application No. 61/105,367, filed on Oct. 14, 2008, provisional application No. 61/187,510, filed on Jun. 16, 2009, provisional application No. 61/233,772, filed on Aug. 13, 2009.

(51) Int. Cl.
*C12N 15/113* (2010.01)
*A61K 31/337* (2006.01)
*A61K 31/7052* (2006.01)

(52) U.S. Cl.
CPC ........... *A61K 31/337* (2013.01); *A61K 31/7052* (2013.01)

(58) Field of Classification Search
None
See application file for complete search history.

(56) References Cited

U.S. PATENT DOCUMENTS

2004/0202655 A1* 10/2004 Morton et al. ............. 424/143.1
2006/0234239 A1* 10/2006 Wraight et al. ................ 435/6

FOREIGN PATENT DOCUMENTS

| WO | WO 03100059 A2 * | 12/2003 |
| WO | 2004072284 | 8/2004 |
| WO | WO 2007092453 A2 * | 8/2007 |

OTHER PUBLICATIONS

Arteaga, et al., Blockade of the type I somatomedin receptor inhibits growth of human breast cancer cells in athymic mice., J. Clin. Invest. 84(5): 1418-1423 (1989).
Burfeind, et al., Antisense RNA to the type I insulin-like growth factor receptor suppresses tumor growth and prevents invasion by rat prostate cancer cells in vivo, PNAS Jul. 9, 1996 vol. 93 No. 14 7263-7268.
Cher, et al., Maspin expression inhibits osteolysis, tumor growth, and angiogenesis in a model of prostate cancer bone metastasis, PNAS Jun. 24, 2003 vol. 100 No. 13 7847-7852.
Cullen, et al., Insulin-like Growth Factor Receptor Expression and Function in Human Breast Cancer1, Cancer Research 50, 48-53, Jan. 1, 1990.
Foekens, et al., Prognostic Value of Receptors for Insulin-like Growth Factor 1, Somatostatin, and Epidermal Growth Factor in Human Breast Cancerl, Cancer Research 49, 7002-7009, Dec. 15, 1989.
Gleave, et al., Progression to Androgen Independence Is Delayed by Adjuvant Treatment with Antisense Bcl-2 Oligodeoxynucleotides after Castration in the LNCaP Prostate Tumor Model1, Clinical Cancer Research Oct. 5, 1999; 2891.
Going, et al., Molecular pathology and future developments, Eur J Cancer. Dec. 1999;35(14):1895-904.
Guo, et al., Characterization of insulinlike growth factor I receptors in human colon cancer, Gastroenterology. Apr. 1992;102(4 Pt 1):1101-8.
Kaiser, et al., Expression of insulin-like growth factor receptors I and II in normal human lung and in lung cancer, J Cancer Res Clin Oncol. 1993;119(11):665-8.
Leung, et al., Polymeric micellar paclitaxel phosphorylates Bcl-2 and induces apoptotic regression of androgen-independent LNCaP prostate tumors., Prostate. Jul. 1, 2000;44(2):156-63.
MacAulay, et al., Autocrine Function for Insulin-like Growth Factor I in Human Small Cell Lung Cancer Cell Lines and Fresh Tumor Cells., Cancer Research 50, 2511-2517, Apr. 15, 1990.
MacAulay, V.M. Insulin-like growth factors and cancer., Br J Cancer. Mar. 1992; 65(3): 311-320.
Miyake, et al., Novel therapeutic strategy for advanced prostate cancer using antisense oligodeoxynucleotides targeting anti-apoptotic genes upregulated after androgen withdrawal to delay androgen-independent progression and enhance chemosensitivity., Int J Urol. Jul. 2001;8(7):337-49.
Moody, et al., Growth factor and peptide receptors in small cell lung cancer, Life Sciences, vol. 52, Issue 14, 1993, pp. 1161-1173.
McCulloch, et al., BM18: A novel androgen-dependent human prostate cancer xenograft model derived from a bone metastasis., Prostate. Sep. 15, 2005;65(1):35-43.
Pollak, et al., Presence of somatomedin receptors on primary human breast and colon carcinomas., Cancer Letters, vol. 38, Issues 1-2, Dec. 1987, pp. 223-230.
Remacle-Bonnet, et al., Expresion of type I, but not type II insulin-like grown factor receptor on both undifferentiated and differentiated HT29 human colon carcinoma cell line, Journal of Clinical Endocrinology & Metabolism, vol. 75, 609-616, 1992.
Riedemann, et al., IGF1R signalling and its inhibition., Endocrine-Related Cancer 13 (Supplement_1) S33-43, 2006.
Salisbury, et al., Development of molecular agents for IGF receptor targeting., Horm Metab Res. Nov.-Dec. 2003, 35 (11-12):843-9.
Sato, et al., Intermittent androgen suppression delays progression to androgen-independent regulation of prostate-specific antigen gene in the LNCaP prostate tumour model., The Journal of Steroid Biochemistry and Molecular Biology, vol. 58, Issue 2, May 1996, pp. 139-146.
Ullrich, et al., Insulin-like growth factor I receptor primary structure: comparison with insulin receptor suggests structural determinants that define functional specificity., EMBO J. Oct. 1986; 5(10): 2503-2512.
Ullrich, et al., Signal transduction by receptors with tyrosine kinase activity., Cell. Apr. 20, 1990;61(2):203-12.
Zellweger, et al., Antitumor activity of antisense clusterin oligonucleotides is improved in vitro and in vivo by incorporation of 2'-O-(2-methoxy)ethyl chemistry., J Pharmacol Exp Ther. Sep. 2001;298(3):934-40.

* cited by examiner

*Primary Examiner* — Tracy Vivlemore
(74) *Attorney, Agent, or Firm* — Carol L. Francis; Bozicevic, Field & Francis LLP

(57) ABSTRACT

Provided herein are methods, compounds, and compositions for reducing expression of an IGF-IR mRNA and protein in an animal. Also provided herein are methods, compounds, and compositions that inhibit expression of IGF-IR in an animal. Such methods, compounds, and compositions are useful to treat, prevent, delay, or ameliorate the tumor or cancer, or a symptom thereof.

21 Claims, 22 Drawing Sheets

FIG. 1A(i)
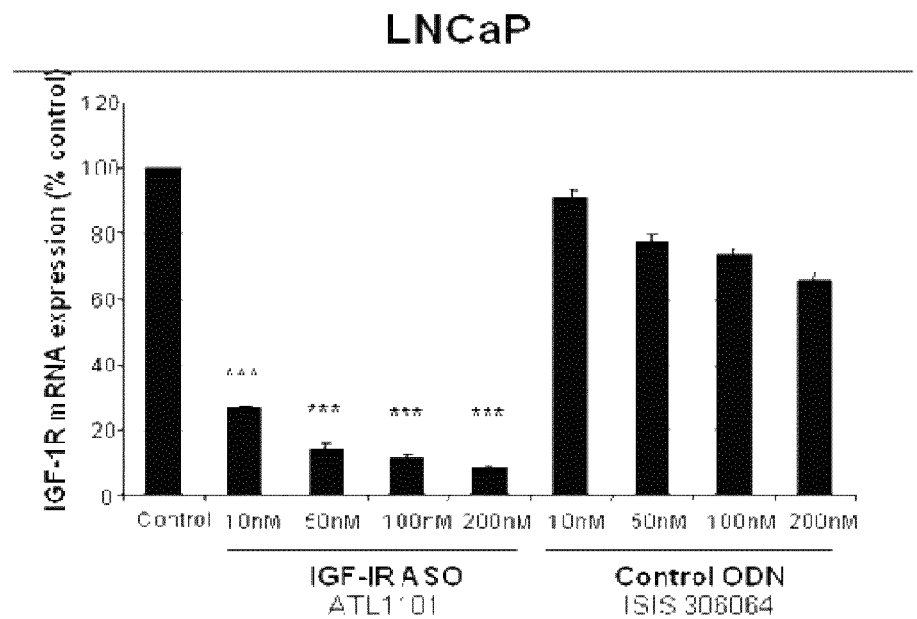
FIG. 1A(ii)
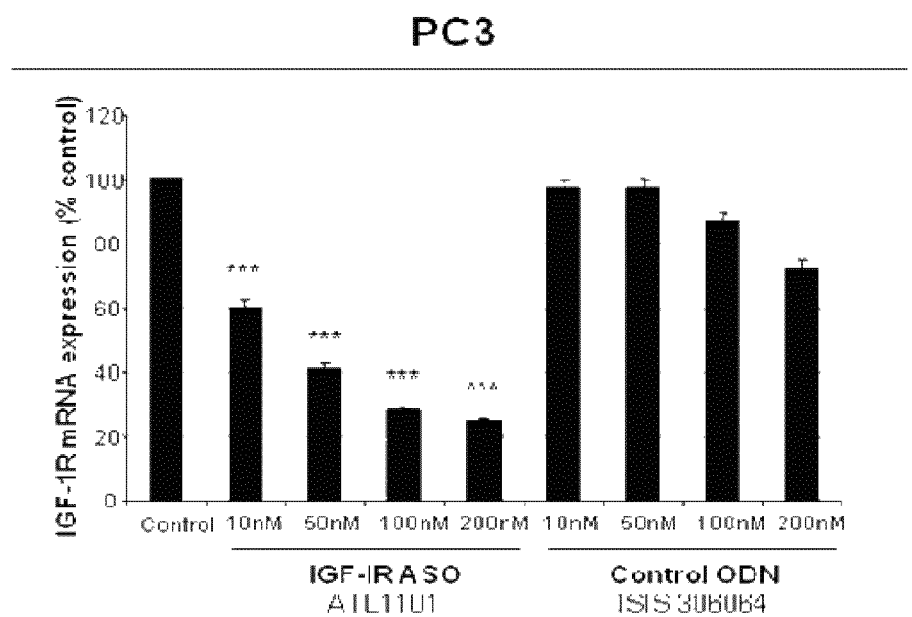

FIG. 1B(i)
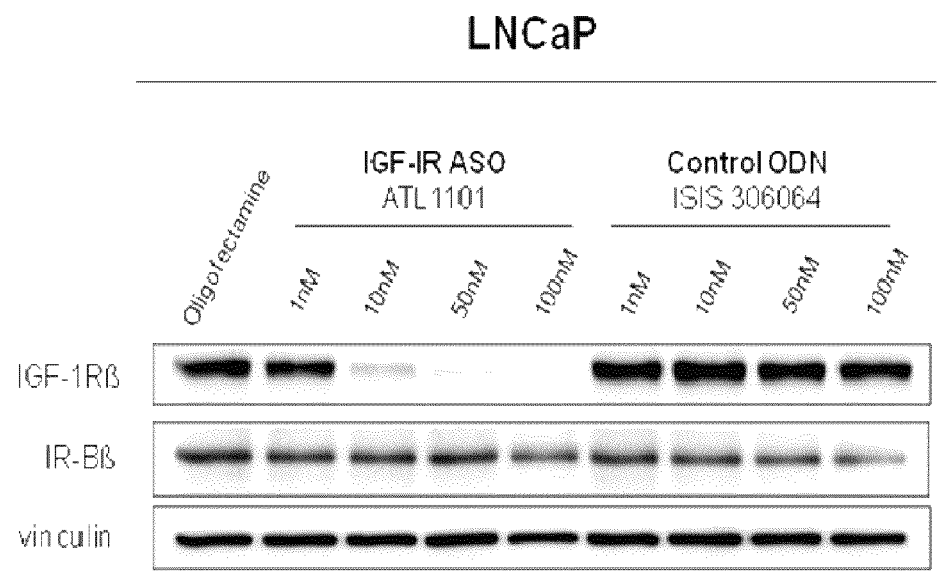
FIG. 1B(ii)
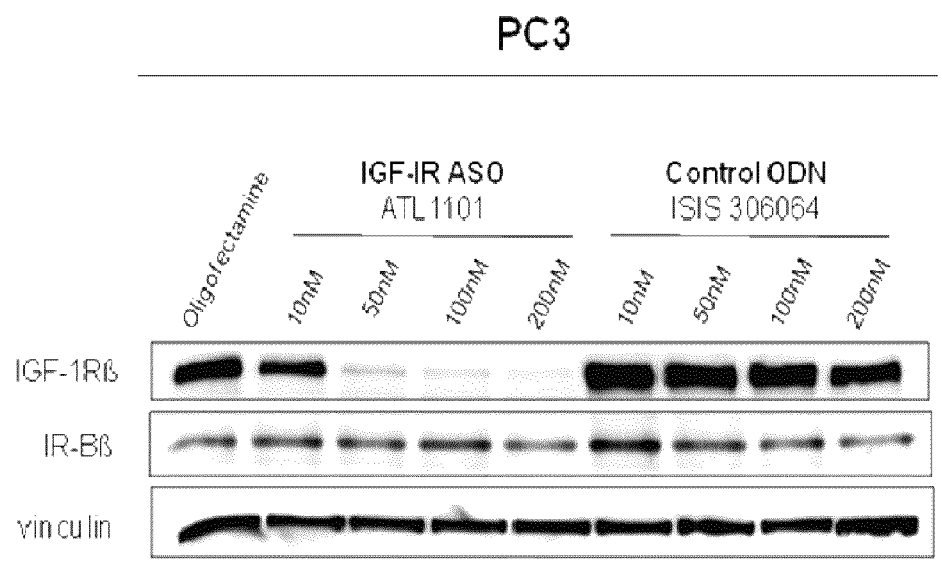

Fig. 4A(i)
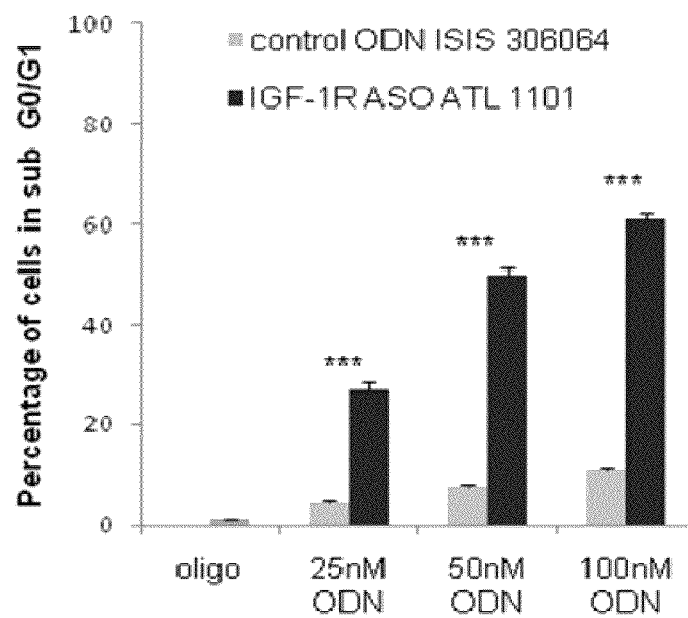
Fig. 4A(ii)
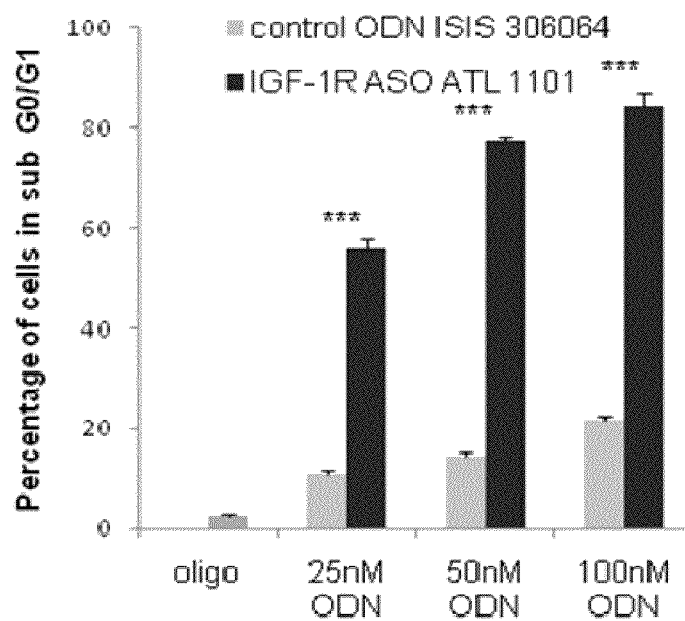

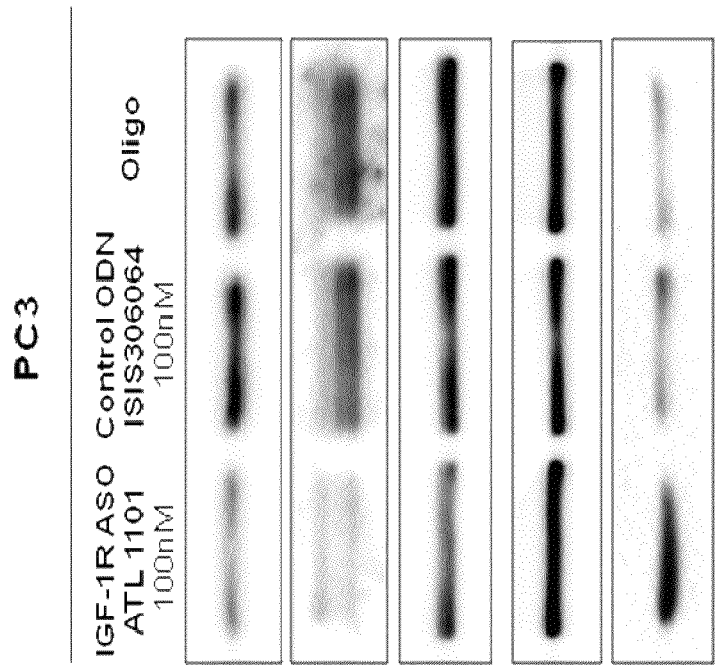
Fig. 4C(ii)
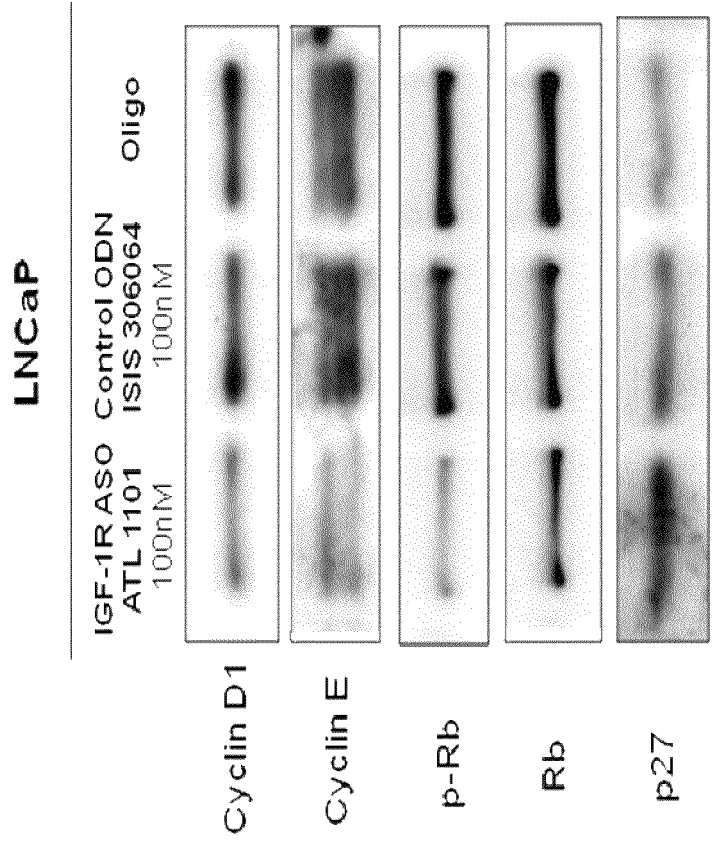
Fig. 4C(i)

Fig. 6

| | | | | | | | |
|---|---|---|---|---|---|---|---|
| 481 | gtgtgcgcgg | gccagggcgc | cgcgcgcgcg | agccccAgt | gtgtggcagc | ggcggcggcg |
| 541 | gcgggcgag | gctggggctc | ttgtttacca | gcattaactc | gctgagcgga | aaaaaaagg |
| 601 | gaaaaaaccc | gaggaggagc | gagcgcacca | ggcgaactcg | agagaggcgg | gagagcgaga |
| 661 | gggacgccgc | cagcgagcct | gcccacggcc | ggcgctcgca | gaccctcggc | cccgtcccc |
| 721 | ggatccccc | gcgccctcca | cgcccctccc | gcgcggggc | agctccacgg | cgccgctcgc |
| 781 | ct¹cggctgtg accttcagcg ag¹ccggagcc cccgcgcaga gcaggcggcg gcggcgggg |
| 841 | gccggcggg | ggccggccgg | gggccggcgg | ccgcgcagag | ccgggcgcg | cgcgcggagt |
| 901 | gctgagcgcg | gcgcggccgg | cccgccgctt | tgtgtgtgtc | ctggatttgg | gaaggagctc |
| 961 | gccggccgcg | cggcgctgag | ggaggaggcg | gcgcgagcg | gagccaggag | gaggaggagg |
| 1021 | agga² ggggga gccgctcatt catt² ttgact ccgcgttcct gcccctcgcc ggcctcgcct |
| 1081 | gtgacccgga | cttcggggcg | atcttgcgaa | ctgcgtcgcg | ccctcccgcg | gcggaagctc |
| 1141 | gggcgtccgg | ccgctcccg | cgcgtcccg | cccggcttgt | ttttcctgc | ctaggcagat |
| 1201 | ttgggctttg | cccccttct | ttgcagttt | cccccttcc | tgcctctccg | ggttttgaaaa |
| 1261 | tggagccga cgacgccgac agcccgcccc cgtgagggg cgccccgcc gggtcccga ctccgccgag |
| 1321 | ccctgggcg | ctgctgccg | cctgcggg | agcccgccg | cgtccgcccc | cgtccgcgca |
| 1381 | cccggaggc | cccggcggcg | gccct³tcgga gtattgttc cttcg³ccctt gttttttggag |
| 1441 | ggggagcgaa | gactgagtt | tttttttt | gagacttgtt | tccttcatt | tccttttttt | ctttctttt |
| 1501 | cttttttt | tttttttt | ttttgagaa | agggaattt | catcccaaat | aaaaggaATG |

Code
¹ASO 175314
²ASO 175323
³ASO 175317

MODULATION OF INSULIN LIKE GROWTH FACTOR I RECEPTOR EXPRESSION IN CANCER

CROSS-REFERENCE TO RELATED APPLICATIONS

This application claims priority benefit of U.S. provisional patent application U.S. Ser. No. 61/105,367, filed Oct. 14, 2008; U.S. provisional patent application U.S. Ser. No. 61/187,510, filed Jun. 16, 2009; and U.S. provisional patent application U.S. Ser. No. 61/233,772, filed Aug. 13, 2009. The contents of each application listed in this paragraph are fully incorporated by reference herein.

FIELD OF THE INVENTION

The present invention provides methods for the treatment of cancer. In one example, the present invention provides methods for the treatment of prostate cancer.

BACKGROUND OF THE INVENTION

The insulin-like growth factor receptor (IGF-IR) is composed of two types of subunits: an alpha subunit (a 130-135 kDa protein that is entirely extracellular and functions in ligand binding) and a beta subunit (a 95-kDa transmembrane protein, with transmembrane and cytoplasmic domains). The IGF-IR binds insulin-like growth factor I (IGF-I), or IGF-II or insulin at supraphysiological concentrations. The IGF-IR belongs to the family of tyrosine kinase growth factor receptors (Ullrich et al., 1990), and is structurally similar to the insulin receptor (Ullrich et al., 1986).

The IGF-IR is initially synthesized as a single chain pro-receptor polypeptide, which is processed by glycosylation, proteolytic cleavage, and covalent bonding to assemble into a mature 460 kDa heterotetramer comprising two alpha-sub-units and two beta-subunits. The beta subunit(s) possesses ligand-activated tyrosine kinase activity. This activity is implicated in the signaling pathways mediating ligand action which involve autophosphorylation of the beta-subunit and phosphorylation of IGF-IR substrates.

There is considerable evidence for a role for the IGF-IR in the maintenance of tumor cells in vitro. IGF-IR levels are elevated in tumors of lung (Kaiser et al., 1993; Moody et al., 1993; Macaulay et al., 1990), breast (Pollak et al., 1987; Foekens et al., 1989; Cullen et al., 1990; Arteaga et al., 1989), prostate and colon (Remade-Bonnet et al., 1992; Guo et al., 1992). For a review of the potential role of IGF-IR and the growth of a variety of human tumors see Macaulay, 1992.

SUMMARY OF THE INVENTION

Antisense oligonucleotides to IGF-IR have not been used in vivo to treat prostate cancer. Further, it is not clear what the hurdles for therapeutic activity might be, such as 1) limited tissue and cellular penetration of the antisense oligonucle-otide, 2) undesirable activities including hyperglycemia, or interference or modulation of the immune system in a way that affects its activity. The inventors have found that systemic administration of an antisense oligonucleotide to IGF-IR is effective in the treatment of IGF-IR positive tumors or cancers and does not cause hyperglycemia.

The present invention relates to a method for the treatment of an IGF-IR positive prostate tumor or prostate cancer in a subject, the method comprising systemically administering to the subject an effective amount of an antisense oligonucleotide which inhibits expression of IGF-IR.

In one embodiment of the invention, the antisense oligonucleotide comprises a sequence as provided in SEQ ID NO:43, SEQ ID NO:50, SEQ ID NO:53, SEQ ID NO:68, SEQ ID NO:73, SEQ ID NO:110, SEQ ID NO:115, SEQ ID NO:116, SEQ ID NO:122, SEQ ID NO:124, SEQ ID NO:125, or SEQ ID NO:131.

In one embodiment of the invention, the antisense oligonucleotide comprises a sequence as provided in SEQ ID NO:125.

In a further embodiment of the invention, the antisense oligonucleotide comprises at least two of the sequences as provided in SEQ ID NO:43, SEQ ID NO:50, SEQ ID NO:53, SEQ ID NO:68, SEQ ID NO:73, SEQ ID NO:110, SEQ ID NO:115, SEQ ID NO:116, SEQ ID NO:122, SEQ ID NO:124, SEQ ID NO:125, or SEQ ID NO:131.

In a further embodiment of the invention, at least two antisense oligonucleotides which inhibit expression of IGF-IR are administered to the subject.

In one embodiment of the invention, the antisense oligonucleotide reduces the size and/or growth of the tumor or cancer in the subject.

In a further embodiment, the method for the treatment of the prostate tumor or prostate cancer further comprises treating the subject with androgen withdrawal therapy.

The androgen withdrawal therapy may comprise surgical orchiectomy, or administration to the subject of a luteinizing hormone-releasing hormone antagonist, a luteinizing hormone-releasing hormone agonist, and/or an anti-androgen.

In one embodiment of the invention, the antisense oligonucleotide is administered at about the same time that androgen withdrawal therapy is initiated. In an alternate embodiment of the invention, the antisense oligonucleotide is administered after initiation of the androgen withdrawal therapy and before the tumor or cancer becomes androgen unresponsive/independent.

In one embodiment of the invention, the antisense oligonucleotide delays progression of the tumor or cancer from androgen responsive/dependent to androgen unresponsive/independent.

In one embodiment of the invention, the prostate tumor or prostate cancer is resistant to a taxane based agent and/or resistant to androgen withdrawal therapy.

In a further embodiment of the invention, the method for the treatment of the prostate tumor or prostate cancer further comprises administering to the subject an anti-neoplastic agent. The anti-neoplastic agent may be for example, radiation or chemotherapeutic.

In one embodiment of the invention, the method for the treatment of the prostate tumor or prostate cancer comprises administering to the subject a taxane based agent. In one embodiment of the invention, the taxane based agent blocks microtubule disassembly. The taxane based agent may be, for example, Docetaxel, Larotaxel, Ortataxel, Paclitaxel, or Tesetaxel.

The present invention also provides a method for treating an IGF-IR positive tumor or cancer in a subject, the method comprising systemically administering to the subject an effective amount of an antisense oligonucleotide, wherein the antisense oligonucleotide comprises a sequence as provided in SEQ ID NO:125.

In one embodiment of the invention, the cancer is squamous cell cancer, small cell lung cancer, non-small-cell lung cancer, adenocarcinoma of the lung, squamous carcinoma of the lung, cancer of the peritoneum, hepatocellular cancer, stomach cancer, gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial carcinoma, uterine carcinoma, salivary gland carcinoma, kidney cancer, renal cancer, prostate cancer, vulval cancer, thyroid cancer, hepatic carcinoma, anal carcinoma, penile carcinoma, head and neck cancer, Karposi's sarcoma, or melanoma.

In one embodiment of the invention, the tumor or cancer is androgen responsive/dependent. In a further embodiment of the invention, the androgen responsive/dependent tumor or cancer is prostate tumor or cancer.

In one embodiment of the invention, the antisense oligonucleotide reduces the size and/or growth of the tumor or cancer in the subject.

In a further embodiment, the method for the treatment of the tumor or cancer further comprises treating the subject with androgen withdrawal therapy.

The androgen withdrawal therapy may comprise surgical orchiectomy, or administration to the subject of a luteinizing hormone-releasing hormone antagonist, a luteinizing hormone-releasing hormone agonist, and/or an anti-androgen.

In one embodiment of the invention, the antisense oligonucleotide is administered at about the same time that androgen withdrawal therapy is initiated. In an alternate embodiment of the invention, the antisense oligonucleotide is administered after initiation of the androgen withdrawal therapy and before the tumor or cancer becomes androgen unresponsive/independent.

In one embodiment of the invention, the antisense oligonucleotide delays progression of the tumor or cancer from androgen responsive/dependent to androgen unresponsive/independent.

In another embodiment of the invention, the tumor or cancer is androgen unresponsive/independent. In a further embodiment of the invention, the androgen unresponsive/independent tumor or cancer is prostate tumor or cancer.

In a further embodiment of the invention, the method for the treatment of the tumor or cancer further comprises administering to the subject an anti-neoplastic agent. The anti-neoplastic agent may be for example, radiation or a chemotherapeutic.

In one embodiment of the invention, the method for the treatment of the tumor or cancer comprises administering to the subject a taxane based agent. In one embodiment of the invention, the taxane based agent blocks microtubule disassembly. The taxane based agent may be, for example, Docetaxel, Larotaxel, Ortataxel, Paclitaxel, or Tesetaxel.

The present invention also provides a method for enhancing the sensitivity of an IGF-IR positive tumor or cancer cell to a taxane based agent, the method comprising administering to the subject an effective amount of an agent that inhibits expression of IGF-IR.

In one embodiment of the invention, the tumor or cancer cell is androgen unresponsive/independent.

In one embodiment of the invention, the agent that inhibits expression of IGF-IR reduces transcription and/or translation of a gene encoding IGF-IR.

The agent that inhibits expression of IGF-IR may be a polynucleotide, for example, an antisense oligonucleotide, a small interfering RNA, a microRNA, or a catalytic polynucleotide.

In one embodiment of the invention, the polynucleotide is an antisense oligonucleotide that comprises, for example, a sequence as provided in SEQ ID NO:43, SEQ ID NO:50, SEQ ID NO:53, SEQ ID NO:68, SEQ ID NO:73, SEQ ID NO:110, SEQ ID NO:115, SEQ ID NO:116, SEQ ID NO:122, SEQ ID NO:124, SEQ ID NO:125, or SEQ ID NO:131.

The agent that inhibits expression of IGF-IR may be a polypeptide, for example, an antibody or an antigenic binding fragment thereof.

In one embodiment of the invention, the taxane based agent blocks microtubule disassembly. The taxane based agent may be, for example, Docetaxel, Larotaxel, Ortataxel, Paclitaxel, or Tesetaxel.

In one embodiment of the invention, the cancer is squamous cell cancer, small cell lung cancer, non-small-cell lung cancer, adenocarcinoma of the lung, squamous carcinoma of the lung, cancer of the peritoneum, hepatocellular cancer, stomach cancer, gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial carcinoma, uterine carcinoma, salivary gland carcinoma, kidney cancer, renal cancer, prostate cancer, vulval cancer, thyroid cancer, hepatic carcinoma, anal carcinoma, penile carcinoma, head and neck cancer, Karposi's sarcoma, or melanoma.

In a further embodiment of the invention, the method further comprises administering to the subject a taxane based agent.

The present invention also provides a method for treating an IGF-IR positive tumor or cancer, the method comprising administering to the subject an effective amount of an agent that inhibits expression of IGF-IR and a taxane based agent.

In one embodiment of the invention, the tumor or cancer is androgen unresponsive/independent.

In a further embodiment of the invention, the tumor or cancer is resistant to a taxane based agent.

In one embodiment of the invention, the agent that inhibits expression of IGF-IR and the taxane based agent are administered sequentially. For example, the agent that inhibits expression of IGF-IR may be administered to the subject prior to administering the taxane based agent.

Agents that inhibit expression of IGF-IR and taxane based agents are described herein and shall be taken to apply mutatis mutandis to this embodiment of the invention.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is also provided.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, group of steps or group of compositions of matter.

Each embodiment described herein is to be applied mutatis mutandis to each and every other embodiment unless specifically stated otherwise.

The invention is hereinafter described by way of the following non-limiting Examples and with reference to the accompanying figures.

TABLE 1

Antisense oligonucleotide compounds to human IGF-IR

| ISIS # | REGION | TARGET SEQ ID NO | TARGET SITE | SEQUENCE/DESCRIPTION | %INHIB | SEQ ID NO |
|---|---|---|---|---|---|---|
| 323695 | 5'UTR | NM_000875.2 | 25 | cctttatttgggatgaaat | 50 | 1 |
| 323696 | Start Codon | NM_000875.2 | 37 | ccagacttcattcctttat | 44 | 2 |
| 323697 | Coding | NM_000875.2 | 157 | tgatagtcgttgcggatgtc | 73 | 3 |
| 323698 | Coding | NM_000875.2 | 162 | gctgctgatagtcgttgcgg | 72 | 4 |
| 323699 | Coding | NM_000875.2 | 167 | cttcagctgctgatagtcgt | 74 | 5 |
| 323700 | Coding | NM_000875.2 | 196 | ccctcgatcaccgtgcagtt | 56 | 6 |
| 323701 | Coding | NM_000875.2 | 223 | ttggagatgagcaggatgtg | 65 | 7 |
| 323702 | Coding | NM_000875.2 | 228 | cggccttggagatgagcagg | 66 | 8 |
| 323703 | Coding | NM_000875.2 | 233 | gtcctcggccttggagatga | 71 | 9 |
| 323704 | Coding | NM_000875.2 | 238 | cggtagtcctcggccttgga | 71 | 10 |
| 323705 | Coding | NM_000875.2 | 367 | ttgtagaagagtttccagcc | 52 | 11 |
| 323706 | Coding | NM_000875.2 | 396 | tggtcatctcgaagatgacc | 5 | 12 |
| 323707 | Coding | NM_000875.2 | 401 | gagattggtcatctcgaaga | 20 | 13 |
| 323708 | Coding | NM_000875.2 | 406 | tccttgagattggtcatctc | 41 | 14 |
| 323709 | Coding | NM_000875.2 | 411 | caatatccttgagattggtc | 29 | 15 |
| 323710 | Coding | NM_000875.2 | 416 | aagcccaatatccttgagat | 43 | 16 |
| 323711 | Coding | NM_000875.2 | 443 | cccccgagtaatgttcctca | 41 | 17 |
| 323712 | Coding | NM_000875.2 | 459 | tctcaatcctgatggcccc | 56 | 18 |
| 323713 | Coding | NM_000875.2 | 527 | gttattggacaccgcatcca | 31 | 19 |
| 323714 | Coding | NM_000875.2 | 532 | atgtagttattggacaccgc | 64 | 20 |
| 323715 | Coding | NM_000875.2 | 537 | ccacaatgtagttattggac | 65 | 21 |
| 323716 | Coding | NM_000875.2 | 571 | cacaggtccccacattcctt | 42 | 22 |
| 323717 | Coding | NM_000875.2 | 576 | ctggacacaggtccccacat | 45 | 23 |
| 323718 | Coding | NM_000875.2 | 616 | atggtggtcttctcacacat | 69 | 24 |
| 323719 | Coding | NM_000875.2 | 621 | tgttgatggtggtcttctca | 66 | 25 |
| 323720 | Coding | NM_000875.2 | 626 | ctcattgttgatggtggtct | 81 | 26 |
| 323721 | Coding | NM_000875.2 | 632 | gttgtactcattgttgatgg | 73 | 27 |
| 323722 | Coding | NM_000875.2 | 637 | cggtagttgtactcattgtt | 71 | 28 |
| 323723 | Coding | NM_000875.2 | 642 | agcagcggtagttgtactca | 70 | 29 |
| 323724 | Coding | NM_000875.2 | 647 | ggtccagcagcggtagttgt | 60 | 30 |
| 323725 | Coding | NM_000875.2 | 652 | tttgtggtccagcagcggta | 67 | 31 |
| 323726 | Coding | NM_000875.2 | 674 | tgggcacattttctggcagc | 57 | 32 |
| 323727 | Coding | NM_000875.2 | 1283 | ggagtaattcccttctagct | 21 | 33 |
| 323728 | Coding | NM_000875.2 | 1324 | tcccacagttgctgcaagtt | 73 | 34 |
| 323729 | Coding | NM_000875.2 | 1678 | atgttccagctgttggagcc | 72 | 35 |
| 323730 | Coding | NM_000875.2 | 1683 | ccaccatgttccagctgttg | 78 | 36 |
| 323731 | Coding | NM_000875.2 | 1750 | gtccagggcttcagcccatg | 74 | 37 |

TABLE 1-continued

| | | | | | | |
|---|---|---|---|---|---|---|
| 323732 | Coding | NM_000875.2 | 1786 | gtgagggtcacagccttgac | 59 | 38 |
| 323733 | Coding | NM_000875.2 | 1791 | ccatggtgagggtcacagcc | 78 | 39 |
| 323734 | Coding | NM_000875.2 | 1846 | ttggtgcgaatgtacaagat | 61 | 40 |
| 323735 | Coding | NM_000875.2 | 2029 | attttgtctttggagcagta | 65 | 41 |
| 323736 | Coding | NM_000875.2 | 2203 | aggaaattctcaaagactttt | 43 | 42 |
| 323737 | Coding | NM_000875.2 | 2290 | ctgcttcggctggacatggt | 84 | 43 |
| 323738 | Coding | NM_000875.2 | 2295 | tgttcctgcttcggctggac | 76 | 44 |
| 323739 | Coding | NM_000875.2 | 2368 | ctgctctcaaagaaagggta | 58 | 45 |
| 323740 | Coding | NM_000875.2 | 2373 | ccactctgctctcaaagaaa | 0 | 46 |
| 323741 | Coding | NM_000875.2 | 2378 | gttatccactctgctctcaa | 57 | 47 |
| 323742 | Coding | NM_000875.2 | 2383 | tccttgttatccactctgct | 58 | 48 |
| 323743 | Coding | NM_000875.2 | 2446 | ttgcagctgtggatatcgat | 53 | 49 |
| 323744 | Coding | NM_000875.2 | 2451 | cgtggttgcagctgtggata | 85 | 50 |
| 323745 | Coding | NM_000875.2 | 2456 | agcctcgtggttgcagctgt | 75 | 51 |
| 323746 | Coding | NM_000875.2 | 2461 | ttctcagcctcgtggttgca | 62 | 52 |
| 323747 | Coding | NM_000875.2 | 2466 | ccagcttctcagcctcgtgg | 85 | 53 |
| 323748 | Coding | NM_000875.2 | 2471 | gcagcccagcttctcagcct | 77 | 54 |
| 323749 | Coding | NM_000875.2 | 2476 | gcgctgcagcccagcttctc | 71 | 55 |
| 323750 | Coding | NM_000875.2 | 2578 | tttaaaaagatggagttttc | 8 | 56 |
| 323751 | Coding | NM_000875.2 | 2583 | gccactttaaaaagatggag | 77 | 57 |
| 323752 | Coding | NM_000875.2 | 2677 | tcctgtctggacacacattc | 66 | 58 |
| 323753 | Coding | NM_000875.2 | 2791 | aagaacacaggatctgtcca | 38 | 59 |
| 323754 | Coding | NM_000875.2 | 2796 | catagaagaacacaggatct | 33 | 60 |
| 323755 | Coding | NM_000875.2 | 2992 | ggaacgtacacatcagcagc | 36 | 61 |
| 323756 | Coding | NM_000875.2 | 3076 | actccttcatagaccatccc | 26 | 62 |
| 323757 | Coding | NM_000875.2 | 3301 | cggagataactttgagatc | 35 | 63 |
| 323758 | Coding | NM_000875.2 | 3306 | gagaccggagataactttg | 29 | 64 |
| 323759 | Coding | NM_000875.2 | 3478 | attttgactgtgaaatcttc | 13 | 65 |
| 323760 | Coding | NM_000875.2 | 3643 | gcgatctcccagaggacgac | 72 | 66 |
| 323761 | Coding | NM_000875.2 | 3870 | tgtagtagaaggagacctcc | 26 | 67 |
| 323762 | Coding | NM_000875.2 | 4000 | gccttgtgtcctgagtgtct | 84 | 68 |
| 323763 | Stop Codon | NM_000875.2 | 4139 | atccaaggatcagcaggtcg | 69 | 69 |
| 323764 | 3'UTR | NM_000875.2 | 4329 | gctgcttgcatattgaaaaa | 77 | 70 |
| 323765 | 3'UTR | NM_000875.2 | 4334 | aaaaagctgcttgcatattg | 74 | 71 |
| 323766 | 3'UTR | NM_000875.2 | 4366 | gcccatgtcagttaagggtt | 69 | 72 |
| 323767 | 3'UTR | NM_000875.2 | 4822 | ccagcgtgtctctcaaatgg | 84 | 73 |
| 323768 | Intron | NT_035325.2 | 62268 | ggagtttaaaggacagtgcc | 59 | 74 |
| 323769 | Exon: Intron Junction | NT_035325.2 | 280527 | catcactgacctctttctat | 0 | 75 |

TABLE 1-continued

| | mRNA and other sequences | |
|---|---|---|
| IGF-IR 5' (M69229) | 5' untranslated sequence of human IGF-IR plus promoter region | 76 |
| IGF-IR (NM000875) | Nucleotide sequence encoding human IGF-IR | 77 |
| DT1064 | Nucleotide sequence encoding IGF-IR C5 propyne antisense compound CAC AGU UGC UGC AAG[1] | 78 |
| 13920 | antisense oligonucleotide control to human H-ras | 79 |
| 18078 | antisense oligonucleotide control to human JNK | 80 |
| 15770 | antisense oligonucleotide control to mouse and rat c-raf | 81 |
| 161212 | PCR primer to hIGF-RI | 82 |
| 161214 | PCR primer to hIGF-RI | 83 |
| 161215 | PCR primer to hIGF-RI | 84 |

IGF-IR mRNA target region site and sequence targeted by exemplary antisense oligonucleotide compounds to the 5'UTR region in Seq ID97

| ISIS # | REGION | TARGET SEQ ID NO | TARGET SITE | SEQUENCE/DESCRIPTION | SEQ ID NO |
|---|---|---|---|---|---|
| 90454 | 5'UTR | Seq ID97 | 730 | tccgggtttgaaaatggagg | 85 |
| 90459 | 5'UTR | Seq ID97 | 931 | gaagactgagtttgagactt | 86 |
| 90460 | 5'UTR | Seq ID97 | 738 | tgaaaatggaggccgacgac | 87 |
| 90466 | 5'UTR | Seq ID97 | 266 | cggctgtgaccttcagcgag | 88 |
| 90468 | 5'UTR | Seq ID97 | 267 | ggctgtgaccttcagcgagc | 89 |
| 90469 | 5'UTR | Seq ID97 | 889 | tcggagtattgtttccttcg | 90 |
| 90475 | 5'UTR | Seq ID97 | 508 | gggggagccgctcattcatt | 91 |

| | mRNA, amino acid and other sequences | |
|---|---|---|
| | exemplified antisense strand | 92 |
| | exemplified sense strand | 93 |
| | PCR primer for hGAPDH | 94 |
| | PCR primer for hGAPDH | 95 |
| | PCR probe to hGAPDH | 96 |
| IGF-IR | Nucleotide Sequence of IGF-IR mRNA with the 3' untranslated region, coding region and 5' untranslated region constructed from M69229 and NM000875 | 97 |
| IGF-IR | 391 amino acid sequence of IGF-IR protein | 98 |
| 306064 | Negative Control ODN | 99 |

TABLE 1-continued

Antisense oligonucleotide compounds to human IGF-IR targeted to the 5'UTR region of SeqID97

| ISIS # | REGION | TARGET SEQ ID NO | TARGET SITE | SEQUENCE/DESCRIPTION | %INHIB | SEQ ID NO |
|---|---|---|---|---|---|---|
| 175292 | 5'UTR | Seq ID97 | 930 | agtctcaaactcagtcttcg | 78 | 100 |
| 175293 | 5'UTR | Seq ID97 | 42 | gttaatgctggtaaacaaga | 40 | 101 |
| 175294 | 5'UTR | Seq ID97 | 558 | gaagtccgggtcacaggcga | 77 | 102 |
| 175295 | 5'UTR | Seq ID97 | 29 | aacaagagccccagcctcgc | 76 | 103 |
| 175296 | 5'UTR | Seq ID97 | 38 | atgctggtaaacaagagccc | 57 | 104 |
| 175297 | 5'UTR | Seq ID97 | 37 | tgctggtaaacaagagcccc | 61 | 105 |
| 175298 | 5'UTR | Seq ID97 | 516 | ggagtcaaaatgaatgagcg | 74 | 106 |
| 175299 | 5'UTR | Seq ID97 | 665 | aatctgcctaggcgaggaaa | 78 | 107 |
| 175300 | 5'UTR | Seq ID97 | 36 | gctggtaaacaagagcccca | 54 | 108 |
| 175301 | 5'UTR | Seq ID97 | 671 | agcccaaatctgcctaggcg | 77 | 109 |
| 175302 | 5'UTR | Seq ID97 | 730 | cctccattttcaaacccgga | 93 | 110 |
| 175303 | 5'UTR | Seq ID97 | 260 | gaaggtcacagccgaggcga | 82 | 111 |
| 175304 | 5'UTR | Seq ID97 | 265 | tcgctgaaggtcacagccga | 76 | 112 |
| 175305 | 5'UTR | Seq ID97 | 410 | atccaggacacacacaaagc | 81 | 113 |
| 175306 | 5'UTR | Seq ID97 | 557 | aagtccgggtcacaggcgag | 54 | 114 |
| 175307 | 5'UTR | Seq ID97 | 931 | aagtctcaaactcagtcttc | 86 | 115 |
| 175308 | 5'UTR | Seq ID97 | 738 | gtcgtcggcctccattttca | 94 | 116 |
| 175309 | 5'UTR | Seq ID97 | 526 | gcagaaacgcggagtcaaaa | 72 | 117 |
| 175310 | 5'UTR | Seq ID97 | 429 | gcggcgagctccttcccaaa | 76 | 118 |
| 175311 | 5'UTR | Seq ID97 | 40 | taatgctggtaaacaagagc | 53 | 119 |
| 175312 | 5'UTR | Seq ID97 | 723 | tttcaaacccggagaggcag | 31 | 120 |
| 175313 | 5'UTR | Seq ID97 | 657 | taggcgaggaaaaacaagcc | 62 | 121 |
| 175314 | 5'UTR | Seq ID97 | 266 | ctcgctgaaggtcacagccg | 87 | 122 |
| 175315 | 5'UTR | Seq ID97 | 798 | gcagcggcccagggctcggc | 75 | 123 |
| 175316 | 5'UTR | Seq ID97 | 267 | gctcgctgaaggtcacagcc | 82 | 124 |
| 175317 | 5'UTR | Seq ID97 | 889 | cgaaggaaacaatactccga | 84 | 125 |
| 175318 | 5'UTR | Seq ID97 | 523 | gaaacgcggagtcaaaatga | 68 | 126 |
| 175319 | 5'UTR | Seq ID97 | 884 | gaaacaatactccgaagggc | 63 | 127 |
| 175320 | 5'UTR | Seq ID97 | 414 | ccaaatccaggacacacaca | 64 | 128 |
| 175321 | 5'UTR | Seq ID97 | 734 | tcggcctccattttcaaacc | 78 | 129 |
| 175322 | 5'UTR | Seq ID97 | 554 | tccgggtcacaggcgaggcc | 67 | 130 |
| 175323 | 5'UTR | Seq ID97 | 508 | aatgaatgagcggctccccc | 82 | 131 |
| 175324 | 5'UTR | Seq ID97 | 261 | tgaaggtcacagccgaggcg | 57 | 132 |
| 175325 | 5'UTR | Seq ID97 | 259 | aaggtcacagccgaggcgag | 55 | 133 |
| 175326 | 5'UTR | Seq ID97 | 415 | cccaaatccaggacacacac | 74 | 134 |

TABLE 1-continued

| 175327 | 5'UTR | Seq ID97 | 933 | acaagtctcaaactcagtct | 61 | 135 |
| 175328 | 5'UTR | Seq ID97 | 33  | ggtaaacaagagccccagcc | 64 | 136 |

[1]This is also an antisense compound to IGF1R. All C's and 3 s are C5 propynated in this compound

BRIEF DESCRIPTION OF THE FIGURES

FIGS. 1A(i)-1A(ii). Sequence-specific and dose-dependent suppression of IGF-IR mRNA expression in ATL1101-treated PC cell lines in vitro. FIG. 1A (i) shows the effect of ATL1101 (SEQ ID NO:125) in LNCaP cells in vitro and FIG. 1A (ii) shows the effect of ATL1101 in PC3 cells in vitro.

FIGS. 1B(i)-1B(ii) Sequence-specific and dose-dependent suppression of IGF-IR protein expression in ATL1101-treated PC cell lines in vitro. FIG. 1B (i) shows the effect of ATL1101 in LNCaP cells in vitro and FIG. 1B (ii) shows the effect of ATL1101 in PC3 cells in vitro.

FIGS. 2A and B shows the effect of ATL1101 in LNCaP cells and PC3 cells in FBS, respectively. FIG. 2C shows the effect of ATL1101 in LNCaP cells in CSS.

FIGS. 3A and B shows the effect of ATL1101 in LNCaP and PC3 cells in vitro, respectively.

FIGS. 4A(i)-(ii), 4B, and 4C(i)-(ii) Effect of ATL1101 treatment on LNCaP and PC3 cell cycle and apoptosis in vitro. FIGS. 4A (i) and 4A (ii) shows the effect of ATL1101 in LNCaP cells in FBS and CSS, respectively. FIG. 4C (i) and (ii) show the effect of ATL1101 on Cyclin D1, Cyclin E, p-Rb, Rb, and p27, in LNCaP and PC3 cells in vitro, respectively.

FIGS. 5A and B show the effect of ATL1101 treatment on LNCaP tumor volume and serum PSA, respectively. FIG. 5C shows the effect of ATL1101 treatment on PC3 tumor volume. FIG. 5D shows the effect of ATL1101 on PC3 xenograft tumor proteins. FIG. 5E shows the effect of saline (PBS), IGF-IR antisense oligonucleotide and control oligonucleotide treatment on PC3 tumour size after vs. before treatment, as a % growth ratio, in 7 individual animals.

FIG. 6. Representation of the deoxyribonucleotide sequence of the 5' untranslated region of the IGF-IR gene (M69229; SEQ ID NO:76) showing the location of targets for ISIS 175314 (SEQ ID NO:122), ISIS 175317 (SEQ ID NO:125) and ISIS 175323 (SEQ ID NO:131).

FIG. 7A shows the % of viable cells 72 hours after Paclitaxel treatment at the indicated concentrations. FIG. 7B shows the % of viable cells 72 hours after Paclitaxel treatment together with the indicated concentrations of ATL1101 or control oligodeoxynucleotide (ISIS 306064; SEQ ID NO:99) or oligofectamine (OTC). FIG. 7C shows the % of sub G0/G1 cells treated with 50 nM ATL1101 or control oligodeoxynucleotide and 1 or 2 nM Paclitaxel. FIG. 7D shows IGF-IRB and cleaved PARP protein levels after 50 nM ATL1101 or control oligodeoxynucleotide and 1 nM Paclitaxel.

FIG. 11A shows ATL1101 suppression of IGF-IR mRNA. FIG. 11B shows ATL1101 non suppression of insulin receptor IR-A and IR-B mRNA. FIG. 11C shows ATL1101 suppression of IGF-IRβ protein levels but not of IR-β protein.

DETAILED DESCRIPTION

Figure 2A:
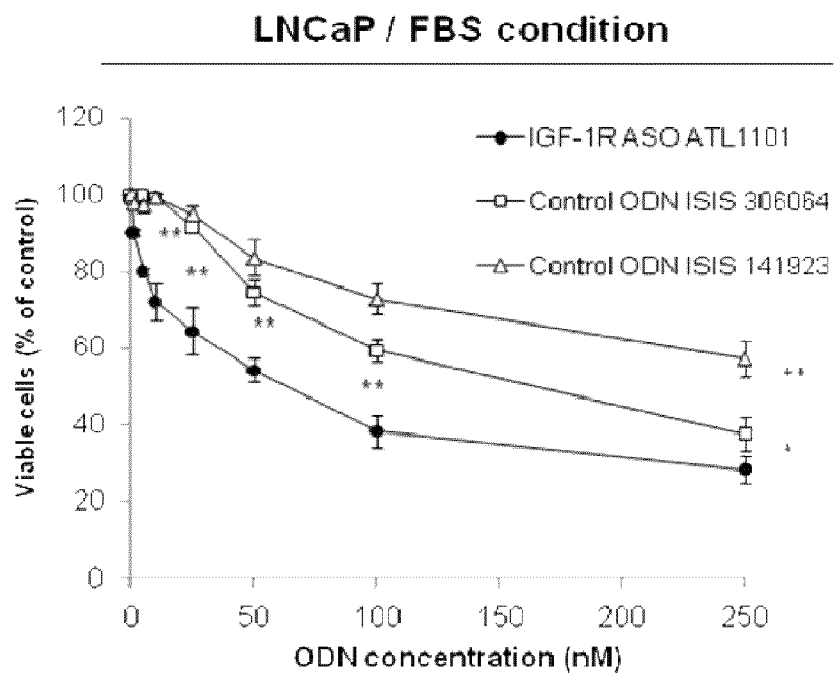
FIGS. 2A-C. Inhibition of growth in LNCaP and PC3 cells treated with ATL1101 in vitro.

The present invention provides compounds, compositions and methods for inhibiting expression of IGF-IR useful in the treatment of an IGF-IR positive tumor or cancer. As used herein, the term "treatment" refers to administering a pharmaceutical composition to effect an alteration or improvement of a disease, disorder, or condition.

In one embodiment, the present invention relates to the administration of antisense oligonucleotides which inhibit expression of IGF-IR, for example, second generation antisense gapmer oligonucleotides, including ISIS 175308, ISIS 175302, ISIS 175314, ISIS 175307, ISIS 175316, ISIS 175317 (ATL1101) and ISIS 175323, ISIS 323744, ISIS 323747, ISIS 323767, ISIS 323762 and ISIS 323737 in the treatment of a tumor or cancer. In one embodiment, the present invention relates to prostate tumor or prostate cancer.

In one embodiment the antisense oligonucleotides hybridize to nucleic acid molecules encoding the IGF-IR and act to reduce the size and/or growth of the tumor or cancer and/or delay progression of the tumor or cancer from androgen responsive/dependent to androgen unresponsive/independent. Tumor or cancer size and/or growth may be reduced, for example, by reducing the proliferation rate of the tumor/cancer cells, increasing the apoptotic rate of the tumor/cancer cells, modulating tumor/cancer cell signaling, chemosensitization, and/or inhibiting adhesion, anchorage, metastasis of the tumor/cancer cells and/or transformation of cells, for example, prostate cells. In a further embodiment, the antisense oligonucleotides may work by modulating, for example, angiogenesis, immune-inflammation or other pathological processes.

As used herein, the term "nucleic acid molecule encoding IGF-IR" is used interchangeably with "target nucleic acid" and encompasses DNA encoding IGF-IR, RNA (including pre-mRNA and mRNA or portions thereof) transcribed from such DNA, and further, cDNA derived from such RNA.

Hybridization of an oligonucleotide of the present invention with its target nucleic acid is generally referred to as "antisense". Hybridization of the oligonucleotide with its target nucleic acid inhibits the function of the target nucleic acid. Such "antisense inhibition" is typically based upon hydrogen bonding-based hybridization of the oligonucleotide to the target nucleic acid such that the target nucleic acid is cleaved, degraded, or otherwise rendered inoperable. The functions of target DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

"Hybridization" as used herein means pairing of complementary bases of the oligonucleotide and target nucleic acid. Base pairing typically involves hydrogen bonding, which may be Watson-Crick, Hoogsteen or reversed Hoogsteen hydrogen bonding, between complementary nucleoside or nucleotide bases (nucleobases). Guanine (G) and cytosine (C) are examples of complementary nucleobases which pair through the formation of 3 hydrogen bonds. Adenine (A) and thymine (T) are examples of complementary nucleobases which pair through the formation of 2 hydrogen bonds. Hybridization can occur under varying circumstances.

"Specifically hybridizable" and "complementary" are terms which are used to indicate a sufficient degree of complementarity such that stable and specific binding occurs between the oligonucleotide and target nucleic acid. It is understood that the oligonucleotide need not be 100% complementary to its target nucleic acid sequence to be specifically hybridizable. An oligonucleotide is specifically hybridizable when binding of the oligonucleotide to the target nucleic acid interferes with the normal function of the target molecule to cause a loss of activity, and there is a sufficient degree of complementarity to avoid non-specific binding of the oligonucleotide to non-target sequences under conditions in which specific binding is desired, for example, under physiological conditions in the case of therapeutic treatment.

In the present invention the phrase "stringent hybridization conditions" or "stringent conditions" refers to conditions under which the oligonucleotide will hybridize to its target sequence, but to a minimal number of other sequences. Stringent conditions are sequence-dependent and will be different in different circumstances. In the context of the present invention, "stringent conditions" under which the antisense oligonucleotide hybridizes to a target sequence is determined by the nature and composition of the antisense oligonucleotide and the assays in which it is being investigated.

"Complementary" as used herein, refers to the capacity for precise pairing between a nucleobase of the oligonucleotide and the target nucleic acid. For example, if a nucleobase at a certain position of the oligonucleotide is capable of hydrogen bonding with a nucleobase at a certain position of the target nucleic acid then the position of hydrogen bonding between the oligonucleotide and the target nucleic acid is considered to be a complementary position. The antisense oligonucleotide may hybridize over one or more segments such that intervening or adjacent segments are not involved in the hybridization event (e.g., a loop structure or hairpin structure). In one embodiment, the antisense oligonucleotides of the present invention comprise at least 70% sequence complementarity to a target region within the target nucleic acid. For example, an antisense compound in which 18 of 20 nucleobases of the antisense oligonucleotide are complementary to a target region within the target nucleic acid, and would therefore specifically hybridize, would represent 90% complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 non-complementary nucleobases which are flanked by 2 regions of complete complementarity with the target nucleic acid would have 77.8% overall complementarity with the target nucleic acid and would thus fall within the scope of the present invention. Percent complementarity of an antisense oligonucleotide with a region of a target nucleic acid can be determined routinely using BLAST programs (basic local alignment search tools) and PowerBLAST programs known in the art (Altschul et al., 1990; Zhang and Madden, 1997).

Antisense Oligonucleotides

The present invention provides antisense oligonucleotides for inhibiting expression of IGF-IR. Such antisense oligonucleotides are targeted to nucleic acids encoding IGF-IR.

As used herein, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for the target nucleic acid and increased stability in the presence of nucleases.

Antisense oligonucleotides of the invention include, for example, ribozymes, siRNA, external guide sequence (EGS) oligonucleotides, alternate splicers, primers, probes, and other oligonucleotides which hybridize to at least a portion of the target nucleic acid.

Antisense oligonucleotides of the invention may be administered in the form of single-stranded, double-stranded, circular or hairpin and may contain structural elements such as internal or terminal bulges or loops. Once administered, the antisense oligonucleotides of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

The introduction of double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Cae-*

*norhabditis elegans* (Guo and Kemphs, 1995). Montgomery et al. (1998) have shown that the primary interference effects of dsRNA are posttranscriptional. The post-transcriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., 1998). Recently, it has been shown that it is, in fact, the single-stranded RNA oligomers of antisense polarity of the dsRNAs which are the potent inducers of RNAi (Tijsterman et al., 2002).

In one embodiment the oligonucleotides of the present invention comprise from about 8 to 80 nucleobases (i.e., from about 8 to 80 linked nucleobases). One of ordinary skill in the art will appreciate that the invention embodies oligonucleotides of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In a further embodiment, the oligonucleotides of the present invention comprise from about 12 to 50 nucleobases in length. One having ordinary skill in the art will appreciate that this embodies oligonucleotides of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In a further embodiment, the oligonucleotides of the present invention comprise from about 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

In a further embodiment, the oligonucleotides of the present invention comprise 8 to 80 nucleobases in length and a stretch of at least eight (8) consecutive nucleobases selected from within the exemplified antisense oligonucleotides.

In a further embodiment, the oligonucleotides of the present invention comprise at least the 8 consecutive nucleobases from the 5'-terminus of one of the exemplified antisense oligonucleotides.

In a further embodiment, the oligonucleotides of the present invention comprise at least the 8 consecutive nucleobases from the 3'-terminus of one of the exemplified antisense oligonucleotides.

One having ordinary skill in the art armed with the antisense oligonucleotides exemplified herein will be able, without undue experimentation, to identify further antisense oligonucleotides useful in the methods of the present invention.

Exemplified oligonucleotides of the present invention are referred to herein by ISIS number or SEQ ID NO.

In one embodiment, the antisense oligonucleotide is selected from the group consisting of: ISIS 175308 (SEQ ID NO:116), ISIS 175302 (SEQ ID NO:110), ISIS 175314 (SEQ ID NO:122), ISIS 175307 (SEQ ID NO:115), ISIS 175316 (SEQ ID NO:124), ISIS 175317 (SEQ ID NO:125) and ISIS 175323 (SEQ ID NO:131).

In a further embodiment, the antisense oligonucleotide is selected form the group consisting of: ISIS 323737 (SEQ ID NO:43), ISIS 323744 (SEQ ID NO:50), ISIS 323747 (SEQ ID NO:53), ISIS 323767 (SEQ ID NO:73), and ISIS 323762 (SEQ ID NO:68).

In a further embodiment, the antisense oligonucleotide is ISIS 175317 (SEQ ID NO:125).

As will be understood by those skilled in the art a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound; however, linear compounds are generally preferred. In addition, linear compounds may have internal nucleobase complementarity and may therefore fold in a manner so as to produce a fully or partially double-stranded compound. With regard to oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Antisense oligonucleotides of the present invention include oligonucleotides having modified backbones or non-natural internucleoside linkages. Oligonucleotides having modified backbones include those that retain a phosphorus atom in the backbone and those that do not have a phosphorus atom in the backbone.

Modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage.

Oligonucleotides having inverted polarity comprise a single 3' to 3' linkage at the 3'-most internucleotide linkage, i.e., a single inverted nucleoside residue which may be a basic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. No. 3,687,808; U.S. Pat. No. 4,469,863; U.S. Pat. No. 4,476,301; U.S. Pat. No. 5,023,243; U.S. Pat. No. 5,177,196; U.S. Pat. No. 5,188,897; U.S. Pat. No. 5,264,423; U.S. Pat. No. 5,276,019; U.S. Pat. No. 5,278,302; U.S. Pat. No. 5,286,717; U.S. Pat. No. 5,321,131; U.S. Pat. No. 5,399,676; U.S. Pat. No. 5,405,939; U.S. Pat. No. 5,453,496; U.S. Pat. No. 5,455,233; U.S. Pat. No. 5,466,677; U.S. Pat. No. 5,476,925; U.S. Pat. No. 5,519,126; U.S. Pat. No. 5,536,821; U.S. Pat. No. 5,541,306; U.S. Pat. No. 5,550,111; U.S. Pat. No. 5,563,253; U.S. Pat. No. 5,571,799; U.S. Pat. No. 5,587,361; U.S. Pat. No. 5,194,599; U.S. Pat. No. 5,565,555; U.S. Pat. No. 5,527,899; U.S. Pat. No. 5,721,218; U.S. Pat. No. 5,672,697 and U.S. Pat. No. 5,625,050.

Modified oligonucleotide backbones that do not include a phosphorus atom therein include, for example, backbones formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleotides include, but are not limited to, U.S. Pat. No. 5,034,506; U.S. Pat. No. 5,166,315; U.S. Pat. No. 5,185,444; U.S. Pat. No. 5,214,134; U.S. Pat. No. 5,216,141; U.S. Pat. No. 5,235,033; U.S. Pat. No. 5,264,562; U.S. Pat. No. 5,264,564; U.S. Pat. No. 5,405,938; U.S. Pat. No. 5,434,257; U.S. Pat. No. 5,466,677; U.S. Pat. No. 5,470,967; U.S. Pat. No. 5,489,677; U.S. Pat. No. 5,541,307; U.S. Pat. No. 5,561,225; U.S. Pat. No. 5,596,086; U.S. Pat. No. 5,602,240; U.S. Pat. No. 5,610,289; U.S. Pat. No. 5,602,240; U.S. Pat. No. 5,608,046; U.S. Pat. No. 5,610,289; U.S. Pat. No. 5,618,704; U.S. Pat. No. 5,623,070; U.S. Pat. No. 5,663,312; U.S. Pat. No. 5,633,360; U.S. Pat. No. 5,677,437; U.S. Pat. No. 5,792,608; U.S. Pat. No. 5,646,269 and U.S. Pat. No. 5,677,439.

Modified Sugar and Internucleoside Linkages

Antisense oligonucleotides of the present invention include oligonucleotide mimetics where both the sugar and the internucleoside linkage (i.e. the backbone), of the nucleotide units are replaced with novel groups. The nucleobase units are maintained for hybridization with the target nucleic acid.

An oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. No. 5,539,082; U.S. Pat. No. 5,714,331; and U.S. Pat. No. 5,719,262. Further teaching of PNA compounds can be found in Nielsen et al., 1991.

The antisense oligonucleotides of the present invention also include oligonucleotides with phosphorothioate backbones and oligonucleotides with heteroatom backbones, for example, —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N ($CH_3$)—N($CH_3$)—$CH_2$— and —O—N($CH_3$)—$CH_2$—$CH_2$- [wherein the native phosphodiester backbone is represented as —O—P—O—$CH_2$—] of U.S. Pat. No. 5,489,677, and the amide backbones of U.S. Pat. No. 5,602,240.

The antisense oligonucleotides of the present invention also include oligonucleotides having morpholino backbone structures of U.S. Pat. No. 5,034,506.

Modified Sugars

Modified oligonucleotides may also contain one or more substituted sugar moieties.

Examples of modified oligonucleotides include oligonucleotides comprising one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl.

In one embodiment the oligonucleotide comprises one of the following at the 2' position: $O[(CH_2)_nO]_mCH_3$, $O(CH_2)$—$OCH_3$, $O(CH_2)$—$NH_2$, $O(CH_2)$—$CH_3$, $O(CH_2)$—$ONH_2$, and $O(CH_2)_nON[(CH_2)_nCH_3]_2$, where n and m are from 1 to about 10.

Further examples include of modified oligonucleotides include oligonucleotides comprising one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

In one embodiment the modification includes 2'-methoxyethoxy (2'-O—$CH_2CH_2OCH_3$, also known as 2'-O-(2-methoxyethyl) or 2'-MOE) (Martin et al., 1995), i.e., an alkoxyalkoxy group. In a further embodiment the modification includes 2'-dimethylaminooxyethoxy, i.e., a $O(CH_2)_2ON$ $(CH_3)_2$ group, also known as 2'-DMAOE, and 2'-dimethylaminoethoxyethoxy (also known in the art as 2'-O-dimethylamino-ethoxy-ethyl or 2'-DMAEOE), i.e., 2'-O—$CH_2$—O—$CH_2$—N($CH_3$)$_2$.

Other modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. In one embodiment a 2'-arabino modification is 2'-F.

Similar modifications may also be made at other positions on the oligonucleotide, particularly the 3' position of the sugar on the 3' terminal nucleotide or in 2'-5' linked oligonucleotides and the 5' position of 5' terminal nucleotide.

Oligonucleotides may also have sugar mimetics such as cyclobutyl moieties in place of the pentofuranosyl sugar.

Representative United States patents that teach the preparation of such modified sugar structures include, but are not limited to, U.S. Pat. No. 4,981,957; U.S. Pat. No. 5,118,800; U.S. Pat. No. 5,319,080; U.S. Pat. No. 5,359,044; U.S. Pat. No. 5,393,878; U.S. Pat. No. 5,446,137; U.S. Pat. No. 5,466,786; U.S. Pat. No. 5,514,785; U.S. Pat. No. 5,519,134; U.S. Pat. No. 5,567,811; U.S. Pat. No. 5,576,427; U.S. Pat. No. 5,591,722; U.S. Pat. No. 5,597,909; U.S. Pat. No. 5,610,300; U.S. Pat. No. 5,627,053; U.S. Pat. No. 5,639,873; U.S. Pat. No. 5,646,265; U.S. Pat. No. 5,658,873; U.S. Pat. No. 5,670,633; U.S. Pat. No. 5,792,747; and U.S. Pat. No. 5,700,920.

A further modification of the sugar includes Locked Nucleic Acids (LNAs) in which the 2'-hydroxyl group is linked to the 3' or 4' carbon atom of the sugar ring, thereby forming a bicyclic sugar moiety. In one embodiment, the linkage is a methylene (—$CH_2$—)$_n$ group bridging the 2' oxygen atom and the 4' carbon atom wherein n is 1 or 2. LNAs and preparation thereof are described in WO 98/39352 and WO 99/14226.

Natural and Modified Nucleobases

Oligonucleotides may also include nucleobase modifications or substitutions. As used herein, "unmodified" or "natural" nucleobases include the purine bases adenine (A) and guanine (G), and the pyrimidine bases thymine (T), cytosine (C) and uracil (U).

Modified nucleobases include other synthetic and natural nucleobases such as, for example, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as, for example, a substituted phenoxazine cytidine (e.g., 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one).

Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., 1991, and those disclosed by Sanghvi, Y. S., Chapter 15, *Antisense Research and Applications*, pages 289-302, Crooke, S. T. and Lebleu, B., ed., CRC Press, 1993.

Certain of these nucleobases are particularly useful for increasing the binding affinity of the oligonucleotide. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. In one embodiment, these nucleobase substitutions are combined with 2'-O-methoxyethyl sugar modifications.

Representative United States patents that teach the preparation of certain of the above noted modified nucleobases as well as other modified nucleobases include, but are not limited to, U.S. Pat. No. 3,687,808, U.S. Pat. No. 4,845,205; U.S. Pat. No. 5,130,302; U.S. Pat. No. 5,134,066; U.S. Pat. No. 5,175,273; U.S. Pat. No. 5,367,066; U.S. Pat. No. 5,432,272; U.S. Pat. No. 5,457,187; U.S. Pat. No. 5,459,255; U.S. Pat. No. 5,484,908; U.S. Pat. No. 5,502,177; U.S. Pat. No. 5,525,711; U.S. Pat. No. 5,552,540; U.S. Pat. No. 5,587,469; U.S. Pat. No. 5,594,121, U.S. Pat. No. 5,596,091; U.S. Pat. No. 5,614,617; U.S. Pat. No. 5,645,985; U.S. Pat. No. 5,830,653; U.S. Pat. No. 5,763,588; U.S. Pat. No. 6,005,096; U.S. Pat. No. 5,681,941 and U.S. Pat. No. 5,750,692.

Conjugates

Another modification of the antisense oligonucleotide of the present invention involves chemically linking to the oligonucleotide one or more moieties or conjugates which enhance the activity, cellular distribution or cellular uptake of the antisense oligonucleotide. These moieties or conjugates can include conjugate groups covalently bound to functional groups such as primary or secondary hydroxyl groups.

Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes.

Groups that enhance the pharmacodynamic properties, in the context of this invention, include groups that improve uptake, enhance resistance to degradation, and/or strengthen sequence-specific hybridization with the target nucleic acid.

Groups that enhance the pharmacokinetic properties, in the context of this invention, include groups that improve uptake, distribution, metabolism or excretion of the compounds of the present invention.

Representative conjugate groups are disclosed in PCT/US92/09196 and U.S. Pat. No. 6,287,860.

Conjugate moieties include but are not limited to lipid moieties such as a cholesterol moiety, cholic acid, a thioether, for example, hexyl-5-tritylthiol, a thiocholesterol, an aliphatic chain, for example, dodecandiol or undecyl residues, a phospholipid, for example, di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

Antisense oligonucleotides of the invention may also be conjugated to active drug substances.

Oligonucleotide-drug conjugates and their preparation are described in U.S. Ser. No. 09/334,130.

Representative United States patents that teach the preparation of such oligonucleotide conjugates include, but are not limited to, U.S. Pat. No. 4,828,979; U.S. Pat. No. 4,948,882; U.S. Pat. No. 5,218,105; U.S. Pat. No. 5,525,465; U.S. Pat. No. 5,541,313; U.S. Pat. No. 5,545,730; U.S. Pat. No. 5,552,538; U.S. Pat. No. 5,578,717, U.S. Pat. No. 5,580,731; U.S. Pat. No. 5,580,731; U.S. Pat. No. 5,591,584; U.S. Pat. No. 5,109,124; U.S. Pat. No. 5,118,802; U.S. Pat. No. 5,138,045; U.S. Pat. No. 5,414,077; U.S. Pat. No. 5,486,603; U.S. Pat. No. 5,512,439; U.S. Pat. No. 5,578,718; U.S. Pat. No. 5,608,046; U.S. Pat. No. 4,587,044; U.S. Pat. No. 4,605,735; U.S. Pat. No. 4,667,025; U.S. Pat. No. 4,762,779; U.S. Pat. No. 4,789,737; U.S. Pat. No. 4,824,941; U.S. Pat. No. 4,835,263; U.S. Pat. No. 4,876,335; U.S. Pat. No. 4,904,582; U.S. Pat. No. 4,958,013; U.S. Pat. No. 5,082,830; U.S. Pat. No. 5,112,963; U.S. Pat. No. 5,214,136; U.S. Pat. No. 5,082,830; U.S. Pat. No. 5,112,963; U.S. Pat. No. 5,214,136; U.S. Pat. No. 5,245,022; U.S. Pat. No. 5,254,469; U.S. Pat. No. 5,258,506; U.S. Pat. No. 5,262,536; U.S. Pat. No. 5,272,250; U.S. Pat. No. 5,292,873; U.S. Pat. No. 5,317,098; U.S. Pat. No. 5,371,241, U.S. Pat. No. 5,391,723; U.S. Pat. No. 5,416,203, U.S. Pat. No. 5,451,463; U.S. Pat. No. 5,510,475; U.S. Pat. No. 5,512,667; U.S. Pat. No. 5,514,785; U.S. Pat. No. 5,565,552; U.S. Pat. No. 5,567,810; U.S. Pat. No. 5,574,142; U.S. Pat. No. 5,585,481; U.S. Pat. No. 5,587,371; U.S. Pat. No. 5,595,726; U.S. Pat. No. 5,597,696; U.S. Pat. No. 5,599,923; U.S. Pat. No. 5,599,928 and U.S. Pat. No. 5,688,941.

Chimeric Compounds

As would be appreciated by those skilled in the art, it is not necessary for all positions in a given compound to be uniformly modified, and in fact more than one of the aforementioned modifications may be incorporated in a single oligonucleotide or even at a single nucleoside within an oligonucleotide.

Antisense oligonucleotides of the invention also include chimeric oligonucleotides. "Chimeric oligonucleotides" contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, and/or oligonucleotide mimetics as described above. Such compounds have also been referred to in the art as hybrids or gapmers.

Representative United States patents that teach the preparation of such hybrid structures include, but are not limited to, U.S. Pat. No. 5,013,830; U.S. Pat. No. 5,149,797; U.S. Pat. No. 5,220,007; U.S. Pat. No. 5,256,775; U.S. Pat. No. 5,366,878; U.S. Pat. No. 5,403,711; U.S. Pat. No. 5,491,133; U.S. Pat. No. 5,565,350; U.S. Pat. No. 5,623,065; U.S. Pat. No. 5,652,355; U.S. Pat. No. 5,652,356; and U.S. Pat. No. 5,700,922.

Oligonucleotide Compositions

The oligonucleotides of the present invention are administered systemically. As used herein "systemic administration" is a route of administration that is either enteral or parenteral.

As used herein "enteral" refers to any form of administration that involves any part of the gastrointestinal tract and includes oral administration of, for example, the antisense oligonucleotide in tablet, capsule or drop form; gastric feeding tube, duodenal feeding tube, or gastrostomy; and rectal administration of, for example, the antisense oligonucleotide in suppository or enema form.

As used herein "parenteral" includes administration by injection or infusion. Examples include, intravenous (into a vein), intraarterial (into an artery), intramuscular (into a muscle), intracardiac (into the heart), subcutaneous (under the skin), intraosseous infusion (into the bone marrow), intradermal, (into the skin itself), intrathecal (into the spinal canal), intraperitoneal (infusion or injection into the peritoneum), intravesical (infusion into the urinary bladder). transdermal (diffusion through the intact skin), transmucosal (diffusion through a mucous membrane), inhalational.

The oligonucleotides of the invention may be admixed, encapsulated, conjugated or otherwise associated with other molecules, molecule structures or mixtures of compounds, as for example, liposomes, receptor-targeted molecules (for example, a monoclonal antibody to the IGF-IR), oral, rectal, topical or other formulations, for assisting in uptake, distribution and/or absorption.

Representative United States patents that teach the preparation of such uptake, distribution and/or absorption-assisting formulations include, but are not limited to, U.S. Pat. No. 5,108,921; U.S. Pat. No. 5,354,844; U.S. Pat. No. 5,416,016; U.S. Pat. No. 5,459,127; U.S. Pat. No. 5,521,291; U.S. Pat. No. 5,543,158; U.S. Pat. No. 5,547,932; U.S. Pat. No. 5,583,020; U.S. Pat. No. 5,591,721; U.S. Pat. No. 4,426,330; U.S. Pat. No. 4,534,899; U.S. Pat. No. 5,013,556; U.S. Pat. No. 5,108,921; U.S. Pat. No. 5,213,804; U.S. Pat. No. 5,227,170; U.S. Pat. No. 5,264,221; U.S. Pat. No. 5,356,633; U.S. Pat. No. 5,395,619; U.S. Pat. No. 5,416,016; U.S. Pat. No. 5,417,978; U.S. Pat. No. 5,462,854; U.S. Pat. No. 5,469,854; U.S. Pat. No. 5,512,295; U.S. Pat. No. 5,527,528; U.S. Pat. No. 5,534,259; U.S. Pat. No. 5,543,152; U.S. Pat. No. 5,556,948; U.S. Pat. No. 5,580,575; and U.S. Pat. No. 5,595,756.

The antisense oligonucleotides of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the antisense oligonucleotides of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510, WO 94/26764 and U.S. Pat. No. 5,770,713.

The term "pharmaceutically acceptable salts" refers to physiologically and pharmaceutically acceptable salts of the compounds of the invention, i.e., salts that retain the desired biological activity of the parent compound and do not impart undesired toxicological effects thereto. For oligonucleotides, examples of pharmaceutically acceptable salts and their uses are further described in U.S. Pat. No. 6,287,860.

Target Nucleic Acid

"Targeting" an antisense oligonucleotide to a particular nucleic acid, in the context of this invention, can be a multi-step process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes IGF-IR.

The targeting process usually also includes determination of at least one target region, segment, or site within the target nucleic acid for the antisense interaction to occur such that the desired effect, for example, inhibition of expression, will result. Within the context of the present invention, the term "region" is defined as a portion of the target nucleic acid having at least one identifiable structure, function, or characteristic. Within regions of the target nucleic acids are segments. "Segments" are defined as smaller or sub-portions of regions within a target nucleic acid. "Sites" as used herein means positions within the target nucleic acid.

Since the translation initiation codon is typically 5'-AUG (in transcribed mRNA molecules; 5'-ATG in the corresponding DNA molecule), the translation initiation codon is also referred to as the "AUG codon", the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding IGF-IR, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such a mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense oligonucleotides of the present invention.

The open reading frame (ORF) or "coding region", which is known in the art to refer to the region between the translation initiation codon and the translation termination codon, is also a region which may be targeted effectively. In one embodiment, the intragenic region encompassing the translation initiation or termination codon of the open reading frame (ORF) of a gene is targeted.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. In one embodiment, the 5' cap region is targeted.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense oligonucleotides targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. In one embodiment, the types of variants described herein are targeted.

The locations on the target nucleic acid to which the exemplified antisense oligonucleotides hybridize are hereinbelow referred to as "target segments". As used herein the term "target segment" is defined as at least an 8-nucleobase portion of a target region to which an antisense oligonucleotide is targeted. While not wishing to be bound by theory, it is presently believed that these target segments represent portions of the target nucleic acid which are accessible for hybridization.

While the specific sequences of target segments are set forth herein, one of skill in the art will recognize that these serve to illustrate and describe particular embodiments within the scope of the present invention. Additional target segments may be identified by one having ordinary skill.

In one embodiment, target segments include DNA or RNA sequences that comprise at least the 8 consecutive nucleobases from the 5'-terminus of one of the exemplified target segments.

In a further embodiment, target segments include DNA or RNA sequences that comprise at least the 8 consecutive nucleobases from the 3'-terminus of one of the exemplified target segments.

One having ordinary skill in the art armed with the target segments exemplified herein will be able, without undue experimentation, to identify further target segments.

Once one or more target regions, segments or sites have been identified, antisense oligonucleotides are chosen which are sufficiently complementary to the target, i.e., hybridize sufficiently well and with sufficient specificity, to give the desired effect.

In a further embodiment, the "target segments" identified herein may be employed in a screen for additional compounds that modulate the expression of the IGF-IR gene. "Modulators" are those compounds that decrease or increase the expression of a nucleic acid molecule encoding IGF-IR and which comprise at least a 8 nucleobase portion which is complementary to the target segment.

The screening method comprises the steps of contacting a target segment of the nucleic acid encoding IGF-IR with one or more candidate modulators, and selecting for one or more candidate modulators which decrease or increase the expression of a nucleic acid encoding IGF-IR. Once it is shown that the candidate modulator or modulators are capable of modulating (e.g., either decreasing or increasing) the expression of a nucleic acid encoding IGF-IR, the modulator may then be employed in further investigative studies of the function of IGF-IR, or for use as a research, diagnostic, or therapeutic agent in accordance with the present invention.

The target segments of the present invention may also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., 1998; Timmons and Fire, 1998; Timmons et al., 2001; Tabara et al., 1998; Montgomery et al., 1998; Tuschl et al., 1999; Elbashir et al., 2001a; Elbashir et al., 2001b). For example, such double-stranded moieties have been shown to inhibit the target by the classical hybridization of antisense strand of the duplex to the target, thereby triggering enzymatic degradation of the target (Tijsterman et al., 2002).

Diagnostics, Therapeutics, Prophylaxis, Research Reagents and Kits

The oligonucleotides of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the oligonucleotides of the present invention, either alone or in combination with other compounds or therapeutics, can be used as tools in differential and/or combinatorial analyses to elucidate expression patterns of a portion or the entire complement of genes expressed within cells and tissues.

As one non-limiting example, expression patterns within cells or tissues treated with one or more antisense oligonucleotides are compared to control cells or tissues not treated with antisense oligonucleotides and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, 2000; Celis et al., 2000), SAGE (serial analysis of gene expression)(Madden et al., 2000), READS (restriction enzyme amplification of digested cDNAs) (Prashar and Weissman, 1999), TOGA (total gene expression analysis) (Sutcliffe et al., 2000), protein arrays and proteomics (Celis et al. 2000; Jungblut et al., 1999), expressed sequence tag (EST) sequencing (Celis et al., 2000; Larsson et al., 2000), subtractive RNA fingerprinting (SuRF) (Fuchs et al., 2000; Larson et al., 2000), subtractive cloning, differential display (DD) (Jurecic and Belmont, 2000), comparative genomic hybridization (Carulli et al., 1998), FISH (fluorescent in situ hybridization) techniques (Going and Gusterson, 1999) and mass spectrometry methods (To, 2000).

The oligonucleotides of the invention are useful for research and diagnostics, because the oligonucleotides hybridize to nucleic acids encoding IGF-IR. For example, oligonucleotides that are shown to hybridize with such efficiency and under such conditions as disclosed herein as to be effective IGF-IR inhibitors of IGF-IR gene expression inhibitors will also be effective primers or probes under conditions favoring gene amplification or detection, respectively. These primers and probes are useful in methods requiring the specific detection of nucleic acid molecules encoding IGF-IR and in the amplification of said nucleic acid molecules for detection or for use in further studies of IGF-IR or its gene. Hybridization of the antisense oligonucleotides, particularly the primers and probes, of the invention with a nucleic acid encoding IGF-IR can be detected by means known in the art. Such means may include conjugation of an enzyme to the oligonucleotide, radiolabeling of the oligonucleotide or any other suitable detection means. Kits using such detection means for detecting the level of IGF-IR in a sample may also be prepared.

For therapeutics, an animal, preferably a human, suspected of having, for example, a prostatic disorder which can be treated by modulating the expression of the IGF-IR gene is treated by systemically administering antisense oligonucleotides in accordance with the present invention.

For example, in one non-limiting embodiment, the methods comprise the step of administering to the animal in need of treatment, a therapeutically effective amount of an antisense oligonucleotide which inhibits expression of IGF-IR. The antisense oligonucleotide may effectively inhibit the activity of the IGF-IR protein or inhibit the expression of the IGF-IR gene. In one embodiment, the activity or expression of IGF-IR or its gene in an animal is inhibited by about 10%. In a further embodiment, the activity or expression of IGF-IR or its gene in an animal is inhibited by about 30%. In a further embodiment, the activity or expression of IGF-IR or its gene in an animal is inhibited by 50% or more.

For example, the reduction of the expression of the IGF-IR gene may be measured in serum, adipose tissue, skin cells, liver or any other body fluid, tissue or organ of the animal. In one embodiment, the cells contained within said fluids, tissues or organs being analyzed contain a nucleic acid molecule encoding an IGF-IR protein. In a further embodiment, the reduction of the expression of the IGF-IR gene is measured in human prostate cells, BPH prostate cells, and/or prostate cancer cells.

The oligonucleotides of the invention can be utilized in pharmaceutical compositions by adding an effective amount of a compound to a suitable pharmaceutically acceptable diluent or carrier. Use of the compounds and methods of the invention may also be useful prophylactically.

For treatment of an androgen sensitive tumor or cancer, the therapeutic compositions of the invention are suitably administered before, at about the same time or after initiation of androgen withdrawal. Initiation of androgen withdrawal may be accomplished via surgical (orichiectomy—removal of both testicles) or chemical (drug-induced suppression of testosterone) castration. Chemical castration can be achieved by various regimens, including administration of one or more luteinizing hormone-releasing hormone antagonists, luteinizing hormone-releasing hormone agonists and/or anti-androgens. Inhibition of IGF-IR expression can be used to delay progression of the tumor or cancer from androgen responsive/dependent to androgen unresponsive/independent.

The method for treating a tumor or cancer, including prostate cancer, in accordance with the invention may further include administration of chemotherapeutic agents and/or additional antisense oligonucleotides directed at different targets. Examples of other therapy agents include, without limitation, taxanes (Paclitaxel or Docetaxel), mitoxanthrone, and antisense oligonucleotides directed to Bcl-2, Bcl-xl or c-myc.
Enhancing the Sensitivity of an IGF-IR Positive Tumor or Cancer Cell to a Taxane Based Agent The present invention also provides a method for enhancing the sensitivity of an IGF-IR positive tumor or cancer cell to a taxane based agent. The "sensitivity" of the tumor or cancer cell to a taxane based agent is the susceptibility of the cell to the inhibitory and/or cytotoxic effect of the taxane based agent. For example, sensitivity of a tumor or cancer cell to a taxane based agent is indicated by reduction in growth rate and/or cell viability and/or an increase in apoptosis of the cell in response to the taxane based agent. The sensitivity may also be demonstrated by a reduction of the symptoms caused by the tumor or cancer cell(s). The sensitivity of a tumor or cancer cell to a taxane based agent can be determined by established methods in the art.

Agents that Inhibit Expression of IGF-IR

In addition to antisense oligonucleotides such as those described above, the agent that inhibits expression of IGF-IR may be, for example, a small interfering RNA, a microRNA, a catalytic polynucleotide, a small molecule inhibitor or antagonist, a peptide inhibitor or antagonist, a polypeptide like binding protein, a soluble form of IGF-I or IGF-II, a soluble form of the IGF-IR or IGF-IIR, or an antibody or an antigenic binding fragment thereof. Examples of some of these agents are described in detail below.

RNA Interference

RNA interference (RNAi) is particularly useful for specifically inhibiting the production of a particular protein. Although not wishing to be limited by theory, Waterhouse et al. (1998) have provided a model for the mechanism by which dsRNA (duplex RNA) can be used to reduce protein production. This technology relies on the presence of dsRNA molecules that contain a sequence that is essentially identical to the mRNA of the gene of interest or part thereof, in this case an mRNA encoding IGF-IR. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present invention is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology to the target gene to be inactivated. The DNA therefore comprises both sense and antisense sequences that, when transcribed into RNA, can hybridize to form the double stranded RNA region. In one embodiment of the invention, the sense and antisense sequences are separated by a spacer region that comprises an intron which, when transcribed into RNA, is spliced out. This arrangement has been shown to result in a higher efficiency of gene silencing. The double stranded region may comprise one or two RNA molecules, transcribed from either one DNA region or two. The presence of the double stranded molecule is thought to trigger a response from an endogenous mammalian system that destroys both the double stranded RNA and also the homologous RNA transcript from the target mammalian gene, efficiently reducing or eliminating the activity of the target gene.

The length of the sense and antisense sequences that hybridize should each be at least 19 contiguous nucleotides. The full-length sequence corresponding to the entire gene transcript may be used. The degree of identity of the sense and antisense sequences to the targeted transcript should be at least 85%, at least 90%, or at least 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ("siRNA") molecules comprise a nucleotide sequence that is identical to about 19-21 contiguous nucleotides of the target mRNA. Preferably, the siRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the mammal in which it is to be introduced, for example as determined by standard BLAST search.

microRNA

MicroRNA regulation is a specialized branch of the RNA silencing pathway that evolved towards gene regulation, diverging from conventional RNAi/PTGS. MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released microRNAs are incorporated into RISC-like complexes containing a particular subset of Argonaute proteins that exert sequence-specific gene repression (see, for example, Millar and Waterhouse, 2005; Pasquinelli et al., 2005; Almeida and Allshire, 2005).

Catalytic Polynucleotides

The term "catalytic polynucleotide" refers to a DNA molecule or DNA-containing molecule (also known in the art as a "deoxyribozyme") or an RNA or RNA-containing molecule (also known as a "ribozyme") which specifically recognizes a distinct substrate and catalyses the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are particularly useful in this invention are hammerhead ribozymes (Haseloff and Gerlach, 1988; Perriman et al., 1992) and hairpin ribozymes (Zolotukiin et al., 1996; Klein et al., 1998; Shippy et al., 1999).

The ribozymes of this invention and DNA encoding the ribozymes can be chemically synthesized using methods well known in the art. The ribozymes can also be prepared from a DNA molecule (that upon transcription, yields an RNA molecule) operably linked to an RNA polymerase promoter, for example, the promoter for T7 RNA polymerase or SP6 RNA polymerase. Accordingly, also provided by this invention is a nucleic acid molecule, that is, DNA or cDNA, coding for a catalytic polynucleotide of the invention. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase.

As with antisense oligonucleotides, small interfering RNA and microRNA described herein, catalytic polynucleotides of the invention should be capable of "hybridizing" the target nucleic acid molecule under "physiological conditions", namely those conditions within a tumor or cancer cell.
Antibodies As used herein, the term "antibody" refers to an immunoglobulin molecule capable of binding to a target protein and/or an epitope thereof and/or an immunogenic fragment thereof and/or a modified form thereof (e.g., glycosylated, etc.) through at least one antigen binding site, located in the variable region of the immunoglobulin molecule. This term encompasses not only intact polyclonal or monoclonal antibodies, but also variants, fusion proteins comprising an antibody portion with an antigen binding site of the required specificity, humanized antibodies, human antibodies, chimeric antibodies, and any other modified configuration of binding domains of an immunoglobulin molecule that comprises an antigen binding site of the required specificity, for example, a diabody, triabody, tetrabody or multi-specific antibody fragment. This term also encompasses derivatives comprising said antibodies or antigen binding domains, for example, conjugates comprising an additional component, for example, a toxin and/or a compound that increases the stability of an antibody or antigen binding domain.

As used herein, the term "antigen binding domain" shall be taken to mean any fragment or domain of an antibody that retains the ability to bind to the target protein, preferably specifically or selectively. This term also includes a polypeptide comprising a plurality of antigen binding domains of an antibody and/or a plurality of antigen binding domains wherein a domain is from one antibody and another domain is from another antibody. This term includes a Fab fragment, a Fab' fragment, a F(ab') fragment, a single chain antibody (SCA or SCAB) amongst others.

A "Fab fragment" consists of a monovalent antigen-binding fragment of an antibody molecule, and can be produced by digestion of a whole antibody molecule with the enzyme papain, to yield a fragment consisting of an intact light chain and a portion of a heavy chain. Such fragments can also be produced using recombinant means.

A "Fab' fragment" of an antibody molecule can be obtained by treating a whole antibody molecule with pepsin, followed by reduction, to yield a molecule consisting of an intact light chain and a portion of a heavy chain.

Two Fab' fragments are obtained per antibody molecule treated in this manner. Such fragments can also be produced using recombinant means.

A "F(ab')$_2$ fragment" of an antibody consists of a dimer of two Fab' fragments held together by two disulfide bonds, and is obtained by treating a whole antibody molecule with the enzyme pepsin, without subsequent reduction.

Such fragments can also be produced using recombinant means.

A "scFv fragment" is a genetically engineered fragment containing the variable region of a light chain and the variable region of a heavy chain expressed as two chains.

A "single chain antibody" (SCA) is a genetically engineered single chain molecule containing the variable region of a light chain and the variable region of a heavy chain, linked by a suitable, flexible polypeptide linker. This term also encompasses domain antibodies (dAbs) comprising a single variable domain, a heavy chain only antibody (e.g., from camelid or cartilaginous fish) or a minibody or a flex minibody or an antigen binding domain discussed above fused to a constant region of an antibody or a Fc region of an antibody or a $C_H2$ and/or $C_H3$ region of an antibody.

Methods of producing antibodies and antigenic binding fragments thereof are well known in the art.

EXAMPLES

Example 1

Synthesis of Nucleoside Phosphoramidites

The following compounds, including amidites and their intermediates were prepared as described in U.S. Pat. No. 6,426,220 and WO 02/36743: -Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-N$^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N$^4$-benzoyl-5-methyl-cytidine penultimate intermediate, [5'-O-(4,4'-Dimethoxytriphenylmethyl)-2'-O-(2-methoxyethyl)-N$^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-N$^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-N$^4$-isobutyrylguanosin-3'-O-yl]-2-cyanoethyl-N,N-diisopropylphosphoramidite (MOE G amidite), 2'-O-(Aminooxyethyl) nucleoside amidites and 2'-β-(dimethylaminooxyethyl) nucleoside amidites, 2'-(Dimethylaminooxyethoxy) nucleoside amidites, 5'-O-tert-Butyldiphenylsilyl-O$^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O—[N,N-dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O—[2(2-N,N-dimethylaminoethoxy)ethyl]-5-methyl uridine, 5'-O-dimethoxytrityl-2'-O—[2(2-N,N-dimethylaminoethoxy)-ethyl)]-5-methyl uridine and 5'-O-Dimethoxytrityl-2'-O—[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made by the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides, such as, the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation are effected by utilizing a 10% w/v solution of 3,H-1,2-benzodithiole-3-one 1,1-dioxide in acetonitrile for the oxidation of the phosphite linkages. The thiation reaction step time are increased to 180 seconds and preceded by the normal capping step. After cleavage from the CPG column and deblocking in concentrated ammonium hydroxide at 55° C. (12 to 16 hours), the oligonucleotides were recovered by precipitating with >3 volumes of ethanol from a 1 M $NH_4OAc$ solution.

Phosphinate oligonucleotides are prepared as described in U.S. Pat. No. 5,508,270.

Alkyl phosphonate oligonucleotides are prepared as described in U.S. Pat. No. 4,469,863.

3'-Deoxy-3'-methylene phosphonate oligonucleotides are prepared as described in U.S. Pat. No. 5,610,289 or U.S. Pat. No. 5,625,050.

Phosphoramidite oligonucleotides are prepared as described in U.S. Pat. No. 5,256,775 or U.S. Pat. No. 5,366,878.

Alkylphosphonothioate oligonucleotides are prepared as described in WO 94/17093 and WO 94/02499.

3'-Deoxy-3'-amino phosphoramidate oligonucleotides are prepared as described in U.S. Pat. No. 5,476,925.

Phosphotriester oligonucleotides are prepared as described in U.S. Pat. No. 5,023,243.

Borano phosphate oligonucleotides are prepared as described in U.S. Pat. No. 5,130,302 and U.S. Pat. No. 5,177,198.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. No. 5,378,825, U.S. Pat. No. 5,386,023, U.S. Pat. No. 5,489,677, U.S. Pat. No. 5,602,240 and U.S. Pat. No. 5,610,289.

Formacetal and thioformacetal linked oligonucleosides are prepared as described in U.S. Pat. No. 5,264,562 and U.S. Pat. No. 5,264,564.

Ethylene oxide linked oligonucleosides are prepared as described in U.S. Pat. No. 5,223,618.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular, bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides are synthesized.

RNA oligonucleotides are synthesized in a stepwise fashion. Each nucleotide is added sequentially (3' to 5' direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which has the following important properties; it is stable to the conditions of nucleoside phosphoramidite synthesis and oligonucleotide synthesis. However, after oligonucleotide synthesis the oligonucleotide is treated with methylamine which not only cleaves the oligonucleotide from the solid-support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product. Additionally, methods of RNA synthesis are well known in the art (Scaringe, 1996; Scaringe et al., 1998; Matteucci and Caruthers, 1981; Beaucage and Caruthers, 1981; Dahl et al., 1990; Reddy et al., 1994; Wincott et al., 1995; Griffin et al., 1967a; Griffin et al., 1967b).

RNA antisense compounds (RNA oligonucleotides) of the present invention can be synthesized by the methods herein or purchased from Dharmacon Research, Inc (Lafayette, Colo.).

Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 uM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type, wherein the "gap" segment of linked nucleosides is positioned between 5'- and 3'-"wing" segments of linked nucleosides and a second "open end" type, wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] chimeric phosphorothioate oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5'- and 3'-wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH$_4$OH) for 12 to 16 hours at 55° C. The deprotected oligonucleotide is then recovered by an appropriate method (precipitation, column chromatography), volume reduced in vacuo and analyzed spectrophotometrically for yield and for purity by capillary electrophoresis and by mass spectrometry.

[2'-O-(2-Methoxyethyl)]-[2'-deoxy]-[2'-O-(Methoxyethyl)] chimeric phosphorothioate oligonucleotides

[2'-O-(2-methoxyethyl)]-[2'-deoxy]-[2'-O-(methoxyethyl)] chimeric phosphorothioate oligonucleotides are prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] chimeric oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065.

Example 5

Design and Screening of Duplexed Antisense Compounds Targeting IGF-IR mRNA

In accordance with the present invention, a series of nucleic acid duplexes comprising the antisense compounds of the present invention and their complements can be designed to target IGF-IR mRNA. The nucleobase sequence of the antisense strand of the duplex may comprise at least a portion of an oligonucleotide selected from SEQ ID NOs:1 through 75 and SEQ ID NO:100 through 136 shown in Table 1

The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG and having a two nucleobase overhang of deoxythymidine(dT) would have the following structure:

| | | |
|---|---|---|
| cgagaggcggacgggaccgTT | Antisense Strand | [SEQ ID NO: 92] |
| TTgctctccgcctgccctggc | Complement | [SEQ ID NO: 93] |

RNA strands of the duplex can be synthesized by methods disclosed herein or purchased from Dharmacon Research Inc. (Lafayette, Colo.). Once synthesized, the complementary strands are annealed. The single strands are aliquoted and diluted to a concentration of 50 µM. Once diluted, 30 µL of each strand is combined with 15 µL of a 5× solution of annealing buffer. The final concentration of said buffer is 100 mM potassium acetate, 30 mM HEPES-KOH pH 7.4, and 2 mM magnesium acetate. The final volume is 75 µL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate IGF-IR gene expression.

When cells reach 80% confluency, they are treated with duplexed antisense compounds of the invention. For cells grown in 96-well plates, wells are washed once with 200 µL OPTI-MEM-1 reduced-serum medium (Gibco BRL) and then treated with 130 µL of OPTI-MEM-1 containing 12 µg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by real-time polymerase chain reaction (RT-PCR).

Example 6

Oligonucleotide Isolation

After cleavage from the controlled pore glass solid support and deblocking in concentrated ammonium hydroxide at 55° C. for 12 to 16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., 1991. Results obtained with HPLC-purified material were similar to those obtained with non-HPLC purified material.

Example 7

Oligonucleotide Synthesis

96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g., PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55 to 60° C.) for 12 to 16 hours and the released product then dried in vacuo. The dried product was then re-suspended in sterile water to afford a master plate from which all analytical and test plate samples are then diluted utilizing robotic pipettors.

Example 8

Oligonucleotide Analysis

96-Well Plate Format

Analysis of oligonucleotides targeting IGF-IR is as described in WO 2004/072284.

Example 9

Cell Culture and Oligonucleotide Treatment

Treatment of A549 cell cultures with oligonucleotides targeting IGF-IR is as described in WO 2004/072284.

Treatment with Antisense Compounds

For human cells the positive control oligonucleotide is selected from either ISIS 13920 (TCCGTCATCGCTCCT-CAGGG; SEQ ID NO:79) which is targeted to human H-ras, or ISIS 18078, (GTGCGCGCGAGCCCGAAATC; SEQ ID NO:80) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA; SEQ ID NO:81, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of IGF-IR Gene Expression

Analysis of oligonucleotides inhibition of IGF-IR is as described in WO 2004/072284.

Example 11

Design of Phenotypic Assays and in vivo Studies for the use of IGF-IR Gene Expression Inhibitors Phenotypic Assays Once IGF-IR gene expression inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of IGF-IR in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In Vivo Studies

The individual subjects of the in vivo studies described herein are warm-blooded vertebrate animals, which includes humans.

To account for the psychological effects of receiving treatments, volunteers are randomly given placebo or IGF-IR gene expression inhibitor. Furthermore, to prevent the doctors from being biased in treatments, they are not informed as to whether the medication they are administering is an IGF-IR gene expression inhibitor or a placebo. Using this randomization approach, each volunteer has the same chance of being given either the new treatment or the placebo.

Volunteers receive either the IGF-IR gene expression inhibitor or placebo for 8 week period with biological parameters associated with the indicated disease state or condition being measured at the beginning (baseline measurements before any treatment), end (after the final treatment), and at regular intervals during the study period. Such measurements include the levels of nucleic acid molecules encoding IGF-IR or IGF-IR protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are adults (age 18 to 65 years) and roughly an equal number of males and females participate in the study, excluding gender specific cancers. Volunteers with certain characteristics are equally distributed for placebo and IGF-IR gene expression inhibitor treatment. In general, the volunteers treated with placebo have little or no response to treatment, whereas the volunteers treated with the IGF-IR gene expression inhibitor are expected to show positive trends in the treatment of their disease state or condition index at the conclusion of the study.

Example 12

RNA Isolation

Total RNA and Poly(A)+mRNA isolation are as described in WO 2004/072284.

Example 13

Real-time Quantitative PCR Analysis of IGF-IR mRNA Levels

Quantitation of IGF-IR mRNA levels was accomplished by RT-PCR using the ABI PRISM (trademark) 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of PCR products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5'-end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3'-end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM (trademark) Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both ("multiplexing"). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM (registered trademark) Taq, 5 Units MuLV reverse transcriptase, and 2.5×ROX dye) to 96-well plates containing 30 μL total RNA solution (20-200 ng). The RT reaction was carried out by incubation for 30 minutes at 48° C. Following a 10 minute incubation at 95° C. to activate the PLATINUM (trademark) Taq, 40 cycles of a two-step PCR protocol were carried out: 95° C. for 15 seconds (denaturation) followed by 60° C. for 1.5 minutes (annealing/extension).

Gene target quantities obtained by RT-PCR are normalized using either the expression level of GAPDH, a gene whose expression is constant, or by quantifying total RNA using RiboGreen (trademark) (Molecular Probes, Inc. Eugene, Oreg.). GAPDH expression is quantified by RT-PCR, by being run simultaneously with the target, multiplexing, or separately. Total RNA is quantified using RiboGreen (trademark) RNA quantification reagent (Molecular Probes, Inc. Eugene, Oreg.). Methods of RNA quantification by RiboGreen (trademark) are taught in Jones et al., 1998.

In this assay, 170 μL of RiboGreen (trademark) working reagent (RiboGreen (trademark) reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Probes and primers to human IGF-IR were designed to hybridize to the IGF-IR nucleotide sequence, using published sequence information (GenBank accession number NM000875 (SEQ ID NO:76) or M69229 (SEQ ID NO:77) which is the 5' untranslated of the IGF-IR gene sequence (see FIG. 6).

For human IGF-IR the PCR primers were:

```
forward primer:
CCCTTTCTTTGCAGTTTTCCC (ISIS 161212; SEQ ID NO:
82);

reverse primer:
CGTCGTCGGCCTCCATT (ISIS 161214; SEQ ID NO: 83);
and the PCR probe was:
FAM-CCTTCCTGCCTCTCCGGGTTTGA-TAMRA (ISIS 161215;
SEQ ID NO: 84), where FAM is the fluorescent dye
and TAMRA is the quencher dye.
```

For human GAPDH the PCR primers were:

```
forward primer:
                                        (SEQ ID NO: 94)
GAAGGTGAAGGTCGGAGTC;

reverse primer:
                                        (SEQ ID NO:95)
GAAGATGGTGATGGGATTTC;
and the PCR probe was:
                                        (SEQ ID NO:96)
5' JOE-CAAGCTTCCCGTTCTCAGCC-TAMRA 3', where JOE is
the fluorescent reporter dye and TAMRA is the
quencher dye.
```

Example 14

Northern blot Analysis of IGF-IR mRNA Levels

Eighteen hours after antisense treatment, cell monolayers were washed twice with cold PBS and lyzed in 1 mL RNA-ZOL (trademark) (TEL-TEST "B" Inc., Friendswood, Tex.). Total RNA was prepared following manufacturer's recommended protocols. Twenty μg of total RNA was fractionated by electrophoresis through 1.2% w/v agarose gels containing 1.1% v/v formaldehyde using a MOPS buffer system (AMRESCO, Inc. Solon, Ohio). RNA was transferred from the gel to HYBOND (trademark)-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER (trademark) UV Crosslinker 2400 (Stratagene, Inc, La Jolla, Calif.) and then probed using QUICKHYB (trademark) hybridization solution (Stratagene, La Jolla, Calif.) using manufacturer's recommendations for stringent conditions.

To detect human IGF-IR an IGF-IR specific probe was prepared by PCR using the forward primer for human IGF-IR CCCTTTCTTTGCAGTTTTCCC (ISIS 161212; SEQ ID NO:82) and the reverse primer for human IGF-IR reverse primer sequence CGTCGTCGGCCTCCATT (ISIS 161214; SEQ ID NO:83). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER (trademark) and IMAGEQUANT (trademark) Software V3.3 (Molecular Dynamics, Sunnyvale, Calif.). Data was normalized to GAPDH levels in untreated controls.

Example 15

Antisense Inhibition of Human IGF-IR Expression

In accordance with the present invention, a series of antisense compounds were designed to target different regions of the human IGF-IR mRNA or the 5' untranslated region, using published sequences set forth in NM000875 (SEQ ID NO:77) and M69229 (SEQ ID NO:76). The compounds are shown in Table 1.

Antisense oligonucleotides of SEQ ID NOs:1 through 73 listed in Table 1 are targeted to human IGF-IR mRNA (GenBank Accession NO: NM_000875.2; incorporated herein as SEQ ID NO:78). Antisense oligonucleotides of SEQ ID NOs: 100 through 136 listed in Table 1 are targeted to SEQ ID NO:97, which is a composite of the 5' untranslated region sequence from human IGF-IR from M69229 (SEQ ID NO:77), excluding the promoter region, and the coding and 3' untranslated regions of NM_000875.2 (SEQ ID NO:78). The antisense oligonucleotides are 20 nucleotides long; the internucleotide linkages throughout are phosphorothioate linkages; five nucleotides in the 5' wing segment and 5 nucleotides in the 3' wing segment have 2'MOE modifications of the sugar described further herein. All cytidine residues are 5-methyl-cytidines. It will be understood however, that the invention is not limited to the exemplified antisense oligonucleotides to IGF-IR shown in Table 1 and that these antisense oligonucleotides are included to merely illustrate their use in the treatment of an IGF-IR positive tumor or cancer.

"Target site" indicates the first (5'-most) nucleotide number on the particular target sequence to which the compound binds. All the above compounds in Table 1 are antisense oligonucleotides of either the 5' untranslated region or the coding region of the IGF-IR. The compounds were analyzed for their effect on human IGF-IR mRNA levels by quantitative RT-PCR as described in other examples herein (see Table 1). Data are averages from 3 experiments. The positive control for each data point is identified in the Table 1 by sequence ID number. If present, "N.D." indicates "no data".

As shown in Table 1, some lead compounds (e.g., ISIS 175308, 175302, 175314, 175307, 175316, 175317, 175323, 323744, 323747, 323767, 323762 and 323737) demonstrated inhibition of IGF-IR expression in this assay. Exemplary target segments of IGF-IR comprise sequences that are complementary to the sequences of these lead compounds. SEQ ID NOs:85 through 91 represent exemplary target segments identified in IGF-IR. The "target site" in Table 1 indicates the first (5'-most) nucleotide number on the particular target nucleic acid to which the antisense oligonucleotide binds.

One of skill in the art will recognize or be able to ascertain, using no more than routine experimentation, further embodiments of the invention that encompass other compounds that specifically hybridize to these target segments and consequently inhibit the expression of IGF-IR.

Example 16

Evaluation of the Effects of IGF-IR Antisense Oligonucleotide on IGF-IR Levels and LNCaP and PC-3 Cell Growth and Apoptosis In Vitro The 2'-MOE-modified antisense oligonucleotide used in this study were synthesized as described previously. The sequence of the IGF-IR antisense oligonucleotide used corresponds to the human antisense oligonucleotide ISIS 175317 (SEQ ID NO:125; also known as ATL1101). The 8 nucleotide mismatch control oligonucleotide is ISIS 306064 (SEQ ID NO:99). ATL1101 was previously demonstrated to significantly inhibit IGF-IR mRNA expression in a dose-dependent and sequence specific manner in other cell lines as reported in WO 2004/072284.

Established methods were used to test the activity of IGF-IR antisense oligonucleotide on LNCaP and PC-3 cell growth (crystal violet assay) and apoptosis (FACS). Dose- and sequence-specific suppression of IGF-IR mRNA and protein expression in ATL1101-treated LNCaP and PC3 PC cell lines in vitro were observed by QT-PCR and western blotting. Effects of the IGF-IR antisense oligonucleotide on various putative targets, including IGF-IR and downstream targets were evaluated using western blotting.

PC-3 cells are derived from hormone-refractory human prostate cancer and LNCaP cells are derived from prostate cancer metastasis in the lymph node.

Example 17

Antitumor Activity of IGF-IR Antisense Oligonucleotide in vitro in PC-3 and LNCap Cell Lines mRNA and protein in vitro The sequence-specific and dose-dependent suppression of IGF-IR mRNA and protein expression in ATL1101-treated LNCaP and PC3 PC cell lines is shown in FIGS. 1A(i)-1A(ii) and 1B(i)-1B(ii).

FIGS. 1A(i)-1A(ii) show the sequence-specific and dose-dependent suppression of IGF-IR mRNA expression levels by ATL1101 in LNCaP (FIG. 1A (i)) and PC-3 (FIG. 1A (ii)) cells. LNCaP and PC-3 cells were transfected with IGF-IR antisense oligonucleotide (ATL1101) or control oligodeoxynucleotide (ISIS 306064). One day after treatment, total RNA was extracted, and IGF-IR mRNA expression was analyzed by quantitative RT-PCR. IGF-IR mRNA levels were normalized to levels of GAPDH mRNA and expressed here as mean±SE. ***, p<0.001 differ from control (oligofectamine only) by Student's t test. "Control" cells were treated with oligofectamine only. In LNCaP cells, IGF-IR expression was >70% suppressed by 10 nM ATL1101 and >90% at 200 nM ATL1101. In PC3 cells, IGF-IR expression was suppressed ~40% at 10 nM ATL1101, >50% at 50 nM ATL1101 and ~80% at 200 nM. Control oligodeoxynucleotide (ISIS 306064) did suppress IGF-IR mRNA expression but by less than 25% at maximal doses tested FIGS. 1B(i)-1B(ii) show sequence-specific and dose-dependent inhibition of IGF-IR protein by IGF-IR antisense oligonucleotide in LNCaP (FIG. 1B (i)) and PC-3 (FIG. 1B (i)) cells. LNCaP or PC3 cells cultured in vitro were transfected with indicated concentrations of IGF-IR antisense oligonucleotide (ATL1101) or control oligodeoxynucleotide (ISIS 306064) once per day on two sequential days. Two days after the second transfection, whole cell detergent lysates were prepared and 30 μg of total protein was subjected to SDS-PAGE and immunoblotted for IGF-IRB subunit, IR-BB subunit and vinculin expression. Oligofectamine, oligofectamine treated cells only. In LNCaP cells, IGF-IR expression was >80% suppressed by 10 nM ATL1101 and was undetectable at 100 nM ATL1101. In PC3 cells, IGF-IR expression was suppressed ~50% at 10 nM ATL1101, >80% at 50 nM ATL1101 and >90% at 200 nM. ATL1101 did not affect expression of the closest IGF-IR homologue, insulin receptor-B (IR-B) except at the highest ATL1101 concentration tested for each cell line, where expression of IR-B was suppressed <10%. Vinculin expression is shown as a loading control.

Growth In Vitro

Figure 2B:
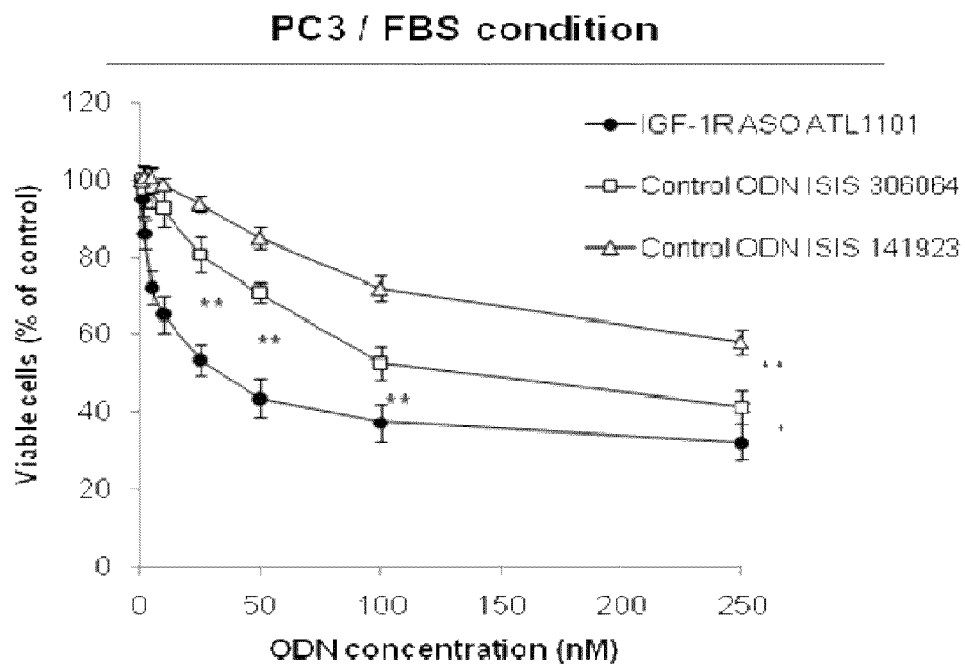
Figure 2C:
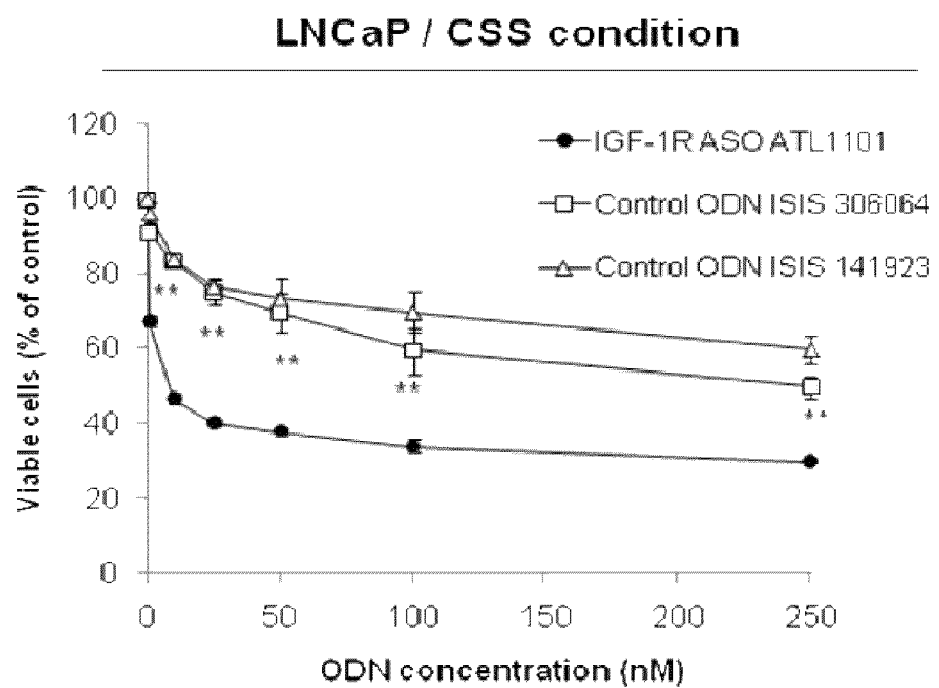

The inhibition of growth in LNCaP and PC3 cells treated with ATL1101 in vitro is shown in FIGS. 2A-2C. Cells were transfected with indicated concentrations of ATL1101, control oligodeoxynucleotides or oligofectamine as in FIGS. 1A(i)-1A(ii). Three days after treatment, cell viability was determined by crystal violet assay. Viable cell density was normalized to that of cells treated with oligofectamine. Points, means of triplicate analysis; bars, SE. *, p<0.05 differs from control oligodeoxynucleotide treatment group. **, p<0.01 differs from control oligodeoxynucleotide treatment group by Student's t test. While control oligodeoxynucleotides did induce a dose-dependent cytotoxic effect, ATL1101-transfected LNCaP and PC3 cell viability in FBS media (FIGS. 2A and 2B, respectively) was significantly reduced relative to oligodeoxynucleotide controls at all concentrations ≥10 nM to a maximum of ~60% achieved by 100 nM. LNCaP cells cultured in androgen-deprived conditions (CSS) (FIG. 2C) exhibited an increased sensitivity to ATL1101, reaching a 60% suppression of cell viability at 25 nM ATL1101.

Intracellular Signaling In Vitro

Figure 3B:
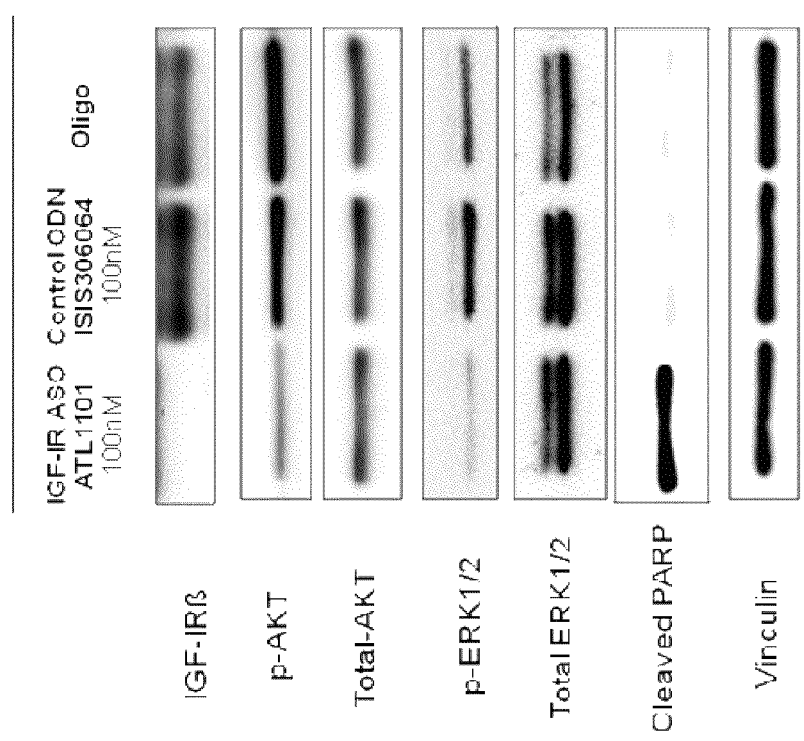
FIGS. 3A-B. Suppressed intracellular signaling in ATL1101-treated prostate cancer cell lines in vitro.
Figure 3A:
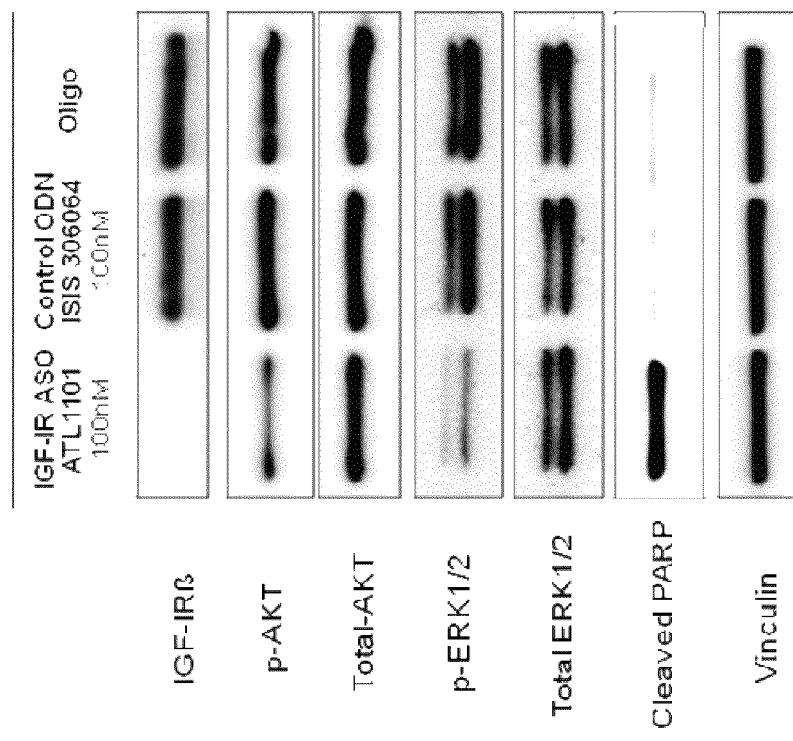

The suppression of intracellular signaling in IGF-IR antisense oligonucleotide-treated LNCaP (FIG. 3A) and PC3 (FIG. 3B) in vitro is shown in FIGS. 3A-3B. LNCaP or PC3 cells were transfected with 100 nM ATL1101 or control oligodeoxynucleotide (ISIS 306064) for two days. Cells were then cultured in FBS media for one day and in serum-free media for one day. Whole cell lysates (30 μg) were subjected to SDS-PAGE and immunoblotted to assess IGF-IRβ, p-AKT, total AKT, p-ERK1/2, total ERK1/2, cleaved PARP, and vinculin protein levels. Oligo, oligofectamine treated cells only. ATL1101 treatment resulted in undetectable IGF-IR expression and suppressed activation of AKT and ERK1/2 and increased cleaved PARP production in LNCaP and PC3 cells, indicating that cells were undergoing apoptosis due to suppressed pro-survival signaling, while IGF-IR expression, down-stream kinase signaling and induction of PARP cleavage was indistinguishable between control oligodeoxynucleotide and oligofectamine-treated cells.

Cell Cycle and Apoptosis In Vitro

Figure 4B:
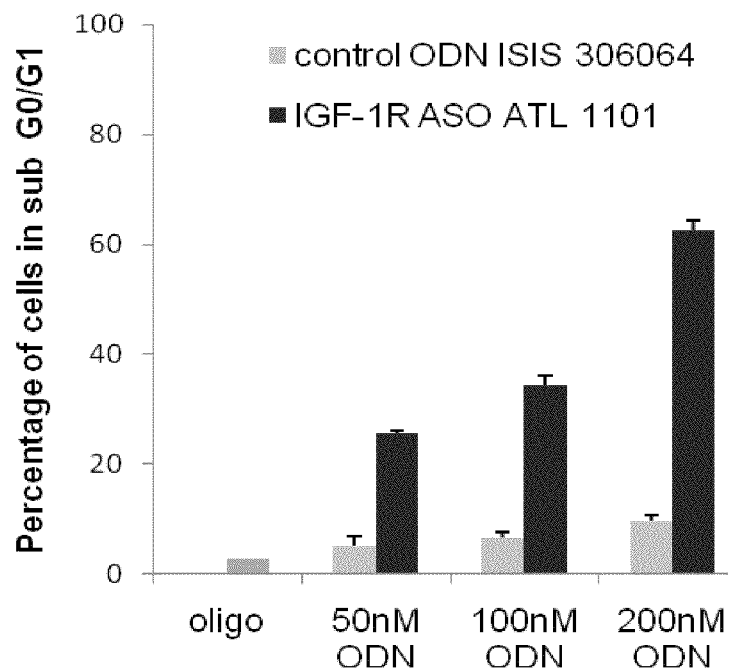
FIG. 4B shows the effect of ATL1101 in PC3 cells in FBS.

The Effect of IGF-IR silencing with IGF-IR antisense oligonucleotide (ATL1101) on LNCaP and PC3 cell apoptosis and cell cycle is shown in FIGS. 4A(i)-(ii), 4B, 4C(i)-(ii), and Table 2. Cells were transfected with indicated concentrations of ATL1101, control oligodeoxynucleotide or oligofectamine as in FIGS. 1A(i)-1B(ii). Two days after treatment, cell cycle analysis was determined by flow cytometry using propidium iodide staining. The fraction of cells undergoing apoptosis (subG0/G1 fraction) was significantly higher after treatment of ATL1101 compared with control oligodeoxynucleotide on both LNCaP and PC3 cells (FIGS. 4A (i) and (ii) and 4B, respectively). In FIGS. 4C(i)-(ii), LNCaP (FIG. 4C (i)) or PC-3 (FIG. 4C (ii)) cells were transfected with indicated concentration of ATL1101 or control oligodeoxynucleotide (ISIS 306064) for 2 days. Cells were then cultured in FBS media for one day and in serum-free media for one day. Whole cell lysates (30 μg) were subjected to SDS-PAGE and immunoblotted to assess Cyclin D1, Cyclin E, p-RB, total Rb, and p27 protein levels. Oligo, oligofectamine treated cells only. ATL1101 treatment suppressed activation of Cyclin D1, Cyclin E, p-RB and increased p27 protein production, indicating that this treatment resulted in G1/S phase cell cycle arrest. *** differs from control oligodeoxynucleotide treatment group ($p<0.0001$) by Student's t test.

Intracellular signaling in PC3 tumors in vivo

Total PC3 xenograft tumor proteins were extracted after the treatment of IGFI-R antisense oligonucleotide or control oligodeoxynucleotide for 7 days and IGF-IRβ, p-AKT, pERK1/2, and vinculin protein levels were analyzed by western blotting. The results are shown in FIG. 5D. Tumor growth ratio of corresponding tumors are also shown (FIG. 5E). Two of three mice treated with ATL1101 showed that ATL1101 treatment resulted in decreased IGF-IR expression and suppressed activation of AKT and ERK1/2 in proportion to the suppression of tumor growth.

TABLE 2

Effect of IGF-IR silencing with IGF-IR antisense oligonucleotide (ATL1101) on LNCaP and PC3 cell apoptosis and cell cycle.

| | | LNCaP FBS condition | | | LNCaP CSS condition | | | PC3 FBS condition | | |
|---|---|---|---|---|---|---|---|---|---|---|
| | | Oligo | Control ODN 100 nM | IGF-1R ASO 100 nM | Oligo | Control ODN 100 nM | IGF-1R ASO 100 nM | Oligo | Control ODN 200 nM | IGF-1R ASO 200 nM |
| % of total cells | Sub G0/G1 | 1.2 | 10.8 | 61 | 2.6 | 21.7 | 84.3 | 2.7 | 9.6 | 62.5 |
| | G0/G1 | 68.8 | 65.4 | 32.8 | 85 | 70.1 | 13.3 | 63.2 | 58.5 | 19.3 |
| | S | 15.6 | 11.2 | 3.4 | 5.6 | 3.8 | 1.2 | 16.4 | 13.7 | 9.8 |
| | G2/M | 14.4 | 12.6 | 2.8 | 6.8 | 4.4 | 1.2 | 17.7 | 18.2 | 8.4 |
| subG0/G1 + G0/G1:S + G2/M | | 2.3 | 3.2 | 15.1** | 7.1 | 11.2 | 40.7*** | 1.9 | 2.1 | 4.5** |

, *differs from control ODN treatment group ($p < 0.01$, $p < 0.001$, respectively) by Student's t test.

Example 18

PC-3 and LNCap Xenograft Tumor Studies In Vivo

One million PC-3 or LNCaP cells were injected subcutaneously in athymic mice. For LNCaP xenografts, when PSA values exceeded 50 ng/ml, mice were castrated and randomly selected for treatment with ATL1101 or control oligodeoxynucleotide (15 mg/kg) injected i.p. once daily for 7 days and 3 times per week thereafter. Blood samples were obtained from the tail vein of the mice once weekly to measure serum PSA by ELISA. For PC-3 xenografts, when tumors reached 100 mm³, mice were randomly selected and treated with the same protocol as LNCaP.

Figure 5A:
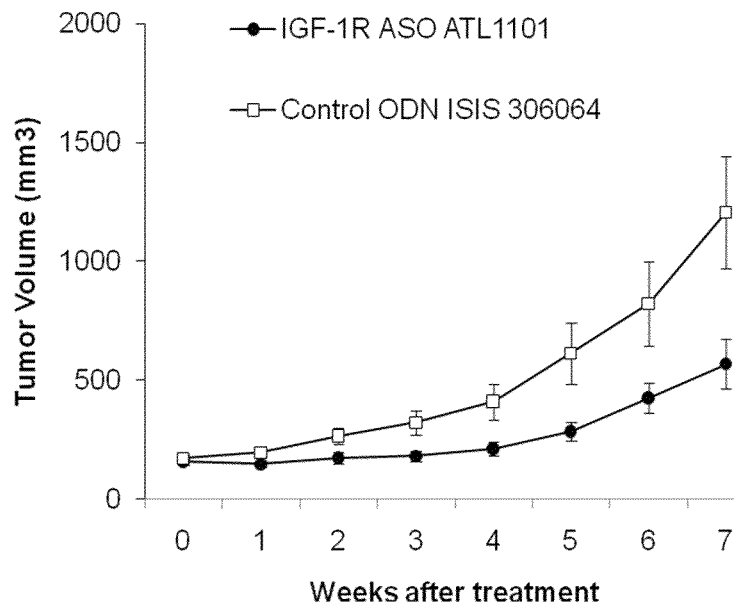
FIGS. 5A-5E. Effect of ATL1101 treatment on LNCaP and PC3 tumor in vivo.
Figure 5B:
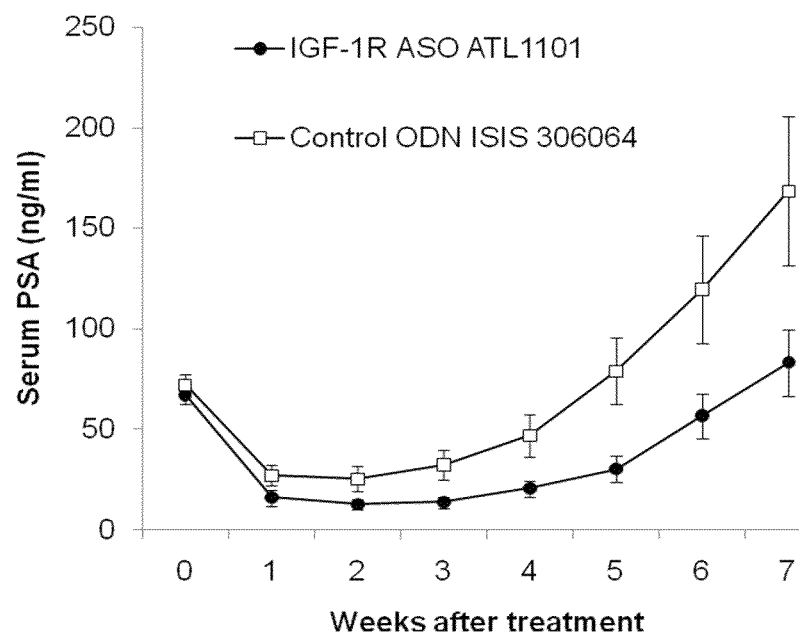
Figure 5C:
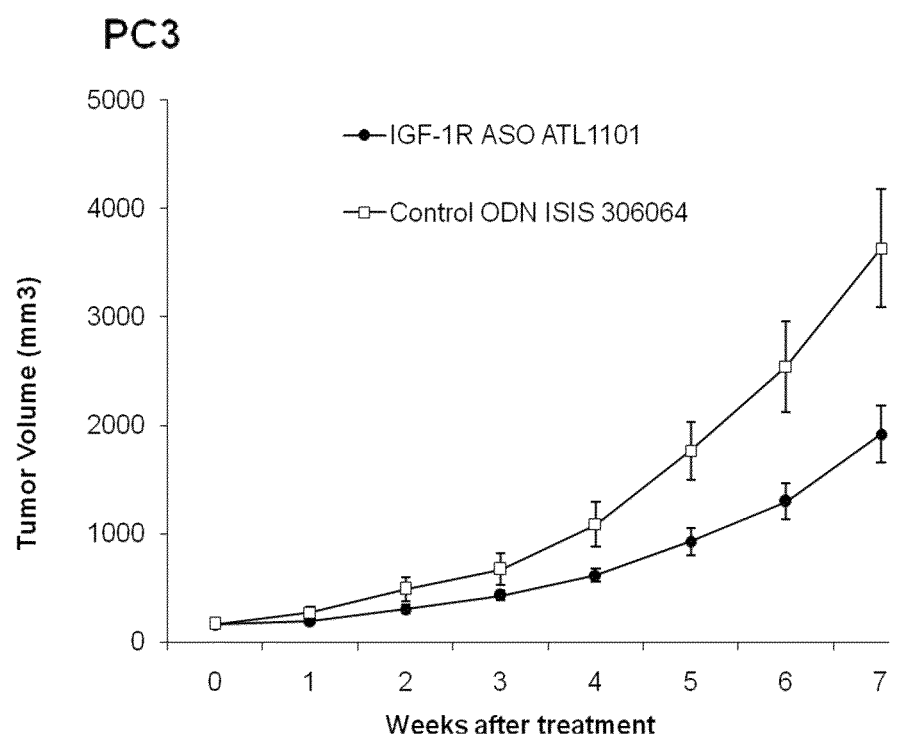
Figure 5D:
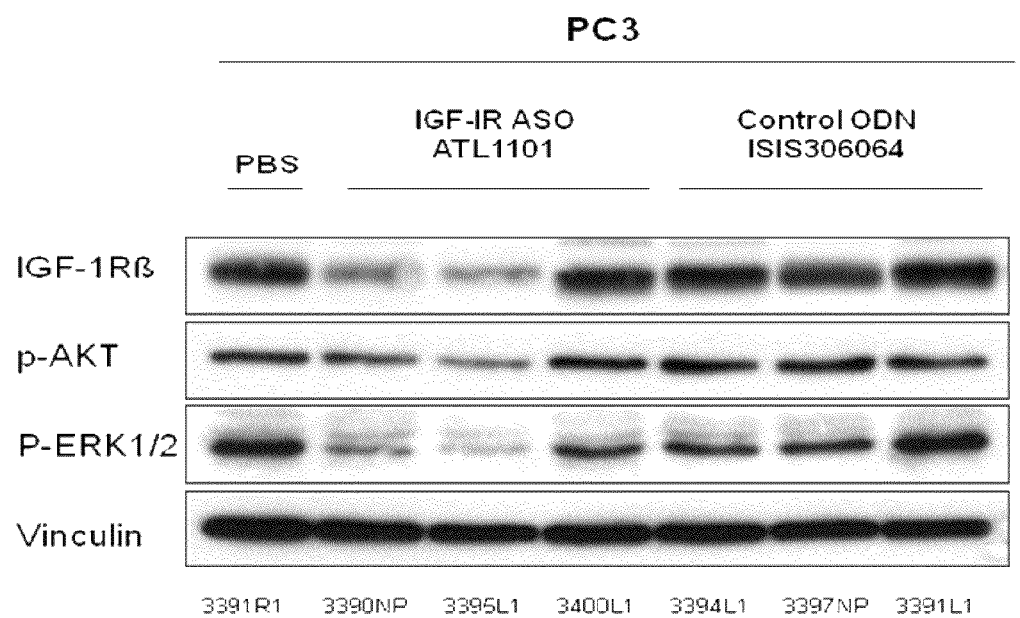
Figure 5E:
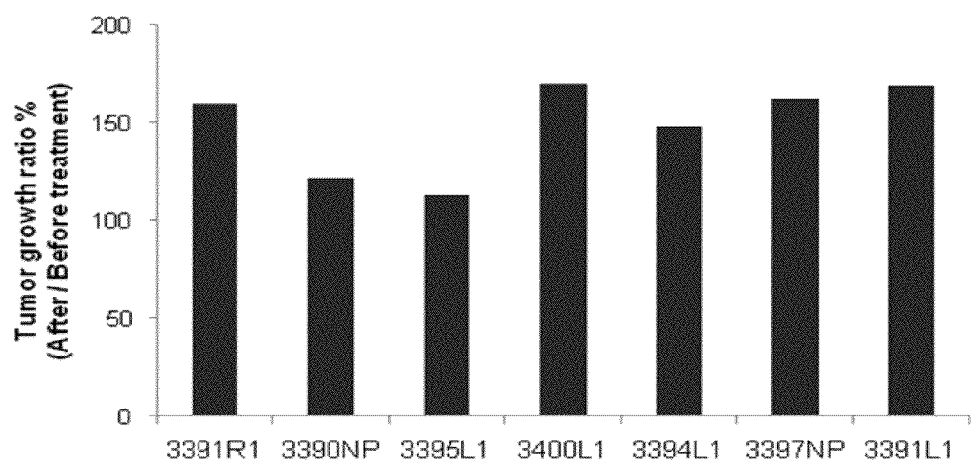

Effect of IGF-IR Antisense Oligonucleotide Treatment on LNCaP and PC3 Tumors In Vivo The effects of IGF-IR antisense oligonucleotide treatment in LNCaP and PC-3 tumors in vivo are show in FIGS. 5A-5C. LNCaP cells were inoculated s.c. and when PSA values exceeded 50 ng/ml, mice were castrated and randomly selected for treatment with ATL1101 or control oligodeoxynucleotide (15 mg/kg) injected i.p. once daily for 7 days and 3 times per week thereafter. Blood samples were obtained from the tail vein of the mice once weekly to measure serum PSA by ELISA. PC-3 cells were inoculated s.c. and when tumors reached 100 mm³, mice were randomly selected for treatment with the same protocol as LNCaP. Each point represents the mean tumor volume in each group containing 10 mice; bars, SE. * differs from control oligodeoxynucleotide treatment group ($p<0.05$) by Student's t test. In LNCaP xenografts, ATL1101 significantly delayed the tumor growth and PSA rise rates after castration. In PC3 xenografts, ATL1101 monotherapy significantly reduced tumor volume compared to the mice treated with control oligodeoxynucleotide (ISIS 306064).

Summary of In Vitro and In Vivo Observations

The present inventors observed dose- and sequence-specific suppression of IGF-IR mRNA and protein expression in ATL1101-treated LNCaP and PC3 PC cell lines in vitro (Example 17). Suppressed IGF-IR expression correlated with decreased proliferation and increased apoptosis of androgen-independent PC3 cells under standard culture conditions and increased apoptosis of androgen-responsive LNCaP cells under androgen-deprived culture conditions (Example 17).

Compared to control oligonucleotides, ATL1101 significantly suppressed PC3 tumor growth as a monotherapy in murine xenografts. Similarly ATL1101 significantly delayed onset of castrate resistant prostate cancer (CRPC) progression of LNCaP xenografts following castration as measured by tumor growth and serum PSA levels. Immunoblot analysis of harvested in vivo tumor tissues showed that suppression of IGF-IR expression correlated with decreased tumor growth in vivo.

This study reports the first preclinical proof-of-principle data that this novel IGF-IR antisense oligonucleotide selectively suppresses IGF-IR expression, suppresses growth of CRPC tumors and delays CRPC progression in vitro and in vivo.

Example 19

Antitumor Activity of IGF-IR Antisense Oligonucleotide In Vivo in PC-3 Xenograft Model with Paclitaxel In vivo treatments in a PC-3 xenograft model may also be done as described by Zellweger et al., 2001. In a first experiment, mice are randomized to one of three arms for treatment with 2'-MOE-modified IGF-IR antisense oligonucleotide plus Paclitaxel, or mismatch control oligonucleotides plus Paclitaxel. Each experimental group consists of 10 mice. After randomization, 12.5 mg/kg of IGF-IR antisense oligonucleotide or mismatch control oligonucleotides are injected intraperitoneal (i.p.) once daily into each mouse for 28 days. From days 10 to 14, and from days 24 to 28, 0.5 mg of polymeric micellar Paclitaxel (Leung et al., 2000) is administered once daily by intravenous (i.v.) injection. Tumor volume is measured once weekly and calculated by the formula length×width×depth×0.5236. Data points are reported as mean tumor volumes+/−S.D. In each of the three treatment arms, three mice are designated immediately after randomization to be harvested 1 week after the last oligonucleotide/ Paclitaxel treatment (day 35) to determine multiple serum parameters for comparison of in vivo antisense oligonucleotide toxicity.

In a second set of experiments, mice are randomized to one of two arms for treatment with 2'-MOE-modified IGF-IR antisense oligonucleotide once weekly, or mismatch control oligonucleotides once weekly. Each experimental group consists of 8 mice. After randomization, 12.5-90 mg/kg IGF-IR antisense oligonucleotide or mismatch control oligonucleotides are injected i.p. once weekly into each mouse over 4 weeks. Animals in all 2 treatment arms additionally receive polymeric micellar Paclitaxel as described above. Tumor volume is measured and data points are reported as described above.

In a third in vivo experiment, mice are randomized to one of two arms for treatment with either 2'-MOE modified IGF-IR antisense oligonucleotide or mismatch. Each experimental group consists of 12 mice. IGF-IR antisense oligonucleotide (12.5 mg/kg) is injected i.p. once daily into each mouse for 5 days. PC-3 tumors are harvested 1, 3, 5, and 7 days after the last antisense oligonucleotide injection for Northern blot and CGE analysis of IGF-IR. All animal procedures are performed according to the guidelines with appropriate institutional certification.

Example 20

In Vitro Treatment (MTT Assay) with Paclitaxel or Docetaxel

MTT 3-(4,5-dimethylthiazol-2-yl)-2,5-diphenyltetrazolium bromide, is a laboratory test and a standard calorimetric assay which measures changes in color to determine cellular proliferation (growth rate). The in vitro growth inhibitory effects of 2'-MOE-modified IGF-IR antisense oligonucleotide plus Paclitaxel or docetaxel on PC-3 cells can be compared using the MTT assay as previously described (Miyake et al., 1998). Briefly, $10^4$ cells are seeded in each well of 96-well microtiter plates and allowed to attach overnight. Cells are then treated once daily with 500 nM either IGF-IR antisense oligonucleotide or mismatch control oligonucleotides for 2 days. Following antisense oligonucleotide treatment, cells are treated with various concentrations of Paclitaxel or docetaxel. After 48 hours of incubation, 20 μl of 5 mg/ml MTT (Sigma Chemical Co., St. Louis, Mo.) in phosphate-buffered saline is added to each well, followed by incubation for 4 hours at 37° C. The formazan crystals are dissolved in dimethyl sulfoxide. The optical density is determined with a microculture plate reader (Becton Dickinson Labware, Lincoln Park, N.J.) at 540 nm. Absorbance values are normalized to the values obtained for the vehicle-treated cells to determine the percentage of survival.

Example 21

Antitumor Activity of IGF-IR Antisense Oligonucleotide in vivo in BM18 Xenograft Model with and without Androgen Withdrawal and with and without Paclitaxel McCulloch et al., (2005) have described a novel androgen dependent human prostate cancer xenograft model derived from bone metastasis. The effects of IGF-IR antisense oligonucleotide in vivo androgen withdrawal and Paclitaxel can be determined in this model. A 1 $mm^3$ piece of BM18 xenograft tumor is implanted subcutaneously into the lateral flank of each male SCID mouse. Once the BM18 xenograft reaches approximately 100 to 600 $mm^3$, calculated as described by Cher et al., 2003, mice are castrated by performing a bilateral orchioepididymectomy under isoflourane anesthetic (n=10). Mock castrations are performed as a control (n=8). The serum levels of PSA may be determined throughout the duration of the BM18 tumor growth and its subsequent regression post-androgen withdrawal, before and after castration.

In a first experiment, mice are randomized to one of three arms for treatment with 2'-MOE-modified IGF-IR antisense oligonucleotide plus Paclitaxel, or mismatch control oligonucleotides plus Paclitaxel. Each experimental group consists of 10 mice. After randomization, 12.5 mg/kg of IGF-IR antisense oligonucleotide or mismatch control oligonucleotides is injected i.p. once daily into each mouse for 28 days. From days 10 to 14, and from days 24 to 28, 0.5 mg of polymeric micellar Paclitaxel (Leung et al., 2000) is administered once daily by i.v. injection. Tumor volume is measured once weekly. Data points are reported as mean tumor volumes+/− S.D. In each of the three treatment arms, three mice are designated immediately after randomization to be harvested 1 week after the last oligonucleotide/Paclitaxel treatment (day 35) to determine multiple serum parameters for comparison of in vivo antisense oligonucleotide toxicity.

In a second set of experiments, mice are randomized to one of two arms for treatment with 2'-MOE-modified IGF-IR antisense oligonucleotide once weekly, or mismatch control oligonucleotides once weekly. Each experimental group consists of 8 mice. After randomization, 12.5 to 90 mg/kg IGF-IR antisense oligonucleotide or mismatch control oligonucleotides is injected i.p. once weekly into each mouse over 4 weeks. Animals in all two treatment arms additionally receive polymeric micellar Paclitaxel as described above. Tumor volume is measured and data points were reported as described above.

In a third in vivo experiment, mice are randomized to one of two arms for treatment with either 2'-MOE modified IGF-IR antisense oligonucleotide or mismatch. Each experimental group consists of 12 mice. IGF-IR antisense oligonucleotide (12.5 mg/kg) is injected i.p. once daily into each mouse for 5 days. BM18 tumors are harvested 1, 3, 5, and 7 days after the last antisense oligonucleotide injection for Northern blot and CGE analysis of IGF-IR.

Example 22

Assessment of In Vivo Tumor Growth

In vivo treatments in a LNCaP xenograft model may also be done substantially as described by Gleave et al., 1999 and tumor measured as outlined by Sato et al., 1996. Mice bearing tumors between 100 to 200 $mm^3$ in volume are castrated via a scrotal approach and randomly assigned to a treatment arm. Mice are treated beginning 1 or 7 days after castration with 12.5 mg/kg antisense oligonucleotide i.p. twice daily in the first experiment and with 12.5 mg/kg antisense oligonucleotide i.p. once daily for the second experiment. The antisense oligonucleotides can be dosed at daily doses of approximately 12.5 mg/kg/day in the xenografts models or ~90 mg/kg/week doses. Mice may also be treated with typical dose response series of 90 mg/kg/week, 45 mg/kg/week, 23 mg/kg/week, and 11 mg/kg/week, or daily doses of 12.5, 6.3, 3.1, and 1.6 mg/kg. Tumor volume and serum PSA measurements are performed weekly. Data points for both sets of experiments were expressed as average tumor volumes+/−SEs of the mean.

Blood samples are obtained for serum PSA levels with tail vein incisions of the LNCaP xenografted mice before treatment and then once weekly after starting antisense oligonucleotide treatment. Serum PSA levels are determined by an enzymatic immunoassay kit with a lower limit of sensitivity of 0.2 µg/liter (Abbott IMX, Montreal, Quebec, Canada), according to the manufacturer's protocol. PSA velocity is defined as the rate of change of serum PSA over time, whereas PSA doubling time is defined as the number of doublings of serum PSA over the treatment period. Time to androgen-independent PSA regulation are defined as the duration of time required after castration for serum PSA levels to return to or increase above precastrate levels.

Example 23

Proliferation Study data

Ki67 Immunohistochemistry In Vivo

Tumors and cancers for treatment with antisense to IGF-IR may include those in which proliferation is observed such as may be measured using Ki67 labeling index.

The present inventors assessed proliferation by Ki67 labeling in paraffin wax-embedded, formalin-fixed, 3 mm diameter, full-thickness psoriatic skin biopsies at the conclusion of the treatment phase of topically applied ATL1101. The tissue was analyzed to assess the effect of the antisense treatments on Ki67 expression using immunohistochemical analysis. Statistically significant reduction in Ki67 by length (mm) and area (mm squared) vs. mismatch control was observed.

Ki67 is commonly used to detect proliferating cells as it is only expressed during cell cycle progression. Ki67 is thought to be "a Ran-associated protein with a role in the disintegration and reformation of the nucleolus and thereby in entry into and exit from the M-phase" (Schmidt et al., 2003).

Example 24

Figure 7A:
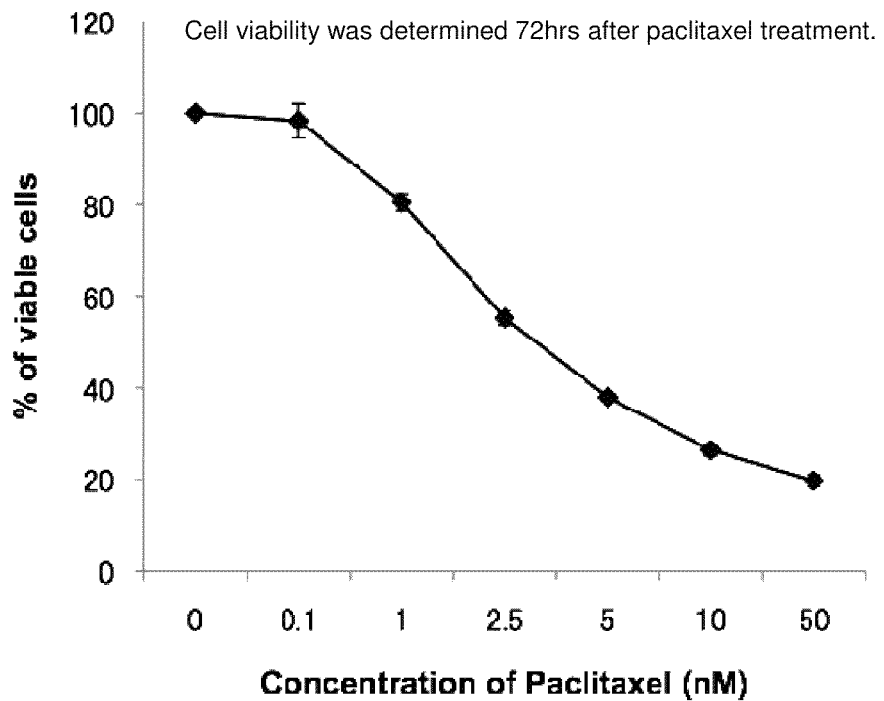
FIGS. 7A-7D. Inhibition of growth in PC3 cells treated ATL1101 in vitro with Paclitaxel.
Figure 7B:
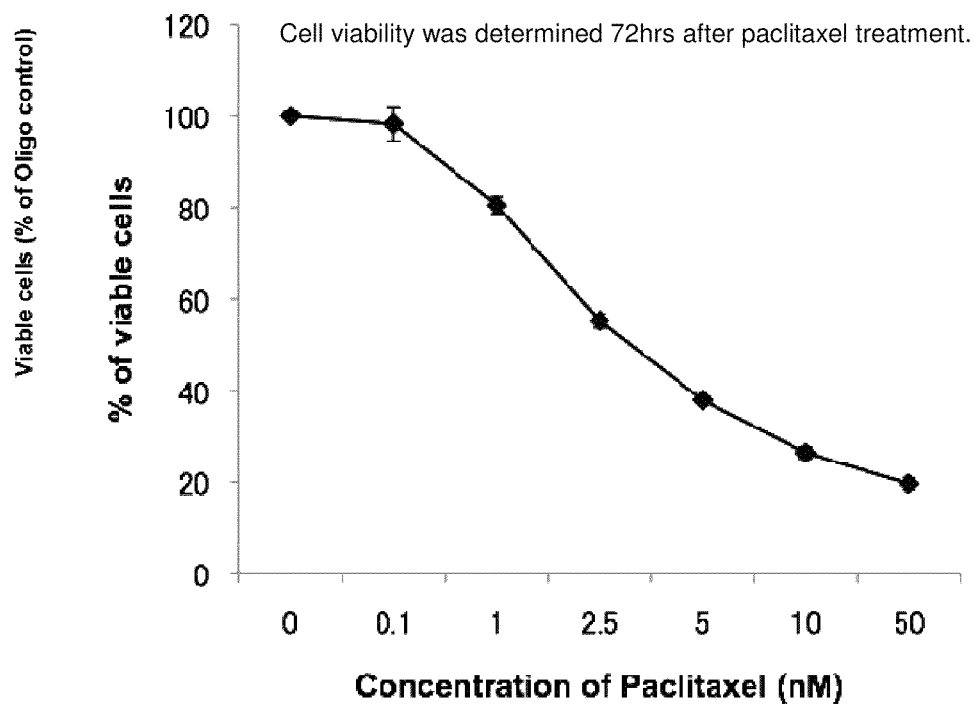
Figure 7C:
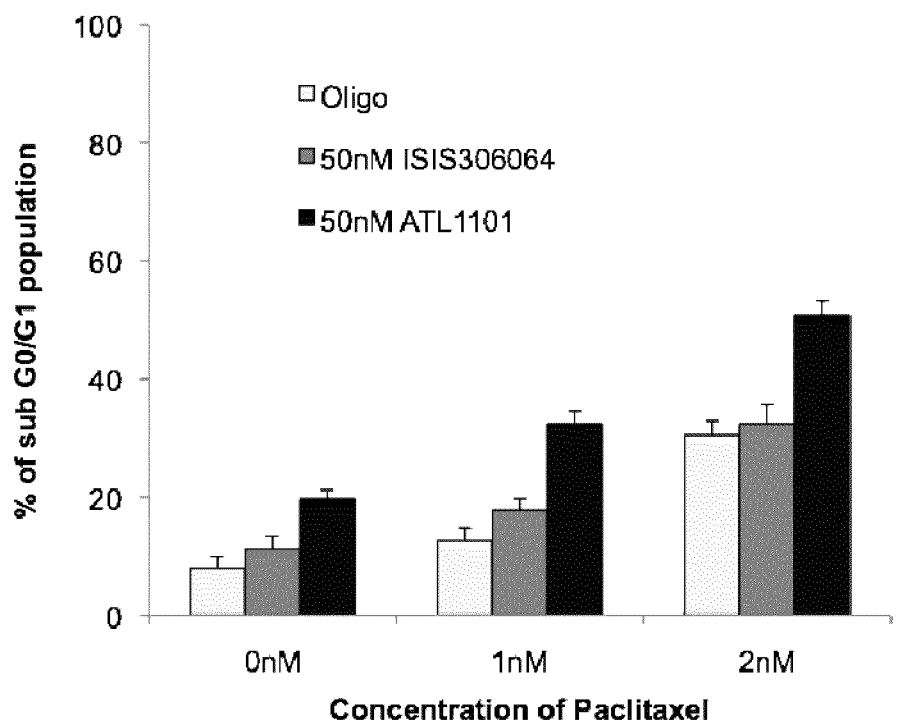

Antitumor Activity of IGF-IR Antisense Oligonucleotide In Vitro in PC-3 Cell Line with Paclitaxel PC3 cells cultured in vitro were transfected at concentrations of IGF-IR antisense oligonucleotide (ATL1101) or control oligodeoxynucleotide (ISIS 306064) ranging from 12.5 nM to 50 nM or oligofectamine control once per day on two sequential days. After the $2^{nd}$ transfection, the PC3 cells were treated with concentrations of between 0.1 to 50 nM Paclitaxel. The number of viable cells remaining were determined 72 hours after Paclitaxel treatment. The % of viable cells was determined 72 hours after 0.1 to 50 nM Paclitaxel treatment alone as shown in FIG. 7A. The number of viable cells expressed as a % of control oligofectamine (OTC) viable cells are shown in FIG. 7B. FIG. 7C shows the percentage of apoptotic cells 48 hours after 50 nM ATL1101 or control oligodeoxynucleotide (ISIS 306064) or oligofectamine and 1 nM or 2 nM Paclitaxel treatment as determined by FACS.

In cultured PC3 cells, cell viability decreased as expected with increasing concentrations of Paclitaxel. Transfection with ATL1101 further reduced viable cell count at a given Paclitaxel concentration, and reduced the concentration of Paclitaxel required to give the same viable cell count. For example, at 0.1 nM Paclitaxel, the viable cell count for PC3 cells was only reduced approximately 5%, compared with oligofectamine transfection reagent alone and no Paclitaxel. Cells treated with both 0.1 nM Paclitaxel and mismatch control oligonucleotide ISIS 306064 at 12.5 nM also had approximately 5% reduced viability. In contrast, cells treated with 0.1 nM Paclitaxel and ATL1101 at 12.5 nM had approximately 45% reduced viability. In another example, cells treated with 1 nM Paclitaxel and 25 nM ATL1101 had similar viability to cells treated with a 10-fold higher Paclitaxel concentration (10 nM), and 25 nM mismatch control oligodeoxynucleotide ISIS 306064. In cell culture the amount of Paclitaxel required to induce tumor cell apoptosis was significantly reduced when used in combination with ATL1101. This shows the ability of ATL1101 to sensitize tumor cells to the cytotoxic effects of Paclitaxel, and as a chemosensitizing agent to be used in combination with existing prostate treatments.

Figure 7D:
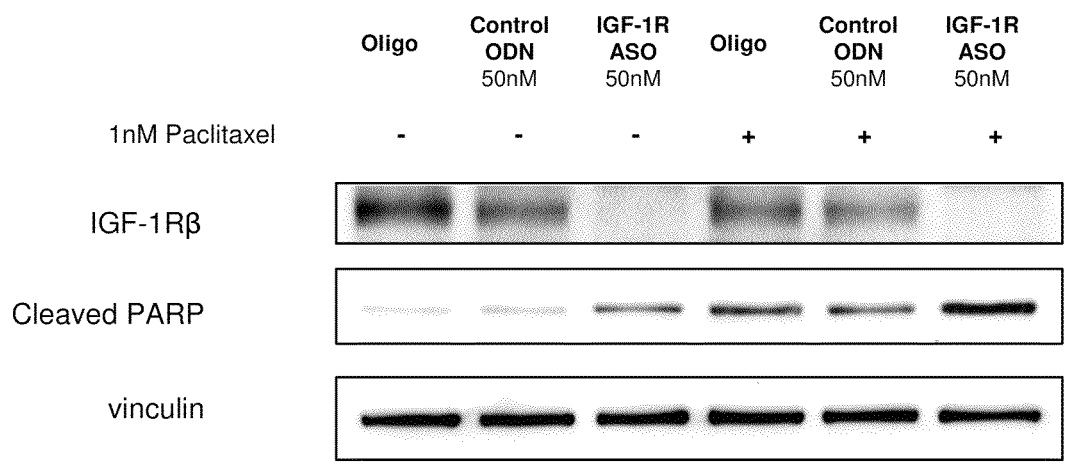

Two days after the second transfection, whole cell detergent lysates were prepared from the PC3 cells treated with 50 nM of IGF-IR antisense oligonucleotide (ATL1101) or control oligodeoxynucleotide (ISIS 306064) or oligofectamine, with 1 nM PaclitaxelPaclitaxel and total protein was subjected to SDS-PAGE and immunoblotted for IGF-IRB subunit, cleaved PARP and vinculin expression. The results are shown in FIG. 7D. Vinculin expression is shown as a loading control. Transfection with ATL1101 specifically reduced IGF-IRB levels with or without Paclitaxel treatment.

Example 25

Figure 8:
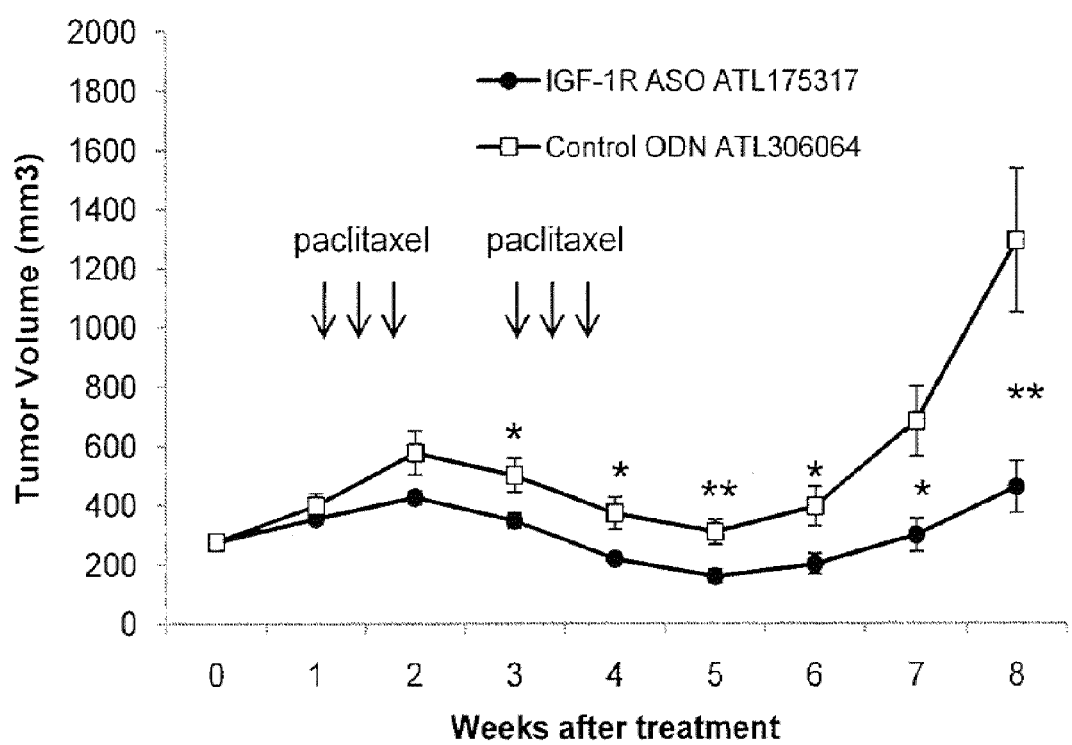
FIG. 8. Inhibition of growth in PC3 cells treated with ATL1101 or control oligodeoxynucleotide (ISIS 306064) in vivo with Paclitaxel.

Antitumor Activity of IGF-IR Antisense Oligonucleotide in vivo in PC-3 Xenograft Model with Paclitaxel In vivo treatments in a PC-3 xenograft model were done substantially as described by Zellweger et al., 2001. PC3 cells ($2 \times 10^6$ cells) were xenografted by subcutaneous injection into recipient 6-8 week-old athymic nude (nu/nu) mice. When tumors reached 200 mm³, mice were randomly assigned to one of two arms for treatment with 2'-MOE-modified IGF-IR antisense oligonucleotide (ATL1101) plus Paclitaxel, or mismatch control oligodeoxynucleotide ISIS 306064 plus Paclitaxel. Each experimental group consisted of 10 mice. After randomization, 15 mg/kg of ATL1101 antisense oligonucleotide or mismatch control oligonucleotide were injected intraperitoneal (i.p.) into each mouse once daily for the first 5 days and 3 times a week (every other day) thereafter for 7 weeks. On days 7, 9, 11, and on days 21, 23, and 25, 0.5 mg of polymeric micellar Paclitaxel was administered once daily by i.v. injection. Mean Tumor volume was measured once weekly for 8 weeks and calculated by the formula length× width×depth×0.5236. Data points were reported as mean tumor volumes (mm3)+/− standard error of the means as shown in FIG. 8.

In PC3 mice, after 5 weeks of treatment, mean tumor size in mice treated with Paclitaxel and mismatch control oligodeoxynucleotide was 326+/−40.9 mm³ compared with 175+/−20.1 mm³ in mice treated with Paclitaxel and ATL1101, or 53.7% of control (p<0.01). After 8 weeks of treatment, mean tumor size in mice treated with Paclitaxel and mismatch control oligodeoxynucleotide was 1417+/−222 mm$^3$ compared with 507+/−79.3 mm$^3$ in mice treated with Paclitaxel and ATL1101, or 35.8% of control (p<0.01).

Example 26

Figure 9:
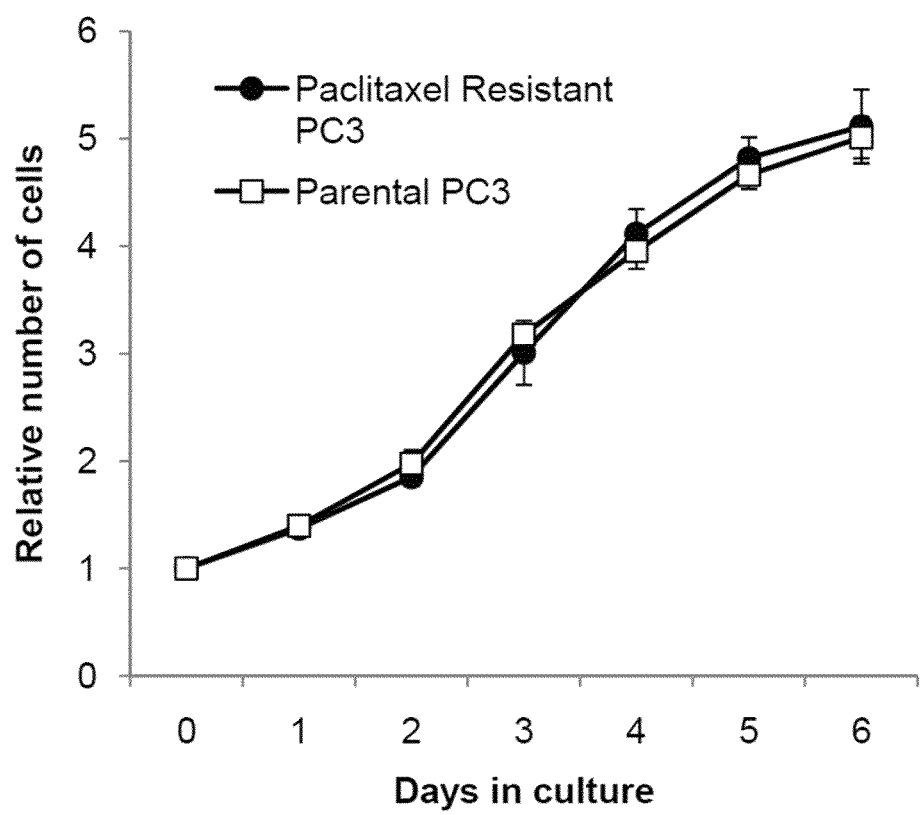
FIG. 9. Cell growth of PC3 and Paclitaxel resistant PC3 (PC3-PtxR) cells in standard culture conditions in vitro.
Figure 10A:
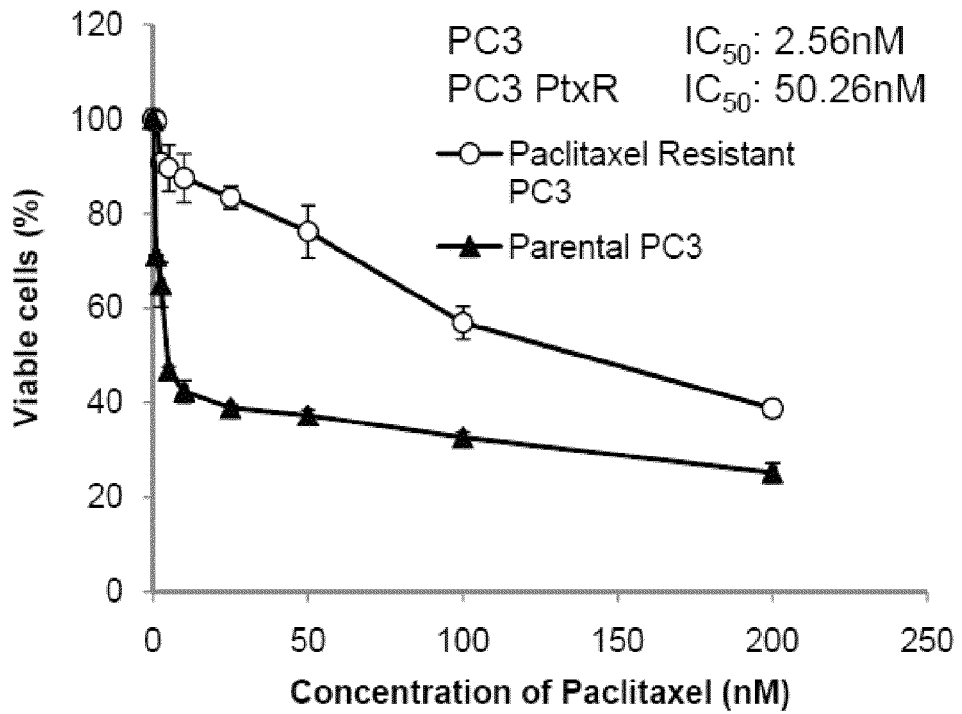
FIGS. 10A-D. PC3-PtxR cell line exhibits resistance in vitro to Paclitaxel (FIG. 10A), Docataxel (FIG. 10B), Mitoxantrone (FIG. 10C), and Cisplatin (FIG. 10D).
Figure 10B:
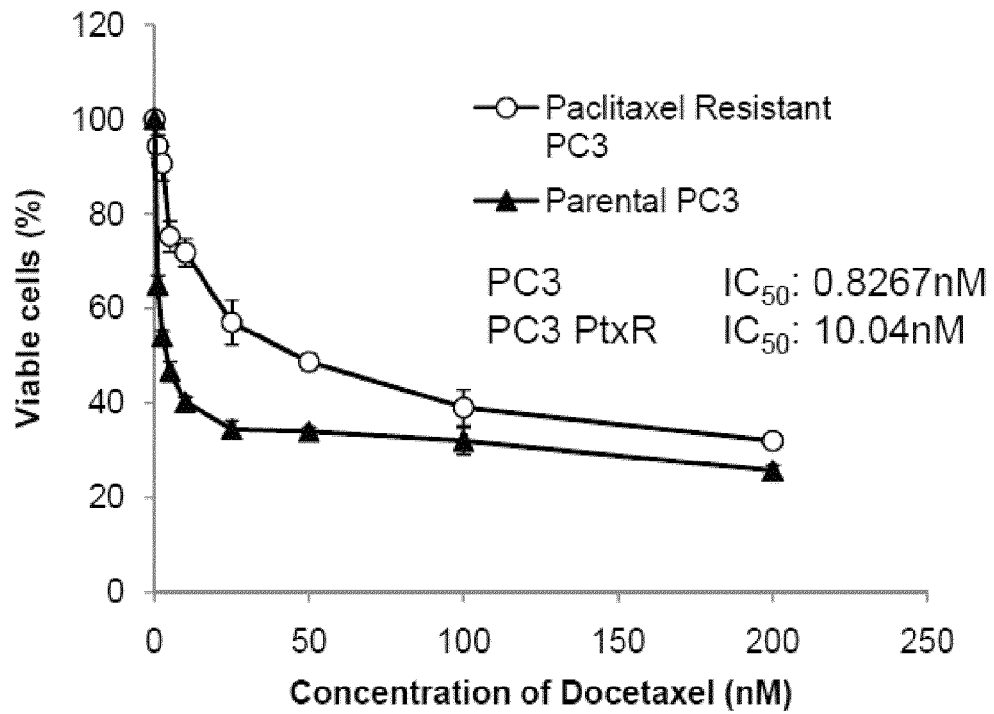
Figure 10C:
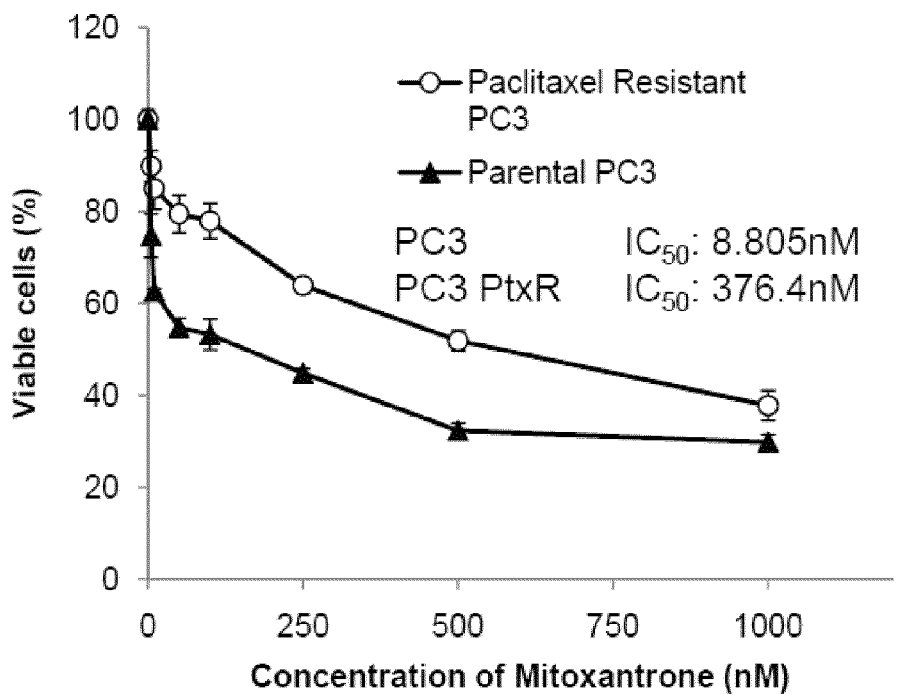
Figure 10D:
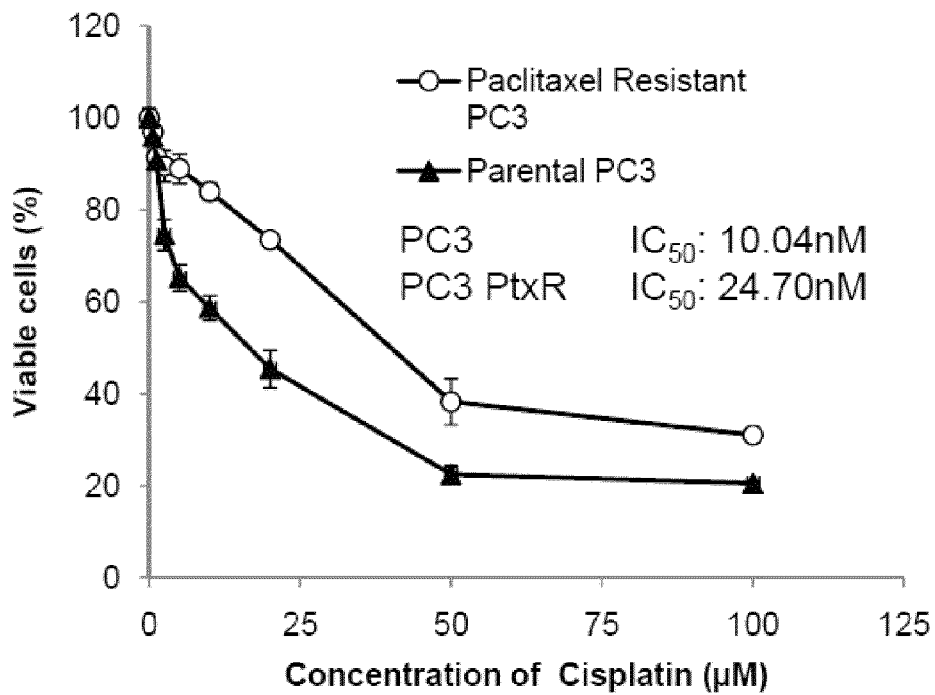

Antitumor Activity of IGF-IR Antisense Oligonucleotide In Vitro in PC-3 Cell Line (Ptx-R PC-3) Selected for Resistance to Paclitaxel PC3 cells cultured in vitro were selected for resistance to Paclitaxel (Ptx-R). The growth of PC3 and Ptx-R PC-3 cells in standard culture conditions (DMEM+5% FBS) is indistinguishable by the crystal violet method (FIG. 9). The growth of Ptx-R PC3 cells cultured in up to 200 nM Paclitaxel is distinguishable from PC3, with an IC50 of 50.26 nM and 2.56 nM, respectively (FIG. 10A). The Ptx-R PC3 cells exhibit multi-drug resistance to other neoplastic chemotherapeutic agents under standard culture conditions (FIGS. 10B-D). They are resistant to another taxane, Docataxel (IC50 10.04 nM vs. 0.8267 nM for PC3), and to Mitoxantrone (IC50 376.4 nM vs. 8.805 nM for PC3) and Cisplatin (IC50 24.7 nM vs. 10.04 nM for PC3).

Figure 11A:
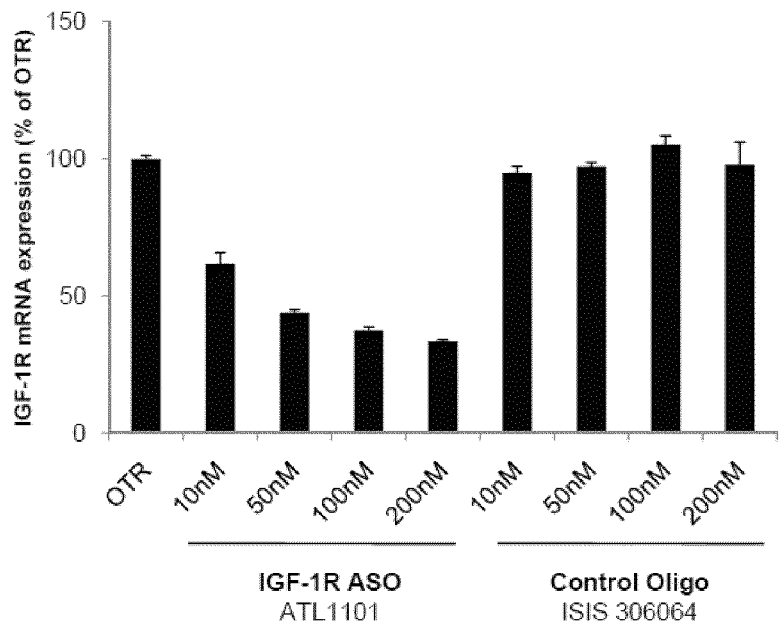
FIGS. 11A-C. ATL1101 sequence specific and dose dependent suppression of IGF-IR mRNA and IGF-IR protein expression in PC3-PtxR cells.
Figure 11B:
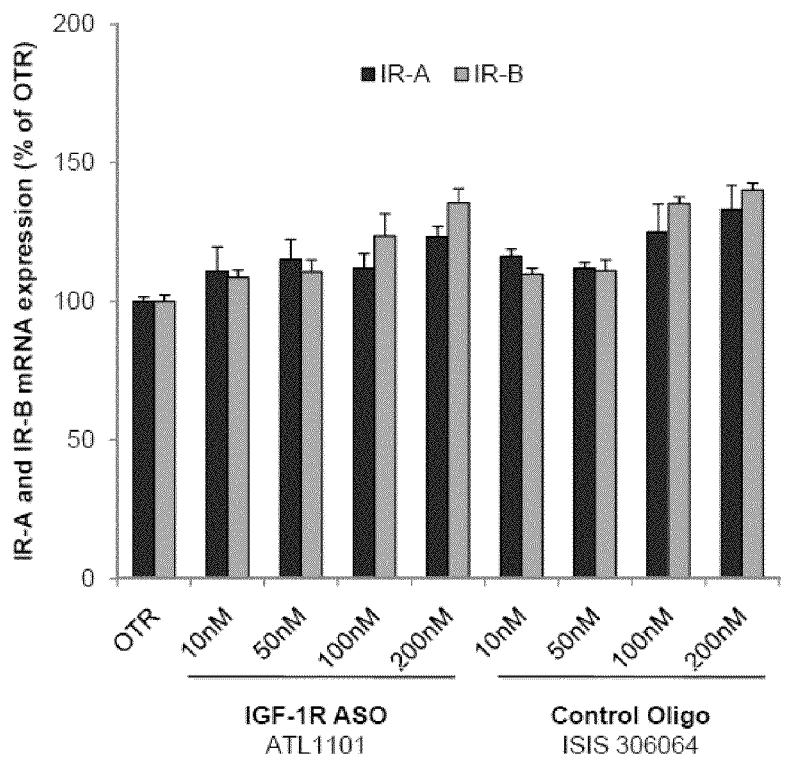
Figure 11C:
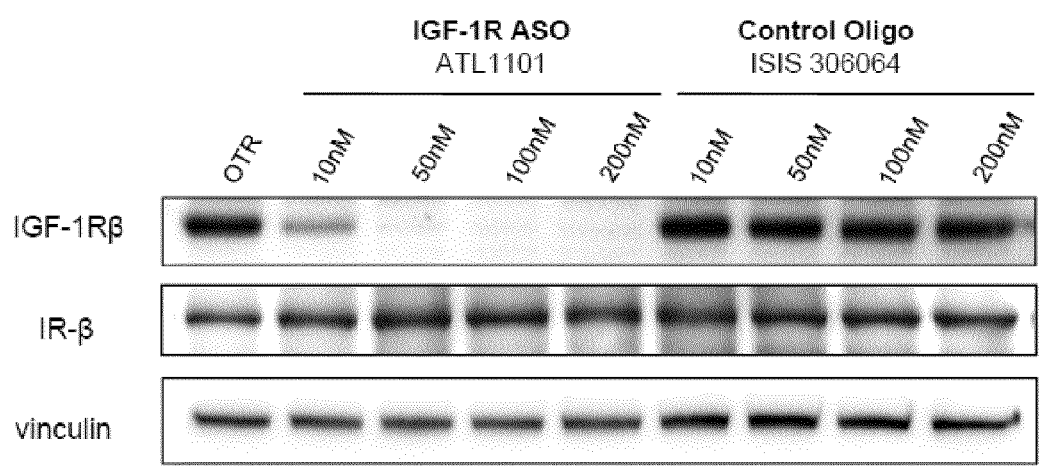

The PC3 Ptx-R cells retain sensitivity to ATL1101-induced IGF-IR down regulation at the mRNA and protein level as shown in FIGS. 11A-C. ATL1101 at 10 to 200 nM concentrations specifically reduced target IGF-IR mRNA and IGF-IRβ subunit protein levels, whereas a control oligodeoxynucleotide (ISIS 306064) at the same concentrations had no effect on IGF-IR mRNA and protein levels compared to the negative control oligofectamine transfection reagent (OTR). ATL1101 and the control oligodeoxynucleotide ISIS 306064 had no effect on either of the alternative spliced isoform transcripts of the insulin receptor, IR-A, IR-B or IR-β protein or vinculin protein levels.

Figure 12:
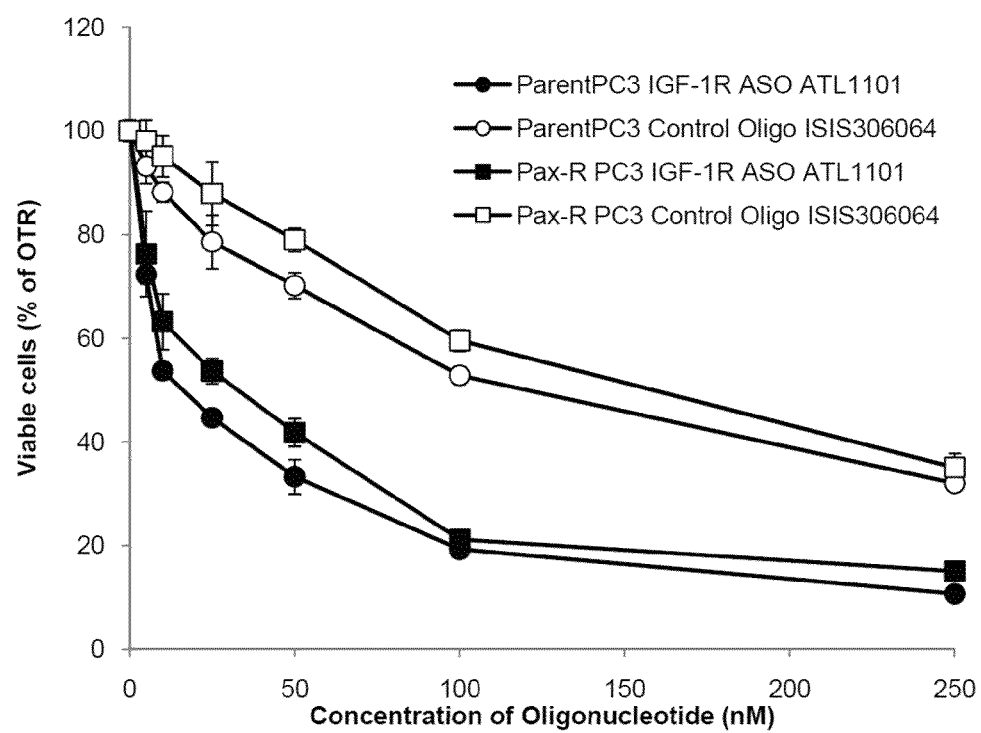
FIG. 12. Effect of ATL1101 treatment on PC3 and PC3-PtxR cell growth in vitro. The % of viable cells is shown 72 hours following treatment with ATL1101 or control oligonucleotide (ISIS 306064) at the indicated oligonucleotide concentrations of up to 250 nM.

The PC3 and Ptx-R PC3 cells were transfected at concentrations of IGF-IR antisense oligonucleotide (ATL1101) or control oligodeoxynucleotide (ISIS 306064) up to 250 nM or OTR control once per day on two sequential days. The number of viable PC3 and PtxR PC3 cells was determined 72 hours after the second transfection. The number of viable cells expressed as a % of control OTR viable cells is shown in FIG. 12. The PC3 Ptx-R cells retain ATL1101 sensitivity under standard culture conditions.

Figure 13:
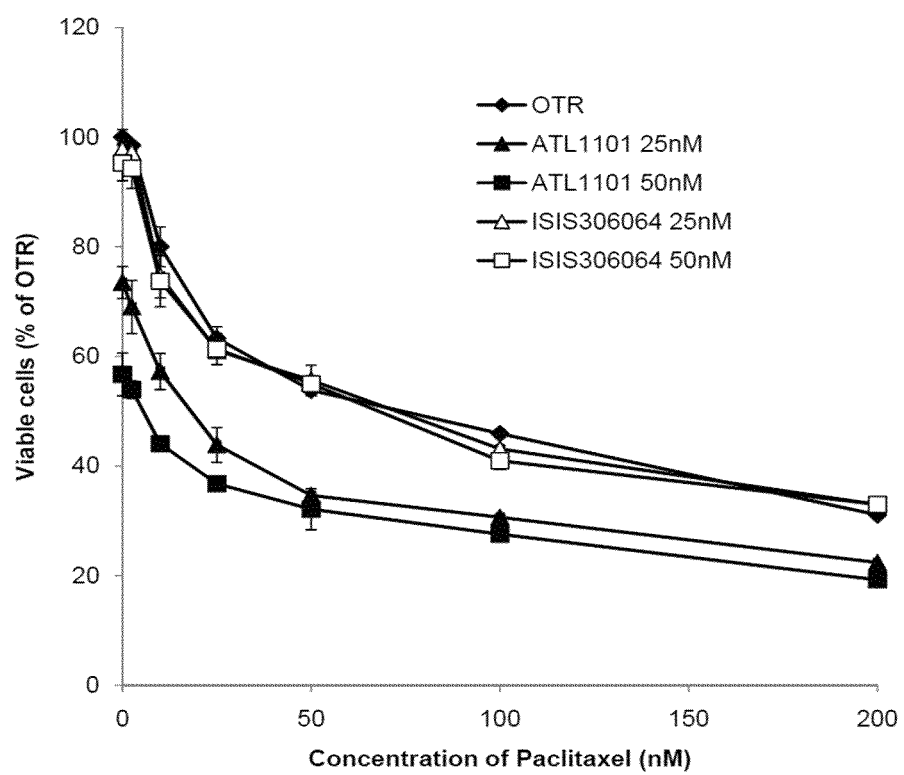
FIG. 13. Effect of ATL1101 treatment on PC3-PtxR cell growth in vitro. The % of viable cells is shown 72 hours following treatment with 25 and 50 nM ATL1101 or control oligonucleotide (ISIS 306064) after Paclitaxel treatment at the indicated Paclitaxel concentrations of up to 200 nM.

The PC3 and Ptx-R PC3 cell lines were transfected at 25 nM and 50 nM concentrations of IGF-IR antisense oligonucleotide (ATL1101) or control oligodeoxynucleotide (ISIS 306064) or OTR control once per day on two sequential days. After the second transfection, the PC3 and PC3 Ptx-R cells were treated with concentrations of Paclitaxel of up to 200 nM. The number of viable cells remaining was determined 72 hours after the second transfection treatment. The number of viable cells expressed as a % of control OTR viable cells is shown in FIGS. 13. ATL1101 treatment enhances the Ptx-R sensitivity to Paclitaxel under standard culture conditions. For example, there was approximately 45% cell viability with 100 nM Paclitaxel and 25 nM control oligodeoxynucleotide whereas, only 25 nM Paclitaxel is needed in the presence of 25 nM ATL1101 to produce the same reduction in cell viability.

Any discussion of documents, acts, materials, devices, articles or the like which has been included in the present specification is solely for the purpose of providing a context for the present invention and is not to be considered an admission that the prior art is in any way relevant to the present invention.

REFERENCES

Almeida and Allshire, *TRENDS Cell Biol.* 15:251-25, 2005
Altschul et al., *J. Mol. Biol.* 215:403-410, 1990
Arteaga et al., *J. Clin. Invest.* 84:1418-1423, 1989
Beaucage and Caruthers, *Tetrahedron Lett.* 22:1859-1862, 1981
Brazma and Vilo, *FEBS Lett.* 480:17-24, 2000
Carulli et al., *J. Cell Biochem. Suppl.* 31:286-296, 1998;
Celis et al., *FEBS Lett.* 480:2-16, 2000
Cher M L et al., *Proc Natl Acad Sci USA* 100:7847-7852, 2003
Cullen et al., *Cancer Res.* 49:7002-7009, 1990
Dahl et al., *Acta Chem. Scand.* 44:639-641, 1990
Elbashir et al., *Nature,* 411:494-498, 2001a
Elbashir et al., *Genes Dev.* 15:188-200, 2001b
Englisch et al., *Angewandte Chemie*, International Edition, 30:613, 1991
Fire et al., *Nature* 391:806-811, 1998
Foekens et al., *Cancer Res.* 49:7002-7009, 1989
Going and Gusterson, *Eur. J. Cancer* 35:1895-1904, 1999
Guo et al., *Gastroenterol.* 102:1101-1108, 1992
Guo and Kempheus, *Cell* 81:611-620, 1995
Haseloff and Gerlach, *Nature* 334:585-591, 1988
Jungblut et al., *Electrophoresis* 20:2100-2110, 1999
Jurecic and Belmont, *Curr. Opin. Microbiol.* 3:316-321, 2000
Kaiser et al., *Cancer Res. Clin. Oncol.* 119:665-668, 1993
Klein et al., *Exp. Neurol.* 150:183-194, 1998
Larson et al., *Cytometry* 41:203-208, 2000
Leung S Y et al., *Prostate* 44:156-163, 2000
Macauley et al., *Cancer Res.* 50:2511-2517, 1990
Madden et al., *Drug Discov. Today* 5:415-425, 2000
Matteucci and Caruthers, *J. Am. Chem. Soc.* 103:3185-3191, 1981
Millar and Waterhouse, *Funct. Integr. Genomics* 5:129-135, 2005
Montgomery et al., *Proc. Natl. Acad. Sci. USA.* 95:15502-15507, 1998
Moody et al., *Life Sciences* 52:1161-1173, 1993
McCulloch et al., *The Prostate* 9999:1-9, 2005
Pasquinelli et al., *Curr. Opin. Genet. Develop.* 15:200-205, 2005
Perriman et al., *Gene* 113:157-163, 1992
Pollak et al., *Cancer Lett.* 38:223-230, 1987
Prashar and Weissman, *Methods Enzymol.* 303:258-272, 1999
Remaole-Bennet et al., *J. Clin. Endocrinol. Metab.* 75:609-616, 1992
Ryan et al., *Urologic Oncology: Seminars and Original Investigations* 25:134-140, 2007
Scaringe, Ph.D. Thesis, University of Colorado, 1996
Scaringe et al., *J. Am. Chem. Soc.* 120:11820-11821; 1998
Shippy et al., *Mol. Biotech.* 12:117-129, 1999
Smith et al., *Nature* 407:319-320, 2000
Sutcliffe et al., *Proc. Natl. Acad. Sci. USA* 97:1976-1981, 2000
Tabara et al., *Science* 282:430-431, 1998
Tijsterman et al., *Science* 295:694-697, 2002
Timmons and Fire, *Nature* 395:854, 1998
Timmons et al., *Gene* 263:103-112, 2001
Tuschl et al., *Genes Dev./*3:3191-3197, 1999

Ullrich et al., *EMBO J.* 5:2503-2512, 1986
Ullrich et al., *Cell* 61:203-212, 1990
Waterhouse et al., *Proc. Natl. Acad. Sci. USA* 95:13959-13964, 1998
Zellweger T et al., *J. Pharmacology and Expt. Therapeutics* 298(3):934-940, 2001;
Zhang and Madden, *Genome Res.* 7:649-656, 1997.
Zolotukiin et al., *J. Virol.* 70(7):4646-4654, 1996

The invention claimed is:

1. A method for enhancing the sensitivity of an IGF-IR positive tumor or cancer cell to a taxane based agent in a subject, the method comprising:
   administering to a subject having a taxane based agent-resistant, IGF-IR positive tumor or cancer cell an effective amount of an agent that inhibits expression of IGF-IR.

2. The method of claim 1, wherein the tumor or cancer is a prostate tumor or prostate cancer.

3. The method of claim 1, wherein the taxane based agent is Docetaxol, Larotaxel, Ortataxel, Paclitaxel, or Tesetaxel.

4. The method of claim 1, wherein the agent that inhibits expression of IGF-IR is an antisense oligonucleotide that comprises a sequence as provided in SEQ ID NO:43, SEQ ID NO:50, SEQ ID NO:53, SEQ ID NO:68, SEQ ID NO:73, SEQ ID NO:110, SEQ ID NO:115, SEQ ID NO:116, SEQ ID NO:122, SEQ ID NO:124, SEQ ID NO:125, or SEQ ID NO:131.

5. The method of claim 4, wherein the agent that inhibits expression of IGF-IR is an antisense oligonucleotide that comprises a sequence as provided in SEQ ID NO:125.

6. The method of claim 1, wherein the method further comprises administering to the subject a taxane based agent.

7. The method of claim 1, wherein the agent is an antisense oligonucleotide.

8. The method of claim 7, wherein said oligonucleotide consists of 13 to 50 linked nucleosides.

9. The method of claim 7, wherein said oligonucleotide consists of 15 to 30 linked nucleosides.

10. The method of claim 7, wherein the oligonucleotide consists of 20 linked nucleosides.

11. The method of claim 7, wherein the antisense oligonucleotide comprises one or more of a modified internucleoside linkage, a modified sugar moiety, and a modified nucleobase.

12. The method of claim 7, wherein the antisense oligonucleotide comprises a modified internucleoside linkage.

13. The method of claim 7, wherein the antisense oligonucleotide comprises a modified sugar moiety.

14. The method of claim 7, wherein the antisense oligonucleotide comprises a modified nucleobase.

15. The method of claim 13, wherein the modified sugar moiety is selected from the group consisting of a 2'-O-(2-methoxyethyl), and a methylene ($-CH_2-$)$_n$ group bridging the 2' oxygen atom and the 4' carbon atom, wherein n is 1 or 2.

16. The method of claim 14, wherein the modified nucleobase is a 5-methylcytosine.

17. The method of claim 7, wherein the antisense oligonucleotide comprises: a gap segment consisting of linked deoxynucleosides; a 5' wing segment consisting of linked nucleosides; a 3' wing segment consisting of linked nucleosides; wherein the gap segment is positioned between the 5' wing segment and the 3' wing segment and wherein each nucleoside of each wing segment comprises a modified sugar.

18. The method of claim 7, wherein the antisense oligonucleotide comprises: a gap segment consisting of ten linked deoxynucleosides; a 5' wing segment consisting of five linked nucleosides; a 3' wing segment consisting of five linked nucleosides; wherein the gap segment is positioned between the 5' wing segment and the 3' wing segment, wherein each nucleoside of each wing segment comprises a 2'-O-methoxyethyl sugar; wherein each cytosine in said oligonucleotide is a 5-methylcytosine, and wherein each internucleoside linkage of said oligonucleotide is a phosphorothioate linkage.

19. The method of claim 8, wherein the antisense oligonucleotide consists of 20 linked nucleosides.

20. The method of claim 12, wherein the modified internucleoside linkage comprises a phosphorothioate.

21. The method of claim 11, wherein the antisense oligonucleotide comprises a modified internucleoside linkage and a modified sugar.

* * * * *

```
                         SEQUENCE LISTING

<160> NUMBER OF SEQ ID NOS: 136

<210> SEQ ID NO 1
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 1 cctttattt gggatgaaat                                                   20

<210> SEQ ID NO 2
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 2
ccagacttca ttccttttat                                                  20

<210> SEQ ID NO 3
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 3
tgatagtcgt tgcggatgtc                                                  20

<210> SEQ ID NO 4
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 4
gctgctgata gtcgttgcgg                                                  20

<210> SEQ ID NO 5
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 5
cttcagctgc tgatagtcgt                                                  20

<210> SEQ ID NO 6
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 6
ccctcgatca ccgtgcagtt                                                  20
```

```
<210> SEQ ID NO 7
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 7
ttggagatga gcaggatgtg                                                    20

<210> SEQ ID NO 8
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 8
cggccttgga gatgagcagg                                                    20

<210> SEQ ID NO 9
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 9
gtcctcggcc ttggagatga                                                    20

<210> SEQ ID NO 10
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 10
cggtagtcct cggccttgga                                                    20

<210> SEQ ID NO 11
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 11
ttgtagaaga gtttccagcc                                                    20

<210> SEQ ID NO 12
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 12
tggtcatctc gaagatgacc                                                    20

<210> SEQ ID NO 13
<211> LENGTH: 20
<212> TYPE: DNA
<213> ORGANISM: Artificial Sequence
<220> FEATURE:
```

```
<223> OTHER INFORMATION: antisense oligonucleotide

<400> SEQUENCE: 13
gagattggtc atctcgaaga                                               20

<210> SEQ ID NO 14
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 14
tccttgagat tggtcatctc                                               20

<210> SEQ ID NO 15
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 15
caatatcctt gagattggtc                                               20

<210> SEQ ID NO 16
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 16
aagcccaata tccttgagat                                               20

<210> SEQ ID NO 17
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 17
cccccgagta atgttcctca                                               20

<210> SEQ ID NO 18
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 18
tctcaatcct gatggccccc                                               20

<210> SEQ ID NO 19
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 19
gttattggac accgcatcca                                               20
```

```
<210> SEQ ID NO 20
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 20
atgtagttat tggacaccgc                                              20

<210> SEQ ID NO 21
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 21
ccacaatgta gttattggac                                              20

<210> SEQ ID NO 22
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 22
cacaggtccc cacattcctt                                              20

<210> SEQ ID NO 23
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 23
ctggacacag gtccccacat                                              20

<210> SEQ ID NO 24
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 24
atggtggtct tctcacacat                                              20

<210> SEQ ID NO 25
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 25
tgttgatggt ggtcttctca                                              20

<210> SEQ ID NO 26
<211> LENGTH: 20
<212> TYPE: DNA
<213> ORGANISM: Artificial Sequence
<220> FEATURE:
<223> OTHER INFORMATION: antisense oligonucleotide
```

```
<400> SEQUENCE: 26
ctcattgttg atggtggtct                                            20

<210> SEQ ID NO 27
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 27
gttgtactca ttgttgatgg                                            20

<210> SEQ ID NO 28
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 28
cggtagttgt actcattgtt                                            20

<210> SEQ ID NO 29
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 29
agcagcggta gttgtactca                                            20

<210> SEQ ID NO 30
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 30
ggtccagcag cggtagttgt                                            20

<210> SEQ ID NO 31
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 31
tttgtggtcc agcagcggta                                            20

<210> SEQ ID NO 32
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 32
tgggcacatt ttctggcagc                                            20

<210> SEQ ID NO 33
<211> LENGTH: 20
```

```
<212> TYPE: DNA
<213> ORGANISM: Artificial Sequence
<220> FEATURE:
<223> OTHER INFORMATION: antisense oligonucleotide

<400> SEQUENCE: 33
ggagtaattc ccttctagct                                                 20

<210> SEQ ID NO 34
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 34
tcccacagtt gctgcaagtt                                                 20

<210> SEQ ID NO 35
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 35
atgttccagc tgttggagcc                                                 20

<210> SEQ ID NO 36
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 36
ccaccatgtt ccagctgttg                                                 20

<210> SEQ ID NO 37
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 37
gtccagggct tcagcccatg                                                 20

<210> SEQ ID NO 38
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 38
gtgagggtca cagccttgac                                                 20

<210> SEQ ID NO 39
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 39
```
ccatggtgag ggtcacagcc                                              20

<210> SEQ ID NO 40
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 40
ttggtgcgaa tgtacaagat                                              20

<210> SEQ ID NO 41
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 41
attttgtctt tggagcagta                                              20

<210> SEQ ID NO 42
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 42
aggaaattct caaagacttt                                              20

<210> SEQ ID NO 43
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 43
ctgcttcggc tggacatggt                                              20

<210> SEQ ID NO 44
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 44
tgttcctgct tcggctggac                                              20

<210> SEQ ID NO 45
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 45
ctgctctcaa agaaagggta                                              20

<210> SEQ ID NO 46
<211> LENGTH: 20
<212> TYPE: DNA
<213> ORGANISM: Artificial Sequence

```
<220> FEATURE:
<223> OTHER INFORMATION: antisense oligonucleotide

<400> SEQUENCE: 46
ccactctgct ctcaaagaaa                                           20

<210> SEQ ID NO 47
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 47
gttatccact ctgctctcaa                                           20

<210> SEQ ID NO 48
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 48
tccttgttat ccactctgct                                           20

<210> SEQ ID NO 49
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 49
ttgcagctgt ggatatcgat                                           20

<210> SEQ ID NO 50
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 50
cgtggttgca gctgtggata                                           20

<210> SEQ ID NO 51
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 51
agcctcgtgg ttgcagctgt                                           20

<210> SEQ ID NO 52
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 52
ttctcagcct cgtggttgca                                           20
```

```
<210> SEQ ID NO 53
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 53
ccagcttctc agcctcgtgg                                              20

<210> SEQ ID NO 54
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 54
gcagcccagc ttctcagcct                                              20

<210> SEQ ID NO 55
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 55
gcgctgcagc ccagcttctc                                              20

<210> SEQ ID NO 56
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 56
tttaaaaaga tggagttttc                                              20

<210> SEQ ID NO 57
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 57
gccactttaa aaagatggag                                              20

<210> SEQ ID NO 58
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 58
tcctgtctgg acacacattc                                              20

<210> SEQ ID NO 59
<211> LENGTH: 20
<212> TYPE: DNA
<213> ORGANISM: Artificial Sequence
<220> FEATURE:
<223> OTHER INFORMATION: antisense oligonucleotide
```

```
<400> SEQUENCE: 59
aagaacacag gatctgtcca                                              20

<210> SEQ ID NO 60
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 60
catagaagaa cacaggatct                                              20

<210> SEQ ID NO 61
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 61
ggaacgtaca catcagcagc                                              20

<210> SEQ ID NO 62
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 62
actccttcat agaccatccc                                              20

<210> SEQ ID NO 63
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 63
cggagataac ttttgagatc                                              20

<210> SEQ ID NO 64
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 64
gagaccggag ataactttg                                               20

<210> SEQ ID NO 65
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 65
attttgactg tgaaatcttc                                              20

<210> SEQ ID NO 66
```

```
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 66
gcgatctccc agaggacgac                                                 20

<210> SEQ ID NO 67
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 67
tgtagtagaa ggagacctcc                                                 20

<210> SEQ ID NO 68
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 68
gccttgtgtc ctgagtgtct                                                 20

<210> SEQ ID NO 69
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 69
atccaaggat cagcaggtcg                                                 20

<210> SEQ ID NO 70
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 70
gctgcttgca tattgaaaaa                                                 20

<210> SEQ ID NO 71
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 71
aaaaagctgc ttgcatattg                                                 20

<210> SEQ ID NO 72
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 72
```

```
gcccatgtca gttaagggtt                                          20

<210> SEQ ID NO 73
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 73
ccagcgtgtc tctcaaatgg                                          20

<210> SEQ ID NO 74
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 74
ggagtttaaa ggacagtgcc                                          20

<210> SEQ ID NO 75
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 75
catcactgac ctctttctat                                          20

<210> SEQ ID NO 76
<211> LENGTH: 1651
<212> TYPE: DNA
<213> ORGANISM: Homo sapiens

<400> SEQUENCE: 76
aagcttttca agaaccgggg aaacgcgctt tccagccgcg ctgttgttgt tttcaatgaa    60
cctctcccag ccccgcactc cccgcccacc cctcccctct cctgcccacc cctcccctct   120
cctgcccacc cctcccctgc ctagcctttc cctggctacc caccctgcc ccgccgagac    180 cggaccggcg gcgggggcat tgtttttgga gtcgggcggg aggggagggc gcgtgcgggg   240
tggccggcgc agtgcggtgg gggcgggagc gggtgggcac gcgcgcgtgt ctctgtgtgc   300
gcgcgggagg cggtggggcg ggagatgggg cggcgcctc gcagtctcgc gccccacgcc    360
cgggctccgc tccgcacgtc ttggggaacc cgggctccgg tttttttgcgc gcgccggcct  420 gggccgggcc ctcggcgcgc cgctgctcgg cggtggccgc tcgagtgtgc gagcgggcgc   480
gtgtgcgcgg gccagggcgc cgcgcgcgcg agccccagt gtgtggcagc ggcggcggcg    540
gcgcggcgag gctgggctc ttgtttacca gcattaactc gctgagcgga aaaaaaagg    600 gaaaaaccc gaggaggagc gagcgcacca ggcgaactcg agagaggcgg gagagcgaga   660
gggacgccgc cagcgagcct gcccacggcc ggcgctcgca gacccctcggc cccgctcccc   720 ggatccccc gcgccctcca cgcccctccc gcgcggggc agctccacgg cgcgcctcgc    780
ctcggctgtg accttcagcg agccggagcc cccgcgcaga gcaggcggcg gcgggcgggg   840
gccgggcggg ggccggcgcg gggcgggcgg cggcgcagag ccgggcggcg cggcgggagt   900
gctgagcgcg gcgcggccgg cccgccgctt tgtgtgtgtc ctggatttgg gaaggagctc   960
```

-continued

| | |
|---|---|
| gccgcggcgg cggcgctgag ggaggaggcg gcggcgagcg gagccaggag gaggaggagg | 1020 |
| aggaggggga gccgctcatt cattttgact ccgcgtttct gccccctcgcc ggcctcgcct | 1080 |
| gtgacccgga cttcggggcg atcttgcgaa ctgcgtcgcg ccctcccgcg gcggaagctc | 1140 |
| gggcgtccgg ccgcctcccg cgcgccaggg ccgggcttgt ttttcctcgc ctaggcagat | 1200 |
| ttgggctttg ccccctttct ttgcagtttt ccccccttcc tgcctctccg ggtttgaaaa | 1260 |
| tggaggccga cgacgccgac agcccgcccc ggcgcgcctc gggttcccga ctccgccgag | 1320 |
| ccctgggccg ctgctgccgg cgctgagggg ccgccccgcg ccgcccgccc cgtccgcgca | 1380 |
| cccgagggc cccggcggcg gcccttcgga gtattgtttc cttcgccctt gttttttggag | 1440 |
| ggggagcgaa gactgagttt gagacttgtt tcctttcatt tccttttttt cttttctttt | 1500 |
| ctttttttt tttttttttt tttttgagaa aggggaattt catcccaaat aaaaggaatg | 1560 |
| aagtctggct ccggaggagg gtccccgacc tcgctgtggg ggctcctgtt tctctccgcc | 1620 |
| gcgctctcgc tctggccgac gagtggagaa a | 1651 |

<210> SEQ ID NO 77
<211> LENGTH: 4989
<212> TYPE: DNA
<213> ORGANISM: Homo sapiens

<400> SEQUENCE: 77

| | |
|---|---|
| tttttttttt ttttgagaaa gggaatttca tcccaaataa aaggaatgaa gtctggctcc | 60 |
| ggaggagggt ccccgacctc gctgtggggg ctcctgtttc tctccgccgc gctctcgctc | 120 |
| tggccgacga gtggagaaat ctgcgggcca ggcatcgaca tccgcaacga ctatcagcag | 180 |
| ctgaagcgcc tggagaactg cacggtgatc gagggctacc tccacatcct gctcatctcc | 240 |
| aaggccgagg actaccgcag ctaccgcttc cccaagctca cggtcattac cgagtacttg | 300 |
| ctgctgttcc gagtggctgg cctcgagagc ctcggagacc tcttccccaa cctcacggtc | 360 |
| atccgcggct ggaaactctt ctacaactac gccctggtca tcttcgagat gaccaatctc | 420 |
| aaggatattg ggctttacaa cctgaggaac attactcggg gggccatcag gattgagaaa | 480 |
| aatgctgacc tctgttacct ctccactgtg gactggtccc tgatcctgga tgcggtgtcc | 540 |
| aataactaca ttgtggggaa taagccccca aaggaatgtg gggacctgtg tccagggacc | 600 |
| atggaggaga gccgatgtg tgagaagacc accatcaaca atgagtacaa ctaccgctgc | 660 |
| tggaccacaa accgctgcca gaaaatgtgc ccaagcacgt gtgggaagcg ggcgtgcacc | 720 |
| gagaacaatg agtgctgcca ccccgagtgc ctgggcagct gcagcgcgcc tgacaacgac | 780 |
| acggcctgtg tagcttgccg ccactactac tatgccggtg tctgtgtgcc tgcctgcccg | 840 |
| cccaacacct acaggtttga gggctggcgc tgtgtggacc gtgacttctg cgccaacatc | 900 |
| ctcagcgccg agagcagcga ctccgagggg tttgtgatcc acgacggcga gtgcatgcag | 960 |
| gagtgcccct cgggcttcat ccgcaacggc agccagagca tgtactgcat cccttgtgaa | 1020 |
| ggtccttgcc cgaaggtctg tgaggaagaa aagaaaacaa agaccattga ttctgttact | 1080 |
| tctgctcaga tgctccaagg atgcaccatc ttcaagggca atttgctcat taacatccga | 1140 |
| cgggggaata acattgcttc agagctggag aacttcatgg ggctcatcga ggtggtgacg | 1200 |
| ggctacgtga agatccgcca ttctcatgcc ttggtctcct tgtccttcct aaaaaacctt | 1260 |
| cgcctcatcc taggagagga gcagctagaa gggaattact ccttctacgt cctcgacaac | 1320 |
| cagaacttgc agcaactgtg ggactggacc accgcaacc tgaccatcaa gcagggaaa | 1380 |
| atgtactttg ctttcaatcc caaattatgt gtgtttccgaaa tttaccgcat ggaggaagtg | 1440 |

```
acgggyacta aagggcgcca aagcaaaggg gacataaaca ccaggaacaa cggggagaga    1500
gcctcctgtg aaagtgacgt cctgcatttc acctccacca ccacgtcgaa gaatcgcatc    1560
atcataacct ggcaccggta ccggccccct gactacaggg atctcatcag cttcaccgtt    1620
tactacaagg aagcaccctt taagaatgtc acagagtatg atgggcagga tgcctgcggc    1680
tccaacagct ggaacatggt ggacgtggac ctcccgccca acaaggacgt ggagcccggc    1740
atcttactac atgggctgaa gccctggact cagtacgccg tttacgtcaa ggctgtgacc    1800
ctcaccatgg tggagaacga ccatatccgt ggggccaaga gtgagatctt gtacattcgc    1860
accaatgctt cagttccttc cattcccttg gacgttcttt cagcatcgaa ctcctcttct    1920
cagttaatcg tgaagtggaa ccctccctct ctgcccaacg gcaacctgag ttactacatt    1980
gtgcgctggc agcggcagcc tcaggacggc tacctttacc ggcacaatta ctgctccaaa    2040
gacaaaatcc ccatcaggaa gtatgccgac ggcaccatcg acattgagga ggtcacagag    2100
aacccccaaga ctgaggtgtg tggtggggag aaagggcctt gctgcgcctg ccccaaaact    2160
gaagccgaga agcaggccga aaggaggag gctgaatacc gcaaagtctt tgagaatttc    2220
ctgcacaact ccatcttcgt gcccagacct gaaaggaagc ggagagatgt catgcaagtg    2280
gccaacacca ccatgtccag ccgaagcagg aacaccacgg ccgcagacac ctacaacatc    2340
accgacccgg aagagctgga gacagagtac ccttttctttg agagcagagt ggataacaag    2400
gagagaactg tcatttctaa ccttcggcct ttcacattgt accgcatcga tatccacagc    2460
tgcaaccacg aggctgagaa gctgggctgc agcgcctcca acttcgtctt tgcaaggact    2520
atgcccgcag aaggagcaga tgacattcct gggccagtga cctgggagcc aaggcctgaa    2580
aactccatct tttaaagtg gccggaacct gagaatccca atggattgat tctaatgtat    2640
gaaataaaat acgatcaca agttgaggat cagcgagaat gtgtgtccag acaggaatac    2700
aggaagtatg gaggggccaa gctaaaccgg ctaaacccgg ggaactacac agcccggatt    2760
caggccacat ctctctctgg gaatgggtcg tggacagatc ctgtgttctt ctatgtccag    2820
gccaaaacag gatatgaaaa cttcatccat ctgatcatcg ctctgcccgt cgctgtcctg    2880
ttgatcgtgg gagggttggt gattatgctg tacgtcttcc atagaaagag aaataacagc    2940
aggctgggga atggagtgct gtatgcctct gtgaacccgg agtacttcag cgctgctgat    3000
gtgtacgttc ctgatgagtg ggaggtgcgt cgggagaaga tcaccatgag ccgggaactt    3060
gggcagggt cgtttgggat ggtctatgaa ggagttgcca agggtgtggt gaaagatgaa    3120
cctgaaacca gagtggccat taaaacagtc aacgaggccg caagcatgcg tgagaggatt    3180
gagtttctca acgaagcttc tgtgatgaag gagttcaatt gtcaccatgt ggtgcgattg    3240
ctgggtgtgt tgtcccaagg ccagccaaca ctggtcatca tggaactgat gacacggggc    3300
gatctcaaaa gttatctccg gtctctgagg ccagaaatgg agaataatcc agtcctagca    3360
cctccaagcc tgagcaagat gattcagatg gccggagaga ttgcagacgg catggcatac    3420
ctcaacgcca ataagttcgt ccacagagac cttgctgccc ggaattgcat ggtagccgaa    3480
gatttcacag tcaaaatcgg agattttggt atgacgcgag atatctatga gacagactat    3540
taccggaaag gaggcaaagg gctgctgccc gtgcgctgga tgtctcctga gtccctcaag    3600
gatggagtct tcaccactta ctcggacgtc tggtccttcg gggtcgtcct ctgggagatc    3660
gccacactgg ccgagcagcc ctaccaggc ttgtccaacg agcaagtcct tcgcttcgtc    3720
atggagggcg gccttctgga caagccagac aactgtcctg acatgctgtt tgaactgatg    3780
```

| | |
|---|---|
| cgcatgtgct ggcagtataa ccccaagatg aggccttcct tcctggagat catcagcagc | 3840 |
| atcaaagagg agatggagcc tggcttccgg gaggtctcct tctactacag cgaggagaac | 3900 |
| aagctgcccg agccggagga gctggacctg gagccagaga acatggagag cgtccccctg | 3960 |
| gacccctcgg cctcctcgtc ctccctgcca ctgcccgaca dacactcagg acacaaggcc | 4020 |
| gagaacggcc ccggccctgg ggtgctggtc ctccgcgcca gcttcgacga gagacagcct | 4080 |
| tacgcccaca tgaacggggg ccgcaagaac gagcgggccc tgccgctgcc ccagtcttcg | 4140 |
| acctgctgat ccttggatcc tgaatctgtg caaacagtaa cgtgtgcgca cgcgcagcgg | 4200 |
| ggtgggggggg gagagagagt tttaacaatc cattcacaag cctcctgtac ctcagtggat | 4260 |
| cttcagttct gcccttgctg cccgcgggag acagcttctc tgcagtaaaa cacatttggg | 4320 |
| atgttccttt tttcaatatg caagcagctt tttattccct gcccaaaccc ttaactgaca | 4380 |
| tgggcctttta agaaccttaa tgacaacact taatagcaac agagcacttg agaaccagtc | 4440 |
| tcctcactct gtccctgtcc ttccctgttc tcccttctc tctcctctct gcttcataac | 4500 |
| ggaaaaataa ttgccacaag tccagctggg aagcccttt tatcagtttg aggaagtggc | 4560 |
| tgtccctgtg gccccatcca accactgtac acacccgcct gacaccgtgg gtcattacaa | 4620 |
| aaaaacacgt ggagatggaa atttttacct ttatctttca cctttctagg gacatgaaat | 4680 |
| ttacaaaggg ccatcgttca tccaaggctg ttaccatttt aacgctgcct aattttgcca | 4740 |
| aaatcctgaa ctttctccct catcggcccg gcgctgatte tcgtgtccg gaggcatggg | 4800 |
| tgagcatggc agctggttgc tccatttgag agacacgctg gcgacacact ccgtccatcc | 4860 |
| gactgccct gctgtgctgc tcaaggccac aggcacacag gtctcattgc ttctgactag | 4920 |
| attattattt gggggaactg gacacaatag gtctttctct cagtgaaggt ggggagaagc | 4980 |
| tgaaccggc | 4989 |

```
<210> SEQ ID NO 78
<211> LENGTH: 15
<212> TYPE: RNA
<213> ORGANISM: Artificial Sequence
<220> FEATURE:
<223> OTHER INFORMATION: Nucleotide sequence encoding IGF-IR C5 propyne
      antisense compound CAC AGU UGC UGC AAG

<400> SEQUENCE: 78
```

| | |
|---|---|
| cacaguugcu gcaag | 15 |

```
<210> SEQ ID NO 79
<211> LENGTH: 20
<212> TYPE: DNA
<213> ORGANISM: Artificial Sequence
<220> FEATURE:
<223> OTHER INFORMATION: antisense oligonucleotide control to human
      H-ras

<400> SEQUENCE: 79
```

| | |
|---|---|
| tccgtcatcg ctcctcaggg | 20 |

```
<210> SEQ ID NO 80
<211> LENGTH: 20
<212> TYPE: DNA
<213> ORGANISM: Artificial Sequence
<220> FEATURE:
<223> OTHER INFORMATION: antisense oligonucleotide control to human JNK

<400> SEQUENCE: 80
```

| | |
|---|---|
| gtgcgcgcga gcccgaaatc | 20 |

<210> SEQ ID NO 81
<211> LENGTH: 20
<212> TYPE: DNA
<213> ORGANISM: Artificial Sequence
<220> FEATURE:
<223> OTHER INFORMATION: antisense oligonucleotide control to mouse and
      rat c-raf

<400> SEQUENCE: 81
atgcattctg cccccaagga                                           20

<210> SEQ ID NO 82
<211> LENGTH: 21
<212> TYPE: DNA
<213> ORGANISM: Artificial Sequence
<220> FEATURE:
<223> OTHER INFORMATION: PCR primer to hIGF-RI

<400> SEQUENCE: 82
ccctttcttt gcagttttcc c                                         21

<210> SEQ ID NO 83
<211> LENGTH: 17
<212> TYPE: DNA
<213> ORGANISM: Artificial Sequence
<220> FEATURE:
<223> OTHER INFORMATION: PCR primer to hIGF-RI

<400> SEQUENCE: 83
cgtcgtcggc ctccatt                                              17

<210> SEQ ID NO 84
<211> LENGTH: 23
<212> TYPE: DNA
<213> ORGANISM: Artificial Sequence
<220> FEATURE:
<223> OTHER INFORMATION: PCR primer to hIGF-RI

<400> SEQUENCE: 84
ccttcctgcc tctccgggtt tga                                       23

<210> SEQ ID NO 85
<211> LENGTH: 20
<212> TYPE: DNA
<213> ORGANISM: Artificial Sequence
<220> FEATURE:
<223> OTHER INFORMATION: IGF-IR mRNA target sequence

<400> SEQUENCE: 85
tccgggtttg aaaatggagg                                           20

<210> SEQ ID NO 86
<211> LENGTH: 20
<212> TYPE: DNA
<213> ORGANISM: Artificial Sequence
<220> FEATURE:
<223> OTHER INFORMATION: IGF-IR mRNA target sequence

<400> SEQUENCE: 86
gaagactgag tttgagactt                                           20

<210> SEQ ID NO 87
<211> LENGTH: 20
<212> TYPE: DNA
<213> ORGANISM: Artificial Sequence

```
<220> FEATURE:
<223> OTHER INFORMATION: IGF-IR mRNA target sequence

<400> SEQUENCE: 87
tgaaaatgga ggccgacgac                                                   20

<210> SEQ ID NO 88
<211> LENGTH: 20
<212> TYPE: DNA
<213> ORGANISM: Artificial Sequence
<220> FEATURE:
<223> OTHER INFORMATION: IGF-IR mRNA target sequence

<400> SEQUENCE: 88
cggctgtgac cttcagcgag                                                   20

<210> SEQ ID NO 89
<211> LENGTH: 20
<212> TYPE: DNA
<213> ORGANISM: Artificial Sequence
<220> FEATURE:
<223> OTHER INFORMATION: IGF-IR mRNA target sequence

<400> SEQUENCE: 89
ggctgtgacc ttcagcgagc                                                   20

<210> SEQ ID NO 90
<211> LENGTH: 20
<212> TYPE: DNA
<213> ORGANISM: Artificial Sequence
<220> FEATURE:
<223> OTHER INFORMATION: IGF-IR mRNA target sequence

<400> SEQUENCE: 90
tcggagtatt gtttccttcg                                                   20

<210> SEQ ID NO 91
<211> LENGTH: 20
<212> TYPE: DNA
<213> ORGANISM: Artificial Sequence
<220> FEATURE:
<223> OTHER INFORMATION: IGF-IR mRNA target sequence

<400> SEQUENCE: 91
gggggagccg ctcattcatt                                                   20

<210> SEQ ID NO 92
<211> LENGTH: 21
<212> TYPE: DNA
<213> ORGANISM: Artificial Sequence
<220> FEATURE:
<223> OTHER INFORMATION: exemplified antisense strand

<400> SEQUENCE: 92
cgagaggcgg acgggaccgt t                                                 21

<210> SEQ ID NO 93
<211> LENGTH: 21
<212> TYPE: DNA
<213> ORGANISM: Artificial Sequence
<220> FEATURE:
<223> OTHER INFORMATION: exemplified sense strand

<400> SEQUENCE: 93
ttgctctccg cctgccctgg c                                                 21
```

<210> SEQ ID NO 94
<211> LENGTH: 19
<212> TYPE: DNA
<213> ORGANISM: Artificial Sequence
<220> FEATURE:
<223> OTHER INFORMATION: PCR primer for hGAPDH

<400> SEQUENCE: 94
gaaggtgaag gtcggagtc                                                19

<210> SEQ ID NO 95
<211> LENGTH: 20
<212> TYPE: DNA
<213> ORGANISM: Artificial Sequence
<220> FEATURE:
<223> OTHER INFORMATION: PCR primer for hGAPDH

<400> SEQUENCE: 95
gaagatggtg atgggatttc                                               20

<210> SEQ ID NO 96
<211> LENGTH: 20
<212> TYPE: DNA
<213> ORGANISM: Artificial Sequence
<220> FEATURE:
<223> OTHER INFORMATION: PCR probe to hGAPDH

<400> SEQUENCE: 96
caagcttccc gttctcagcc                                               20

<210> SEQ ID NO 97
<211> LENGTH: 5983
<212> TYPE: DNA
<213> ORGANISM: Homo sapiens

<400> SEQUENCE: 97
agtgtgtggc agcggcggcg gcggcgcggc gaggctgggg ctcttgttta ccagcattaa    60
ctcgctgagc ggaaaaaaaa agggaaaaaa cccgaggagg agcgagcgca ccaggcgaac   120
tcgagagagg cgggagagcg agagggacgc cgccagcgag cctgcccacg gccggcgctc   180
gcagaccctc ggccccgctc cccggatccc cccgcgccct ccacgcccct cccgcgcggg   240
ggcagctcca cggcgcgcct cgcctcggct gtgaccttca gcgagccgga gccccgcgc    300 agagcaggcg gcggcgggcg ggggccgggc ggggccggc gcggggcggg cggcggcgca    360
gagccgggcg gcgcggcggg agtgctgagc gcggcgcggc cggcccgccg ctttgtgtgt   420
gtcctggatt tgggaaggag ctcgccgcgg cggcggcgct gagggaggag gcggcggcga   480
gcggagccag gaggaggagg aggaggaggg ggagccgctc attcattttg actccgcgtt   540 tctgccccctc gccggcctcg cctgtgaccc ggacttcggg gcgatcttgc gaactgcgtc   600
gcgccctccc gcggcggaag ctcgggcgtc cggccgcctc ccgcgcgcca gggccgggct   660 tgttttttcct cgcctaggca gatttgggct ttgccccctt tctttgcagt ttcccccct    720 tcctgcctct ccgggtttga aaatggaggc cgacgacgcc gacagcccgc ccggcgcgc    780 ctcgggttcc cgactccgcc gagccctggg ccgctgctgc cggcgctgag gggccgcccc   840
gcgccgcccg ccccgtccgc gcaccccgag ggccccggcg gcggcccttc ggagtattgt    900
ttccttcgcc cttgtttttg gagggggagc gaagactgag tttgagactt gtttcctttc   960
atttcctttt tttctttttct ttctttttt ttttttttt tttttttga gaaagggaat   1020 ttcatcccaa ataaaaggaa tgaagtctgg ctccggagga gggtccccga cctcgctgtg   1080

```
ggggctcctg tttctctccg ccgcgctctc gctctggccg acgagtggag aaatctgcgg    1140
gccaggcatc gacatccgca acgactatca gcagctgaag cgcctggaga actgcacggt    1200
gatcgagggc tacctccaca tcctgctcat ctccaaggcc gaggactacc gcagctaccg    1260
cttccccaag ctcacggtca ttaccgagta cttgctgctg ttccgagtgg ctggcctcga    1320
gagcctcgga gacctcttcc ccaacctcac ggtcatccgc ggctggaaac tcttctacaa    1380
ctacgccctg gtcatcttcg agatgaccaa tctcaaggat atttgggcttt acaacctgag    1440
```

```
gcctttcaca ttgtaccgca tcgatatcca cagctgcaac cacgaggctg agaagctggg    3480
ctgcagcgcc tccaacttcg tctttgcaag gactatgccc gcagaaggag cagatgacat    3540
tcctgggcca gtgacctggg agccaaggcc tgaaaactcc atcttttta agtggccgga     3600 acctgagaat cccaatggat tgattctaat gtatgaaata aaatacggat cacaagttga    3660
ggatcagcga gaatgtgtgt ccagacagga atacaggaag tatggagggg ccaagctaaa    3720
ccggctaaac ccggggaact acacagcccg gattcaggcc acatctctct ctggaatgg     3780 gtcgtggaca gatcctgtgt tcttctatgt ccaggccaaa acaggatatg aaaacttcat    3840
ccatctgatc atcgctctgc ccgtcgctgt cctgttgatc gtgggagggt tggtgattat    3900
gctgtacgtc ttccatagaa agagaaataa cagcaggctg gggaatggag tgctgtatgc    3960
ctctgtgaac ccggagtact tcagcgctgc tgatgtgtac gttcctgatg agtgggaggt    4020
ggctcgggag aagatcacca tgagccggga acttgggcag gggtcgtttg gatggtcta    4080 tgaaggagtt gccaagggtg tggtgaaaga tgaacctgaa accagagtgg ccattaaaac    4140
agtgaacgag gccgcaagca tgcgtgagag gattgagttt ctcaacgaag cttctgtgat    4200
gaaggagttc aattgtcacc atgtggtgcg attgctgggt gtggtgtccc aaggccagcc    4260
aacactggtc atcatggaac tgatgacacg gggcgatctc aaaagttatc tccggtctct    4320
gaggccagaa atggagaata atccagtcct agcacctcca agcctgagca agatgattca    4380
gatgccggga gagattgcag acggcatggc atacctcaac gccaataagt tcgtccacag    4440
agaccttgct gcccggaatt gcatggtagc cgaagatttc acagtcaaaa tcggagattt    4500
tggtatgacg cgagatatct atgagacaga ctattaccgg aaaggaggca aagggctgct    4560
gcccgtgcgc tggatgtctc ctgagtccct caaggatgga gtcttcacca cttactcgga    4620
cgtctggtcc ttcggggtcg tcctctggga gatcgccaca ctggccgagc agccctacca    4680
gggcttgtcc aacgagcaag tccttcgctt cgtcatggag ggcggccttc tggacaagcc    4740
agacaactgt cctgacatgc tgtttgaact gatgcgcatg tgctggcagt ataaccccaa    4800
gatgaggcct tccttcctgg agatcatcag cagcatcaaa gaggagatgg agcctggctt    4860
ccgggaggtc tccttctact acagcgagga gaacaagctg cccgagccgg aggagctgga    4920
cctggagcca gagaacatgg agagcgtccc cctggacccc tcggcctcct cgtcctccct    4980
gccactgccc gacagacact caggacacaa ggccgagaac ggccccggcc ctggggtgct    5040
ggtcctccgc gccagcttcg acgagagaca gccttacgcc cacatgaacg ggggccgcaa    5100
gaacgagcgg gccttgccgc tgccccagtc ttcgacctgc tgatccttgg atcctgaatc    5160
tgtgcaaaca gtaacgtgtg cgcacgcgca gcggggtggg gggggagaga gagttttaac    5220
aatccattca caagcctcct gtacctcagt ggatcttcag ttctgccctt gctgcccgcg    5280
ggagacagct tctctgcagt aaaacacatt tgggatgttc cttttttcaa tatgcaagca    5340
gctttttatt ccctgcccaa acccttaact gacatgggcc tttaagaacc ttaatgacaa    5400
cacttaatag caacagagca cttgagaacc agtctcctca ctctgtccct gtccttccct    5460
gttctccctt tctctctcct ctctgcttca taacggaaaa ataattgcca caagtccagc    5520
tgggaagccc tttttatcag tttgaggaag tggctgtccc tgtggcccca tccaaccact    5580
gtacacaccc gcctgacacc gtgggtcatt acaaaaaaac acgtggagat ggaaattttt    5640
acctttatct ttcacctttc tagggacatg aaatttacaa agggccatcg ttcatccaag    5700
gctgttacca ttttaacgct gcctaatttt gccaaaatcc tgaactttct ccctcatcgg    5760
cccggcgctg attcctcgtg tccggaggca tgggtgagca tggcagctgg ttgctccatt    5820
```

```
tgagagacac gctggcgaca cactccgtcc atccgactgc ccctgctgtg ctgctcaagg      5880
ccacaggcac acaggtctca ttgcttctga ctagattatt atttggggga actggacaca      5940
ataggtcttt ctctcagtga aggtggggag aagctgaacc ggc                        5983
```

<210> SEQ ID NO 98
<211> LENGTH: 391
<212> TYPE: PRT
<213> ORGANISM: Homo sapiens

<400> SEQUENCE: 98

```
Asn Pro Glu Tyr Phe Ser Ala Ala Asp Val Tyr Val Pro Asp Glu Trp
1               5                   10                  15

Glu Val Ala Arg Glu Lys Ile Thr Met Ser Arg Glu Leu Gly Gln Gly
            20                  25                  30

Ser Phe Gly Met Val Tyr Glu Gly Val Ala Lys Gly Val Val Lys Asp
        35                  40                  45

Glu Pro Glu Thr Arg Val Ala Ile Lys Thr Val Asn Glu Ala Ala Ser
    50                  55                  60

Met Arg Glu Arg Ile Glu Phe Leu Asn Glu Ala Ser Val Met Lys Glu
65                  70                  75                  80

Phe Asn Cys His His Val Val Arg Leu Leu Gly Val Val Ser Gln Gly
                85                  90                  95

Gln Pro Thr Leu Val Ile Met Glu Leu Met Thr Arg Gly Asp Leu Lys
            100                 105                 110

Ser Tyr Leu Arg Ser Leu Arg Pro Glu Met Glu Asn Asn Pro Val Leu
        115                 120                 125

Ala Pro Pro Ser Leu Ser Lys Met Ile Gln Met Ala Gly Glu Ile Ala
    130                 135                 140

Asp Gly Met Ala Tyr Leu Asn Ala Asn Lys Phe Val His Arg Asp Leu
145                 150                 155                 160

Ala Ala Arg Asn Cys Met Val Ala Glu Asp Phe Thr Val Lys Ile Gly
                165                 170                 175

Asp Phe Gly Met Thr Arg Asp Ile Tyr Glu Thr Asp Tyr Tyr Arg Lys
            180                 185                 190

Gly Gly Lys Gly Leu Leu Pro Val Arg Trp Met Ser Pro Glu Ser Leu
        195                 200                 205

Lys Asp Gly Val Phe Thr Thr Tyr Ser Asp Val Trp Ser Phe Gly Val
    210                 215                 220

Val Leu Trp Glu Ile Ala Thr Leu Ala Glu Gln Pro Tyr Gln Gly Leu
225                 230                 235                 240

Ser Asn Glu Gln Val Leu Arg Phe Val Met Glu Gly Gly Leu Leu Asp
                245                 250                 255

Lys Pro Asp Asn Cys Pro Asp Met Leu Phe Glu Leu Met Arg Met Cys
            260                 265                 270

Trp Gln Tyr Asn Pro Lys Met Arg Pro Ser Phe Leu Glu Ile Ile Ser
        275                 280                 285

Ser Ile Lys Glu Glu Met Glu Pro Gly Phe Arg Glu Val Ser Phe Tyr
    290                 295                 300

Tyr Ser Glu Glu Asn Lys Leu Pro Glu Pro Glu Leu Asp Leu Glu
305                 310                 315                 320

Pro Glu Asn Met Glu Ser Val Pro Leu Asp Pro Ser Ala Ser Ser Ser
                325                 330                 335

Ser Leu Pro Leu Pro Asp Arg His Ser Gly His Lys Ala Glu Asn Gly
```

```
                    340                 345                 350
Pro Gly Pro Gly Val Leu Val Leu Arg Ala Ser Phe Asp Glu Arg Gln
            355                 360                 365
Pro Tyr Ala His Met Asn Gly Gly Arg Lys Asn Glu Arg Ala Leu Pro
        370                 375                 380
Leu Pro Gln Ser Ser Thr Cys
385                 390

<210> SEQ ID NO 99
<211> LENGTH: 20
<212> TYPE: DNA
<213> ORGANISM: Artificial Sequence
<220> FEATURE:
<223> OTHER INFORMATION: Negative Control ODN

<400> SEQUENCE: 99
ccaatgataa caaacgcgga                                                     20

<210> SEQ ID NO 100
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 100
agtctcaaac tcagtcttcg                                                     20

<210> SEQ ID NO 101
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 101
gttaatgctg gtaaacaaga                                                     20

<210> SEQ ID NO 102
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 102
gaagtccggg tcacaggcga                                                     20

<210> SEQ ID NO 103
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 103
aacaagagcc ccagcctcgc                                                     20

<210> SEQ ID NO 104
<211> LENGTH: 20
<212> TYPE: DNA
<213> ORGANISM: Artificial Sequence
<220> FEATURE:
<223> OTHER INFORMATION: antisense oligonucleotide
```

<400> SEQUENCE: 104
atgctggtaa acaagagccc                                               20

<210> SEQ ID NO 105
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 105
tgctggtaaa caagagcccc                                               20

<210> SEQ ID NO 106
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 106
ggagtcaaaa tgaatgagcg                                               20

<210> SEQ ID NO 107
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 107
aatctgccta ggcgaggaaa                                               20

<210> SEQ ID NO 108
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 108
gctggtaaac aagagcccca                                               20

<210> SEQ ID NO 109
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 109
agcccaaatc tgcctaggcg                                               20

<210> SEQ ID NO 110
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 110
cctccatttt caaacccgga                                               20

<210> SEQ ID NO 111
<211> LENGTH: 20

```
<212> TYPE: DNA
<213> ORGANISM: Artificial Sequence
<220> FEATURE:
<223> OTHER INFORMATION: antisense oligonucleotide

<400> SEQUENCE: 111
gaaggtcaca gccgaggcga                                              20

<210> SEQ ID NO 112
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 112
tcgctgaagg tcacagccga                                              20

<210> SEQ ID NO 113
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 113
atccaggaca cacacaaagc                                              20

<210> SEQ ID NO 114
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 114
aagtccgggt cacaggcgag                                              20

<210> SEQ ID NO 115
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 115
aagtctcaaa ctcagtcttc                                              20

<210> SEQ ID NO 116
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 116
gtcgtcggcc tccattttca                                              20

<210> SEQ ID NO 117
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 117
```
gcagaaacgc ggagtcaaaa                                               20

<210> SEQ ID NO 118
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 118
gcggcgagct ccttcccaaa                                               20

<210> SEQ ID NO 119
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 119
taatgctggt aaacaagagc                                               20

<210> SEQ ID NO 120
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 120
tttcaaaccc ggagaggcag                                               20

<210> SEQ ID NO 121
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 121
taggcgagga aaacaagcc                                                20

<210> SEQ ID NO 122
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 122
ctcgctgaag gtcacagccg                                               20

<210> SEQ ID NO 123
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 123
gcagcggccc agggctcggc                                               20

<210> SEQ ID NO 124
<211> LENGTH: 20
<212> TYPE: DNA
<213> ORGANISM: Artificial Sequence

```
<220> FEATURE:
<223> OTHER INFORMATION: antisense oligonucleotide

<400> SEQUENCE: 124
gctcgctgaa ggtcacagcc                                               20

<210> SEQ ID NO 125
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 125
cgaaggaaac aatactccga                                               20

<210> SEQ ID NO 126
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 126
gaaacgcgga gtcaaaatga                                               20

<210> SEQ ID NO 127
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 127
gaaacaatac tccgaagggc                                               20

<210> SEQ ID NO 128
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 128
ccaaatccag gacacacaca                                               20

<210> SEQ ID NO 129
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 129
tcggcctcca ttttcaaacc                                               20

<210> SEQ ID NO 130
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 130
tccgggtcac aggcgaggcc                                               20
```

```
<210> SEQ ID NO 131
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 131
aatgaatgag cggctccccc                                                    20

<210> SEQ ID NO 132
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 132
tgaaggtcac agccgaggcg                                                    20

<210> SEQ ID NO 133
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 133
aaggtcacag ccgaggcgag                                                    20

<210> SEQ ID NO 134
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 134
cccaaatcca ggacacacac                                                    20

<210> SEQ ID NO 135
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 135
acaagtctca aactcagtct                                                    20

<210> SEQ ID NO 136
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 136
ggtaaacaag agccccagcc                                                    20
```